(12) United States Patent
Onoda et al.

(10) Patent No.: US 7,547,790 B2
(45) Date of Patent: Jun. 16, 2009

(54) OPTICALLY ACTIVE 4,4-DI-SUBSTITUTED OXAZOLIDINE DERIVATIVE AND METHOD FOR PRODUCING SAME

(75) Inventors: Toshihiko Onoda, Kanagawa (JP); Yoshitaka Nakamura, Kanagawa (JP); Makoto Yamaoka, Kanagawa (JP); Tadahiro Takeda, Kanagawa (JP); Noritada Sato, Kanagawa (JP); Masayoshi Jin, Kanagawa (JP)

(73) Assignee: Sankyo Company, Limited, Tokyo (JP)

( * ) Notice: Subject to any disclaimer, the term of this patent is extended or adjusted under 35 U.S.C. 154(b) by 26 days.

(21) Appl. No.: 11/664,053

(22) PCT Filed: Oct. 26, 2005

(86) PCT No.: PCT/JP2005/019678
§ 371 (c)(1),
(2), (4) Date: Mar. 30, 2007

(87) PCT Pub. No.: WO2006/046595
PCT Pub. Date: May 4, 2006

(65) Prior Publication Data
US 2008/0108828 A1 May 8, 2008

(30) Foreign Application Priority Data
Oct. 28, 2004 (JP) ............................. 2004-313183

(51) Int. Cl.
C07D 263/02 (2006.01)
C07D 413/00 (2006.01)
(52) U.S. Cl. ...................................... 548/215; 548/100
(58) Field of Classification Search ................ 548/100, 548/215
See application file for complete search history.

(56) References Cited

U.S. PATENT DOCUMENTS
5,578,593 A 11/1996 Chen et al.
2005/0043386 A1 2/2005 Nishi et al.

FOREIGN PATENT DOCUMENTS
EP 1 471 054 A1 10/2004
JP 2003-267950 9/2003

OTHER PUBLICATIONS

Stucky, G. Substitutionen und Additionen an (R)-2-tert-Butyl-1,3-oxazolin-3-carbonsaure-methylester, Chem Ber. 122 (1989) 2365-2375.*
Dieter Seebach et al.; "α-Alkylation of Serine with Self-Reproduction of the Center of Chirality," Tetrahedron Letters, vol. 25, No. 24, pp. 2545-2548, (1984).
Von Dieter Seebach et al., "Stereoselective Alkylation at C(α) of Serine, Glyceric Acids, Threonine and Tartaric Acid Involving Heterocyclic Enolates with Exocyclic Double Bonds," Helvetica Chimica Acta., vol. 70, pp. 1194-1216, (1987).
Myriam Alías et al., "Synthesis of (S)-N-tert-Butoxycarbonyl-N,O-isopropylidene-α-methylserinal: A Potential Building Block for the Asymmetric Synthesis of Non-natural Amino Acids," Tetrahedron, vol. 54, pp. 14963-14974, (1998).
Alberto Avenoza et al., "Preparation and Synthetic Applications of (S)-and (R)-N-Boc-N,O-isopropylidene-α-methylserinals: Asymmetric Synthesis of (S)- and (R)-2-Amino-2-methylbutanoic Acids (IVa)," Journal of Organic Chemistry, vol. 64, pp. 8220-8225, (1999).
Alan P. Kozikowski et al., "α-Substituted Quisqualic Acid Analogs: New Metabotropic Glutamate Receptor Group II Selective Antagonists," Bioorganic Medicinal Chemistry Letters, vol. 8, pp. 447-452, (1998).
Alan P. Kozikowski et al., "Synthesis and Biology of the Conformationally Restricted ACPD Analogue, 2-Aminobicyclo[2.1.1]hexane-2,5-dicarboxylic Acid-I, a Potent mGluR Agonist," Journal of Medicinal Chemistry, vol. 41, pp. 1641-1650, (1998).
Alan P. Kozikowski et al., "Synthesis and Metabotropic Glutamate Receptor Activity of A 2-Aminobicyclo[3.2.0]Heptane-2,5-Dicarboxylic Acid, A Molecule Possessing An Extended Glutamate Conformation," Bioorganic & Medicinal Chemistry Letters, vol. 8, pp. 925-930, (1998).

(Continued)

Primary Examiner—Kamal A Saeed
Assistant Examiner—Samantha L Shterengarts
(74) Attorney, Agent, or Firm—Frishauf, Holtz, Goodman & Chick, P.C.

(57) ABSTRACT

An optically active 4,4-di-substituted oxazolidine compound having the formula (I)

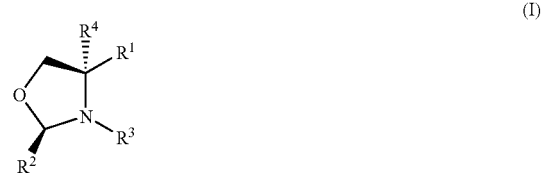

(I)

wherein $R^1$ represents a substituted $C_1$-$C_3$ alkyl group, a substituted $C_2$-$C_3$ alkenyl group, a formyl group, a hydroxymethyl group, a group of the formula COOR, a halogenated methyl group, a phosphonium methyl group; R represents a $C_1$-$C_6$ alkyl group, a $C_2$-$C_6$ alkenyl group, a phenyl group or a benzyl group; $R^2$ represents a $C_1$-$C_6$ alkyl group, a $C_3$-$C_{10}$ cycloalkyl group, or a phenyl group; $R^3$ represents a $C_2$-$C_6$ alkanoyl group, a $C_1$-$C_6$ alkyloxycarbonyl group, a benzoyl group, a phenyloxycarbonyl group or a benzyloxycarbonyl group and $R_4$ represents a $C_1$-$C_6$ alkyl group or a $C_2$-$C_6$ alkenyl group.

17 Claims, No Drawings

OTHER PUBLICATIONS

Matoshi Kiuchi et al., "Synthesis and Immunosuppressive Activity of 2-Substituted 2-aminopropane-1,3-diols and 2-Aminoethanols," *Journal of Medicinal Chemistry*, vol. 43, pp. 2946-2961, (2000).

Klaus Hinterding et al., "First Asymmetric Synthesis of Chiral Analogues of the Novel Immunosuppressant FTY720," *Tetrahedron Letters*, vol. 43, pp. 8095-8097, (2002).

Klaus Hinterding et al., "Synthesis of Chiral Analogues of FTY720 and its Phosphate," *Synthesis*, No. 11, pp. 1667-1670, (2003).

Viresh H. Rawai et al., "Photocyclization Strategy for the Synthesis of Antitumor Agent CC-1065: Synthesis of Dideoxy PDE-I and PDE-II. Synthesis of Thiophene and Furan Analogues of Dideoxy PDE-I and PDE-II," *The Journal of Organic Chemistry*, vol. 52, pp. 19-28, (1987).

Yoshiro Yamagiwa et al., "Synthesis of Anacardic Acids and Ginkoic Acid," *Tetrahedron*, Vo. 43, No. 15, pp. 3387-3394, (1987).

Martin Brunner et al., "Stereocontrolled α-Alkylation of Fully Protected L-Serine," *Eur. J. Org. Chem.* vol. 18, pp. 3879-3883, (2004).

Hidemitsu Uno et al., "A New Approach for Construction of Quarternary Chiral Centers: Preparation of α-Branched Serine Derivatives," *Heterocycles*, vol. 53, No. 5, pp. 1011-1016, (2000).

* cited by examiner

OPTICALLY ACTIVE 4,4-DI-SUBSTITUTED OXAZOLIDINE DERIVATIVE AND METHOD FOR PRODUCING SAME

TECHNICAL FIELD OF THE INVENTION

The present invention relates to optically active 4,4-di-substituted oxazolidine derivatives and procedures for their preparation. The optically active 4,4-di-substituted oxazolidine derivatives of the present invention have advantage as useful synthetic intermediates in new stereoselective industrial manufacturing methods of optically active α,α-di-substituted α-amino acid derivatives and optically active α,α-di-substituted α-amino alcohol derivatives.

BACKGROUND OF THE INVENTION

As a method for the preparation of optically active α,α-di-substituted α-amino acid derivatives through optically active 4,4-di-substituted oxazolidine derivatives as a synthetic intermediate, for example, methods described by Dieter Seebach, et al. (refer to non-patent literature 1 and non-patent literature 2) and by Carlos Cativiela, et al. (refer to non-patent literature 3 and non-patent literature 4) have been known.

The method described by Dieter Seebach, et al., however, is an unsuitable method for industrial large-scale synthesis because of the extremely low-temperature reaction conditions needed and, additionally, the yield is low.

On the other hand, the method described by Carlos Cativiela, et al. is a method that includes the processes of diastereoselective alkylation using an optically active cyano ester compound and Sharpless asymmetric oxidation, but in the former process, the low yield, low stereoselectivity and numerous reaction steps are a disadvantage, and in the latter process, the use of a peroxidized compound and numerous reaction steps are a disadvantage, and these procedures are also unsuitable for industrial large-scale synthesis.

Furthermore, optically active 4,4-di-substituted oxazolidine derivatives have been used as a synthetic intermediate for the preparation of glutamate receptor antagonists, which are optically active α,α-di-substituted α-amino acid derivatives, and its usefulness have already been known. Glutamate receptor antagonists have been reported as effective against epilepsy, brain defects following heart bypass surgery and/or transplantation, attack, cerebral ischemia, pain, spinal cord injury, head trauma, hypoxia at birth, cardiac arrest and hypoglycemia-induced damage, anxiety, neurodegenerative diseases, Huntington's chorea, AIDS-induced dementia, eye damage, retinopathy, cognitive deficiency, Parkinson's disease, Alzheimer's disease, multiple sclerosis, or the like (refer to non-patent literature 5 to 7 and patent literature 1).

Additionally, several reports demonstrate that optically active α,α-di-substituted α-amino alcohol derivatives exert an immunosuppressive activity based on a novel mechanism of action (refer to non-patent literatures 8 to 10 and patent literature 2), and the optically active 4,4-di-substituted oxazolidine derivatives of the present invention are considered to be useful synthetic intermediates for the preparation of the optically active α,α-di-substituted α-amino alcohol derivatives.

As the manufacturing method of the substituted methylenephosphonium salt disclosed in the patent literature 2, for example, the following procedure (non-patent literature 11) has been disclosed, and compound (IV'-a) is synthesized from the known compound (IV''-a) through the compound (V-a) as the synthetic intermediate, as shown in the following reaction scheme.

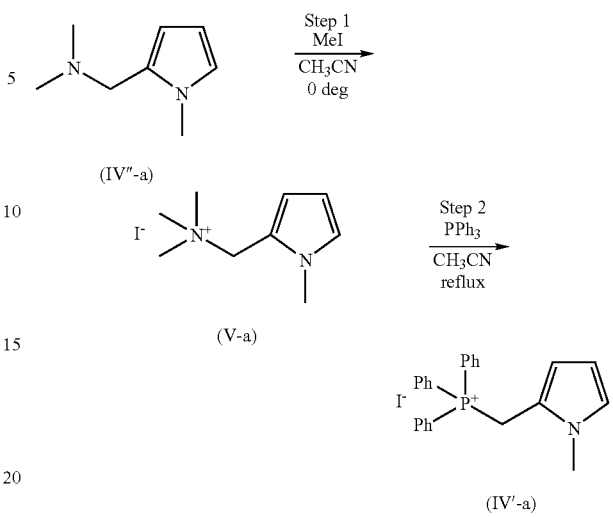

However, this procedure has several disadvantages described below:

(1) In Step 1, methyl iodide, which is a mutagen is used and harmful effects on operators and operational environment are a concern.

(2) In Step 2, the heating condition is indispensable for the reaction to proceed, but the compound (V-a) is thermally unstable and, additionally, partially decomposed before initiation of the reaction and, consequently, low production yield and low purity of the compound (IV'-a) thus obtained are disadvantageous.

(3) As Step 2 is an equilibrium reaction, it is necessary to remove out of the reaction system trimethylamine generated by the progress of the reaction for the reaction to proceed smoothly. Trimethylamine, however, is a malodorous material, and the necessity of special measures such as an amine trap is disadvantageous.

(4) Additionally, in Step 2, long-period heating is needed, and an expensive manufacturing cost, when this method is applied to the industrial manufacturing, becomes a problem.

[Non-patent literature 1] Tetrahedron Letters, vol. 25, 2545 (1984)

[Non-patent literature 2] Helvetica Chimica Acta, vol. 70, 1194 (1987)

[Non-patent literature 3] Tetrahedron, vol. 54, 14963 (1998)

[Non-patent literature 4] Journal of Organic Chemistry, vol. 64, 8220 (1999)

[Non-patent literature 5] Bioorganic Medicinal Chemistry Letters, vol. 8, 447 (1998)

[Non-patent literature 6] Bioorganic Medicinal Chemistry Letters, vol. 8, 925 (1998)

[Non-patent literature 7] Journal of Medicinal Chemistry, vol. 41, 1641 (1998)

[Non-patent literature 8] Journal of Medicinal Chemistry, vol. 43, 2946 (2000)

[Non-patent literature 9] Tetrahedron Letters, vol. 43, 8095 (2002)

[Non-patent literature 10] Synthesis, 1667 (2003)

[Non-patent literature 11] The Journal of Organic Chemistry, vol. 52, 19 (1987)

[Patent literature 1] U.S. Pat. No. 5,578,593 Specification
[Patent literature 2] Japanese Patent Publication (Kokai) Number 2003-4599

DISCLOSURE OF THE INVENTION

Subject to be Solved by the Invention

The subject of the present invention is to provide less-expensive and more efficient stereoselective procedures for the preparation of optically active α,α-di-substituted α-amino acid derivatives and optically active α,α-di-substituted α-amino alcohol derivatives. Furthermore, by providing said manufacturing procedure of the present invention, it becomes possible to perform practical mass production of glutamate receptor antagonists that are useful for therapy against epilepsy, brain deficit following epilepsy, heart bypass surgery, and transplantation of an organ, attack, ischemic brain, pain, spinal cord injury, head trauma, hypoxia at birth, cardiac failure and hypoglycemic damage, anxiety, neurodegenerative diseases, Huntington's disease, AIDS-induced dementia, eye damage, retinopathy, cognitive disorder, Parkinson's disease, Alzheimer's disease, or multiple sclerosis, or the like; or immunosuppressive agents that are useful for therapy against suppression of rejection symptoms caused by organ transplantation or skin transplantation, or for therapy against autoimmune diseases such as rheumatic arthritis, psoriasis, multiple sclerosis, inflammatory bowel disease, lupus erythematosus nephritis, glomerular nephritis, insulin resistant diabetes mellitus, atopic dermatitis, and the like.

Measures to Solve the Subject

The inventors of the present invention have diligently investigated for many years into various procedures for the preparation of α,α-di-substituted α-amino acid derivatives and optically active α,α-di-substituted α-amino alcohol derivatives in order to solve the subject described above, and discovered a synthetic procedure comprising processes through optically active 4,4-di-substituted oxazolidine derivatives shown below and furthermore a preparation procedure by which the substituted-methylenephosphonium salt which is useful as the intermediate can be obtained conveniently in high yield, and consequently, the inventors completed the present invention.

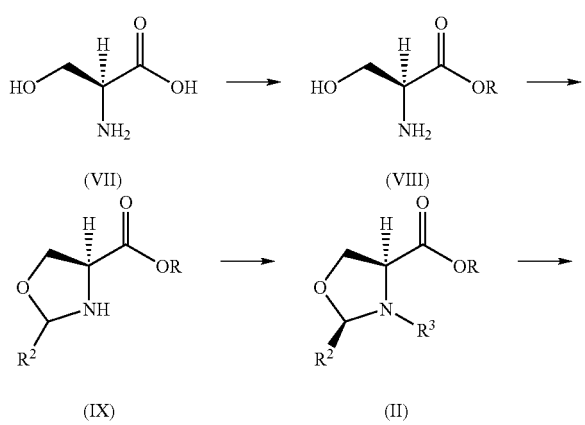

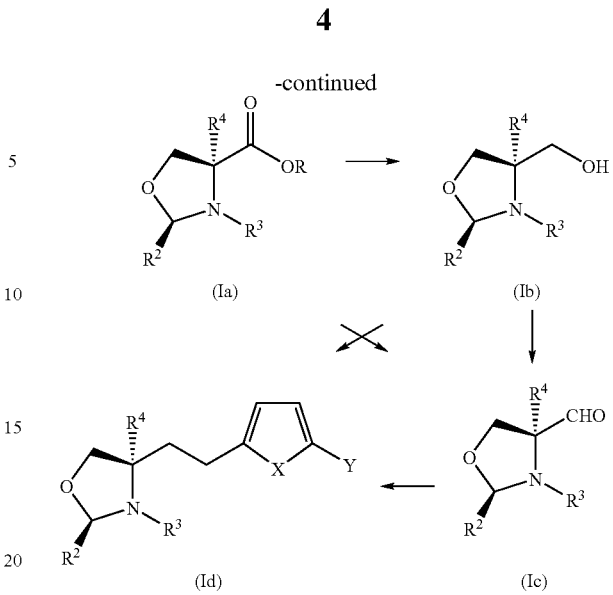

The present invention provides
(1) an optically active 4,4-di-substituted oxazolidine derivative having the general formula (I)

[wherein,
$R^1$ represents a $C_1$-$C_3$ alkyl group which is substituted with one substituent selected from Substituent group A, a $C_2$-$C_3$ alkenyl group which is substituted with one substituent selected from Substituent group A, a halogenated methyl group, a hydroxymethyl group, a formyl group, a group of formula COOR or a phosphonium methyl group,
R represents a $C_1$-$C_6$ alkyl group, a $C_2$-$C_6$ alkenyl group, a phenyl group or a benzyl group,
$R^2$ represents a $C_1$-$C_6$ alkyl group, a $C_3$-$C_{10}$ cycloalkyl group or a phenyl group,
$R^3$ represents a $C_2$-$C_6$ alkanoyl group, a $C_1$-$C_6$ alkyloxycarbonyl group, a benzoyl group, a phenyloxycarbonyl group or a benzyloxycarbonyl group,
$R^4$ represents a $C_1$-$C_6$ alkyl group or a $C_2$-$C_6$ alkenyl group,
Substituent group A represents a phenyl group which may optionally be substituted with from 1 to 3 substituents selected from the group consisting of a halogen atom, a cyano group, a phenyl group, a $C_1$-$C_8$ alkyl group, a $C_1$-$C_9$ alkoxy group and a $C_2$-$C_8$ alkanoyl group, a thienyl group, a N-methylpyrrolyl group or a furanyl group], and preferably
(2) an optically active 4,4-di-substituted oxazolidine derivative having the general formula (I) described in (1) wherein $R^1$ represents a formyl group,
(3) an optically active 4,4-di-substituted oxazolidine derivative having the general formula (I) described in (1) wherein $R^1$ represents a hydroxymethyl group,
(4) an optically active 4,4-di-substituted oxazolidine derivative having the general formula (I) described in (1) wherein R[1] represents a group of formula COOR, and R represents a $C_1$-$C_4$ alkyl group, an allyl group, a phenyl group or a benzyl group, (5) an optically active 4,4-di-substituted oxazolidine derivative having the general formula (I) described in (1) wherein R[1] represents a methoxycarbonyl group or an ethoxycarbonyl group, (6) an optically active 4,4-di-substituted oxazolidine derivative having the general formula (I) described in (1) wherein R[1] represents a halogenated methyl group, (7) an optically active 4,4-di-substituted oxazolidine derivative having the general formula (I) described in (1) wherein R[1] represents an iodinated methyl group, (8) an optically active 4,4-di-substituted oxazolidine derivative having the general formula (I) described in (1) wherein R[1] represents a phosphonium methyl group, (9) an optically active 4,4-di-substituted oxazolidine derivative having the general formula (I) described in (1) wherein R[1] represents a methyltriphenylphosphonium iodide,

(10) an optically active 4,4-di-substituted oxazolidine derivative having the general formula (I) described in (1) wherein R[1] represents an ethyl group or a vinyl group both of which are substituted with one substituent selected from the group consisting of a 4-bromophenyl group, a 4-iodophenyl group, a 4-octylphenyl group, a 4-heptyloxyphenyl group, a 4-octanoylphenyl group, a thienyl group and a N-methylpyrrolyl group,

(11) an optically active 4,4-di-substituted oxazolidine derivative having the general formula (I) described in (1) wherein R[1] represents an ethyl group or a vinyl group both of which are substituted with a N-methylpyrrolyl group,

(12) an optically active 4,4-di-substituted oxazolidine derivative having the general formula (I) described in any one of (1) to (11) wherein R[2] represents an isopropyl group, a t-butyl group, a diethylmethyl group, a cyclohexyl group or an adamantyl group,

(13) an optically active 4,4-di-substituted oxazolidine derivative having the general formula (I) described in any one of (1) to (11) wherein R[2] represents a t-butyl group,

(14) an optically active 4,4-di-substituted oxazolidine derivative having the general formula (I) described in any one of (1) to (13) wherein R[3] represents an acetyl group, a methoxycarbonyl group, an ethoxycarbonyl group, a t-butoxycarbonyl group, a phenyloxycarbonyl group or a benzyloxycarbonyl group,

(15) an optically active 4,4-di-substituted oxazolidine derivative having the general formula (I) described in any one of (1) to (13) wherein R[3] represents a methoxycarbonyl group,

(16) an optically active 4,4-di-substituted oxazolidine derivative having the general formula (I) described in any one of (1) to (15) wherein R[4] represents a methyl group, and

(17) any one of optically active 4,4-di-substituted oxazolidine derivatives having the general formula (I) according to (1) selected from following compounds:
2-t-butyl-4-methyl-1,3-oxazolidine-3,4-dicarboxylic acid 3-t-butyl ester 4-methyl ester,
2-t-butyl-4-methyl-1,3-oxazolidine-3,4-dicarboxylic acid 3-benzyl ester 4-methyl ester,
2-t-butyl-4-methyl-1,3-oxazolidine-3,4-dicarboxylic acid dimethyl ester,
2-t-butyl-4-methyl-1,3-oxazolidine-3,4-dicarboxylic acid 3-ethyl ester 4-methyl ester,
3-acetyl-2-t-butyl-4-methyl-1,3-oxazolidine-4-carboxylic acid methyl ester,
2-t-butyl-4-methyl-1,3-oxazolidine-3,4-dicarboxylic acid 3-phenyl ester 4-methyl ester,
3-benzoyl-2-t-butyl-4-methyl-1,3-oxazolidine-4-carboxylic acid methyl ester,
2-t-butyl-4-hydroxymethyl-4-methyl-1,3-oxazolidine-3-carboxylic acid t-butyl ester,
2-t-butyl-4-hydroxymethyl-4-methyl-1,3-oxazolidine-3-carboxylic acid benzyl ester,
2-t-butyl-4-hydroxymethyl-4-methyl-1,3-oxazolidine-3-carboxylic acid methyl ester,
2-t-butyl-4-hydroxymethyl-4-methyl-1,3-oxazolidine-3-carboxylic acid ethyl ester,
(3-acetyl-2-t-butyl-4-methyl-1,3-oxazolidin-4-yl)methanol,
2-t-butyl-4-hydroxymethyl-4-methyl-1,3-oxazolidine-3-carboxylic acid phenyl ester,
(3-benzoyl-2-t-butyl-4-methyl-1,3-oxazolidin-4-yl)methanol,
2-t-butyl-4-formyl-4-methyl-1,3-oxazolidine-3-carboxylic acid t-butyl ester,
2-t-butyl-4-formyl-4-methyl-1,3-oxazolidine-3-carboxylic acid benzyl ester,
2-t-butyl-4-formyl-4-methyl-1,3-oxazolidine-3-carboxylic acid methyl ester,
2-t-butyl-4-formyl-4-methyl-1,3-oxazolidine-3-carboxylic acid ethyl ester,
3-acetyl-2-t-butyl-4-methyl-1,3-oxazolidine-4-carbaldehyde,
2-t-butyl-4-formyl-4-methyl-1,3-oxazolidine-3-carboxylic acid phenyl ester,
3-benzoyl-2-t-butyl-4-methyl-1,3-oxazolidine-4-carbaldehyde,
2-t-butyl-4-methyl-4-[2-(1-methyl-1H-pyrrol-2-yl)ethyl]-1,3-oxazolidine-3-carboxylic acid t-butyl ester,
2-t-butyl-4-methyl-4-[2-(1-methyl-1H-pyrrol-2-yl)ethyl]-1,3-oxazolidine-3-carboxylic acid benzyl ester,
2-t-butyl-4-methyl-4-[2-(1-methyl-1H-pyrrol-2-yl)ethyl]-1,3-oxazolidine-3-carboxylic acid methyl ester,
2-t-butyl-4-methyl-4-[2-(1-methyl-1H-pyrrol-2-yl)ethyl]-1,3-oxazolidine-3-carboxylic acid phenyl ester,
2-t-butyl-4-methyl-4-[2-(1-methyl-1H-pyrrol-2-yl)ethyl]-1,3-oxazolidine-3-carboxylic acid ethyl ester,
3-acetyl-2-t-butyl-4-methyl-4-[2-(1-methyl-1H-pyrrol-2-yl)ethyl]-1,3-oxazolidine, and
3-benzoyl-2-t-butyl-4-methyl-4-[2-(1-methyl-1H-pyrrol-2-yl)ethyl]-1,3-oxazolidine.

Furthermore, the present invention provides

(18) a procedure for the preparation of a compound having the general formula (Ia) shown below by reacting a compound having the general formula (II) shown below with a compound having the general formula (III) in the presence of a base and a coordinating reagent in the presence or absence of a solvent,

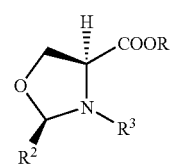

(II)

[wherein,
R represents a $C_1$-$C_6$ alkyl group, a $C_2$-$C_6$ alkenyl group, a phenyl group or a benzyl group,
R[2] represents a $C_1$-$C_6$ alkyl group, a $C_3$-$C_{10}$ cycloalkyl group or a phenyl group, $R^3$ represents a $C_2$-$C_6$ alkanoyl group, a $C_1$-$C_6$ alkyloxycarbonyl group, a benzoyl group, a phenyloxycarbonyl group or a benzyloxycarbonyl group]

$$R^4\text{-}Z \qquad (III)$$

[wherein,
$R^4$ represents a $C_1$-$C_6$ alkyl group or a $C_2$-$C_6$ alkenyl group,
Z represents a halogen atom or a group having the general formula —O—$S(O)_2R^c$, and
$R^c$ represents a methoxyl group, a $C_1$-$C_6$ alkyl group which may optionally be substituted with from 1 to 3 halogen atoms or a phenyl group which may optionally be substituted with from 1 to 3 substituents selected from the group consisting of a halogen atom and a methyl group]

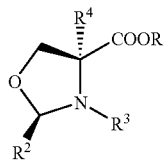

(Ia)

[wherein,
R, $R^2$, $R^3$ and $R^4$ have the same meanings as those indicated hereinbefore],
(19) a procedure for the preparation of a compound having the general formula (Ia) according to (18) wherein the halogen atom represents a bromine atom or an iodine atom,
(20) a procedure for the preparation of a compound having the general formula (Ia) according to any one of (18) and (19) wherein the coordinating reagent employed is one reagent or at least two reagents selected from the group consisting of DMPU, DMI, NMP, DMAc, DMF, DMSO, diglyme, triglyme and tetraglyme,
(21) a procedure for the preparation of a compound having the general formula (Ia) according to any one of (18) and (19) wherein the coordinating reagent employed is triglyme or tetraglyme,
(22) a procedure for the preparation of a compound having the general formula (Ia) according to any one of (18) to (21) wherein the base employed is one base or at least two bases selected from the group consisting of LHMDS, LDA, SHMDS, KHMDS and potassium t-butoxide,
(23) a procedure for the preparation of a compound having the general formula (Ia) according to any one of (18) to (21) wherein the base employed is potassium t-butoxide,
(24) a procedure for the preparation of a compound having the general formula (Ia) according to any one of (18) to (23) wherein the solvent employed is one solvent or at least two solvents selected from the group consisting of tetrahydrofuran, 1,3-dioxolane, 1,4-dioxane and 1,2-dimethoxyethane,
(25) a procedure for the preparation of a compound having the general formula (Ia) according to any one of (18) to (23) wherein the solvent employed is tetrahydrofuran or 1,2-dimethoxyethane,
(26) a procedure for the preparation of a compound having the general formula (Ia) according to any one of (18) to (25) wherein the reaction temperature is between −25° C. and 10° C.,
(27) a procedure for the preparation of a compound having the general formula (Ia) according to any one of (18) to (26) wherein the base is added to the resulting mixture prepared by addition of the coordinating reagent, the compound having the general formula (U) and the compound having the general formula (III) to the solvent,
(28) a procedure for the preparation of a compound having the general formula (Ib) shown below by reacting a compound having the general formula (Ia) shown below with a reducing reagent in a solvent,

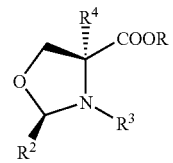

(Ia)

[wherein
R represents a $C_1$-$C_6$ alkyl group, a $C_2$-$C_6$ alkenyl group, a phenyl group or a benzyl group,
$R^2$ represents a $C_1$-$C_6$ alkyl group, a $C_3$-$C_{10}$ cycloalkyl group or a phenyl group,
$R^3$ represents a $C_2$-$C_6$ alkanoyl group, a $C_1$-$C_6$ alkyloxycarbonyl group, a benzoyl group, a phenyloxycarbonyl group or a benzyloxycarbonyl group, and
$R^4$ represents a $C_1$-$C_6$ alkyl group or a $C_2$-$C_6$ alkenyl group]

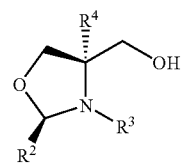

(Ib)

[wherein,
$R^2$, $R^3$ and $R^4$ have the same meanings as those indicated hereinbefore]
(29) a procedure for the preparation of a compound having the general formula (Ib) according to (28) wherein the reducing agent employed is a combination of potassium borohydride and lithium chloride,
(30) a procedure for the preparation of a compound having the general formula (Ic) shown below by reacting a compound having the general formula (Ib) shown below with an oxidizing agent in a solvent,

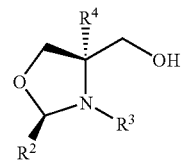

(Ib)

[wherein,
$R^2$ represents a $C_1$-$C_6$ alkyl group, a $C_3$-$C_{10}$ cycloalkyl group or a phenyl group,
$R^3$ represents a $C_2$-$C_6$ alkanoyl group, a $C_1$-$C_6$ alkyloxycarbonyl group, a benzoyl group, a phenyloxycarbonyl group or a benzyloxycarbonyl group, and
$R^4$ represents a $C_1$-$C_6$ alkyl group or a $C_2$-$C_6$ alkenyl group]

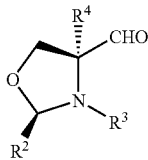

(Ic)

[wherein,
R², R³ and R⁴ have the same meanings as those indicated hereinbefore]
(31) a procedure for the preparation of a compound having the general formula (Ic) according to (30) wherein the oxidizing agent employed is a combination of TEMPO, sodium bromide, sodium hypochloride and sodium hydrogencarbonate,
(32) a procedure for the preparation of a compound having the general formula (Ic) shown below by reacting a compound having the general formula (Ia) shown below with a reducing agent in a solvent,

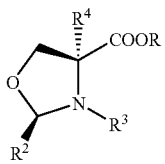

(Ia)

[wherein,
R represents a $C_1$-$C_6$ alkyl group, a $C_2$-$C_6$ alkenyl group, a phenyl group or a benzyl group,
R² represents a $C_1$-$C_6$ alkyl group, a $C_3$-$C_{10}$ cycloalkyl group or a phenyl group,
R³ represents a $C_2$-$C_6$ alkanoyl group, a $C_1$-$C_6$ alkyloxycarbonyl group, a benzoyl group, a phenyloxycarbonyl group or a benzyloxycarbonyl group, and
R⁴ represents a $C_1$-$C_6$ alkyl group or a $C_2$-$C_6$ alkenyl group]

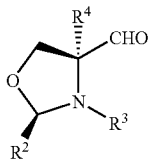

(Ic)

[wherein,
R², R³ and R⁴ have the same meanings as those indicated hereinbefore]
(33) a procedure for the preparation of a compound having the general formula (Ic) according to (32) wherein the reducing agent employed is sodium bis(2-methoxyethoxy)aluminum hydride,
(34) a procedure for the preparation of a compound having the general formula (Id) shown below by conducting a condensation reaction between a compound having the general formula (Ic) shown below and a compound having the general formula (IV) shown below in the presence of a base in a solvent, followed by hydrogenating the product thus obtained,

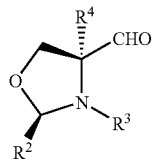

(Ic)

[wherein,
R² represents a $C_1$-$C_6$ alkyl group, a $C_3$-$C_{10}$ cycloalkyl group or a phenyl group,
R³ represents a $C_2$-$C_6$ alkanoyl group, a $C_1$-$C_6$ alkyloxycarbonyl group, a benzoyl group, a phenyloxycarbonyl group or a benzyloxycarbonyl group, and
R⁴ represents a $C_1$-$C_6$ alkyl group or a $C_2$-$C_6$ alkenyl group]

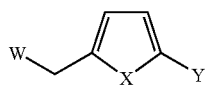

(IV)

[wherein,
W represents a phosphonium salt or a phosphonic acid ester,
X represents a vinylene group, a sulfur atom, a nitrogen atom substituted with a methyl group and a $C_1$-$C_6$ alkyl group, a nitrogen atom substituted with a silyl group, a nitrogen atom substituted with an acyl group or an oxygen atom, and
Y represents a hydrogen atom, a halogen atom, a cyano group, a $C_1$-$C_8$ alkyl group, a $C_1$-$C_8$ alkoxyl group or a $C_2$-$C_8$ alkanoyl group]

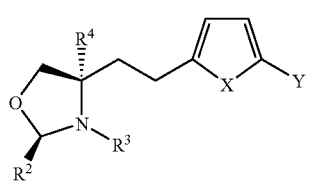

(Id)

[wherein,
R², R³, R¹, X and Y have the same meanings as those indicated hereinbefore]
(35) a procedure for the preparation of a compound having the general formula (Id) according to (34) wherein W is triphenylphosphonium iodide,
(36) a procedure for the preparation procedure of a compound having the general formula (Id) according to (34) or (35) wherein a base employed is potassium t-butoxide,
(37) a procedure for the preparation of a compound having the general formula (Id) shown below by conducting successively a conversion of a compound having the general formula (Ib) shown into a compound having the general formula (V) shown below according to a conventional method, condensation of the product thus obtained with a compound having the general formula (VI) shown below in the presence of a base in a solvent, and the hydrogenation of the product thus obtained,

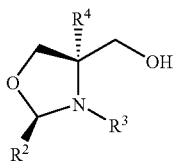

(Ib)

[wherein, $R^2$ represents a $C_1$-$C_6$ alkyl group, a $C_3$-$C_{10}$ cycloalkyl group or a phenyl group, $R^3$ represents a $C_2$-$C_6$ alkanoyl group, a $C_1$-$C_6$ alkyloxycarbonyl group, a benzoyl group, a phenyloxycarbonyl group or a benzyloxycarbonyl group, and $R^4$ represents a $C_1$-$C_6$ alkyl group or a $C_2$-$C_6$ alkenyl group]

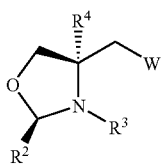

(V)

[wherein, $R^2$, $R^3$ and $R^4$ have the same meanings as those indicated hereinbefore, and W represents a phosphonium salt or a phosphonic acid ester]

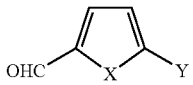

(VI)

[wherein,

X represents a vinylene group, a sulfur atom, a nitrogen atom substituted with a $C_1$-$C_6$ alkyl group, a nitrogen atom substituted with a silyl group, a nitrogen atom substituted with an acyl group or an oxygen atom, and Y represents a hydrogen atom, a halogen atom, a cyano group, a $C_1$-$C_8$ alkyl group, a $C_1$-$C_8$ alkoxyl group or a $C_2$-$C_8$ alkanoyl group]

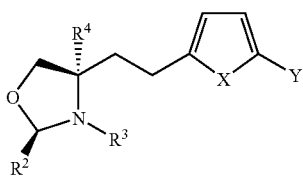

(Id)

[wherein, $R^2$, $R^3$, $R^4$, X and Y have the same meanings as those indicated hereinbefore] and

(38) a procedure for the preparation of a compound having the general formula (Id) according to (37) wherein W is triphenylphosphonium iodide.

Additionally, the present invention provides

(39) a procedure for the preparation of a compound having the general formula (IV') shown below which is characterized by reacting a compound having the general formula (IV''') or a salt thereof with a compound having the general formula (A) in the presence of a compound having the general formula (B) in a solvent,

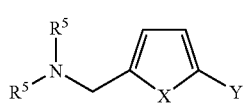

(IV''')

[wherein, $R^5$ represents a $C_1$-$C_6$ alkyl group which may optionally be substituted with substituent(s) selected from Substituent group α or a 5- to 10-membered aromatic group which may optionally be substituted with substituent(s) selected from Substituent group α, or two $R^5$ groups together with the nitrogen atom to which they are bound form a 4- to 8-membered nitrogen-containing heterocyclic group which may optionally be substituted with substituent(s) selected from Substituent group α, X represents a vinylene group, a sulfur atom, a nitrogen atom substituted with a $C_1$-$C_6$ alkyl group, a nitrogen atom substituted with a silyl group, a nitrogen atom substituted with an acyl group or an oxygen atom, Y represents a hydrogen atom, a halogen atom, a cyano group, a $C_1$-$C_8$ alkyl group, a $C_1$-$C_8$ alkoxyl group or a $C_2$-$C_8$ alkanoyl group, and Substituent group α represents a halogen atom, a cyano group, a $C_1$-$C_8$ alkyl group, a $C_1$-$C_8$ alkoxyl group, a $C_1$-$C_8$ alkylthio group and an acyl group]

(A)

[wherein, $R^6$ represents a $C_1$-$C_6$ alkyl group which may optionally be substituted with substituent(s) selected from Substituent group α, a $C_1$-$C_6$ alkoxyl group which may optionally be substituted with substituent(s) selected from Substituent group α, a 5- to 10-membered aromatic group which may optionally be substituted with substituent(s) selected from Substituent group α, or a 5- to 10-membered aromatic-oxy group which may optionally be substituted with substituent(s) selected from Substituent group α, and Substituent group α has the same meaning as that described above]

$R^7$—V  (B)

[wherein, $R^7$ represents an acyl group,

V represents a halogen atom or a group having the general formula —O—S(O)$_2$$R^c$, and $R^c$ represents a methoxyl group, a $C_1$-$C_6$ alkyl group which may optionally be substituted with from 1 to 3 halogen atoms or a phenyl group which may optionally be substituted with from 1 to 3 substituents selected from the group consisting of a halogen atom and a methyl group]

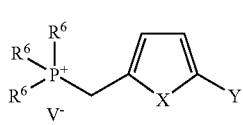

(IV')

[wherein,
$R^6$, V, X and Y have the same meanings as those described above]

(40) a procedure for the preparation of a compound having the general formula (IV') according to (39) wherein X represents a nitrogen atom substituted with a methyl group,
(41) a procedure for the preparation of a compound having the general formula (IV') according to (39) or (40) wherein Y represents a hydrogen atom, a $C_1$-$C_6$ alkyl group or a $C_1$-$C_6$ alkoxyl group,
(42) a procedure for the preparation procedure of a compound having the general formula (IV') according to any one of (39) to (41) wherein $R^5$ represents a $C_1$-$C_6$ alkyl group or two $R^5$ groups together with the nitrogen atom to which they are bound form a pyrrolidine or piperidine group,
(43) a procedure for the preparation of a compound having the general formula (IV') according to any one of (39) to (42) wherein $R^6$ represents a phenyl group,
(44) a procedure for the preparation of a compound having the general formula (IV') according to any one of (39) to (43) wherein $R^7$ represents a $C_1$-$C_6$ alkylcarbonyl group, and
(45) a procedure for the preparation of a compound having the general formula (Id) by condensing a compound having the general formula (IV'), which is prepared by reacting a compound having the general formula (IV'') or a salt thereof with a compound having the general formula (A) in the presence of a compound having the general formula (B) in a solvent, with a compound of the general formula (Ic) in the presence of a base in a solvent, followed by hydrogenation of the product thus obtained;

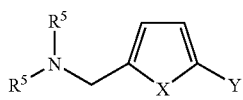

(IV'')

[wherein,
$R^5$ represents a $C_1$-$C_6$ alkyl group which may optionally be substituted with substituent(s) selected from Substituent group α or a 5- to 10-membered aromatic group which may optionally be substituted with substituent(s) selected from Substituent group α, or two $R^5$ groups together with the nitrogen atom to which they are bound form a 4- to 8-membered nitrogen-containing heterocyclic group which may optionally be substituted with substituent(s) selected from Substituent group α,
X represents a vinylene group, a sulfur atom, a nitrogen atom substituted with a $C_1$-$C_6$ alkyl group, a nitrogen atom substituted with a silyl group, a nitrogen atom substituted with an acyl group or an oxygen atom,
Y represents a hydrogen atom, a halogen atom, a cyano group, a $C_1$-$C_8$ alkyl group, a $C_1$-$C_8$ alkoxyl group or a $C_2$-$C_8$ alkanoyl group, and
Substituent group α represents a halogen atom, a cyano group, a $C_1$-$C_8$ alkyl group, a $C_1$-$C_8$ alkoxyl group, a $C_1$-$C_8$ alkylthio group and an acyl group]

(A)

[wherein,
$R^6$ represents a $C_1$-$C_6$-alkyl group which may optionally be substituted with substituent(s) selected from Substituent group α, a $C_1$-$C_6$ alkoxyl group which may optionally be substituted with substituent(s) selected from Substituent group α, a 5- to 10-membered aromatic group which may optionally be substituted with substituent(s) selected from Substituent group α, or a 5- to 10-membered aromatic-oxy group which may optionally be substituted with substituent(s) selected from Substituent group α, and Substituent group α has the same meaning as that described above]

(B)

[wherein,
$R^7$ represents an acyl group,
V represents a halogen atom or a group having the general formula —O—S(O)$_2$R$^c$, and
$R^c$ represents a methoxyl group, a $C_1$-$C_6$ alkyl group which may optionally be substituted with from 1 to 3 halogen atoms or a phenyl group which may optionally be substituted with from 1 to 3 substituents selected from the group consisting of a halogen atom and a methyl group]

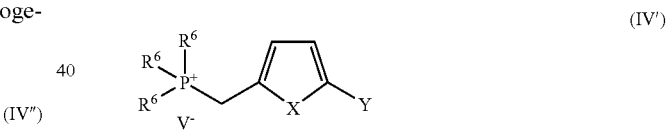

(IV')

[wherein,
$R^6$, V, X and Y have the same meanings as those described above]

(Ic)

[wherein,
$R^2$ represents a $C_1$-$C_6$ alkyl group, a $C_3$-$C_{10}$ cycloalkyl group or a phenyl group,
$R^3$ represents a $C_2$-$C_6$ alkanoyl group, a $C_1$-$C_6$ alkyloxycarbonyl group, a benzoyl group, a phenyloxycarbonyl group or a benzyloxycarbonyl group, and
$R^4$ represents a $C_1$-$C_6$ alkyl group or a $C_2$-$C_6$ alkenyl group]

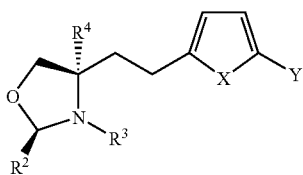

(Id)

[wherein,

R², R³, R⁴, X and Y have the same meanings as those indicated hereinbefore].

In the general formula (I), the "$C_1$-$C_3$ alkyl group" in the definition of $R^1$ can be, for example, a methyl, ethyl, 2-methylethyl or n-propyl group, and is preferably an ethyl group.

In the general formula (I), the "$C_2$-$C_3$ alkenyl group" in the definition of $R^1$ can be, for example, a vinyl, 2-methylvinyl or n-propenyl group, and is preferably a vinyl group.

In the general formula (I), the "$C_1$-$C_6$ alkyl group" in the definitions of R, $R^2$ and $R^4$ can be, for example, a methyl, ethyl, n-propyl, i-propyl, n-butyl, isobutyl, s-butyl, t-butyl, n-pentyl, diethylmethyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl 1,1-dimethylbutyl, 1,2-dimethylbutyl, 1,3-dimethylbutyl, 2,3-dimethylbutyl or 2-ethylbutyl group, and is preferably a $C_1$-$C_4$ alkyl group, and more preferably R and $R^4$ are a methyl group and $R^2$ is a t-butyl group.

In the general formula (I), the "$C_2$-$C_6$ alkenyl group" in the definitions of R and $R^4$ can be, for example, a vinyl, allyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl or 5-hexenyl group, and is preferably a $C_1$-$C_4$ alkenyl group and more preferably a vinyl group or an allyl group.

In the general formula (I), the "$C_3$-$C_{10}$ cycloalkyl group" in the definition of $R^2$ can be, for example, a cyclopropyl, cyclobutyl, cyclopentyl, cyclohexyl, cycloheptyl, cyclooctyl, cyclononyl, cyclodecyl or adamantyl group, and is preferably a $C_5$-$C_{10}$ cycloalkyl group and more preferably a cyclohexyl group or an adamantyl group.

In the general formula (I), the "$C_2$-$C_6$ alkanoyl group" in the definition of $R^3$ can be, for example, an acetyl, propionyl, isopropionyl, n-butanoyl, isobutanoyl, n-pentanoyl, isopentanoyl, 2-methylbutanoyl, pivaloyl, n-hexanoyl, 2-methylpentanoyl, 3-methylpentanoyl or hexanoyl group, and is preferably a $C_2$-$C_4$ alkanoyl group and more preferably an acetyl group.

In the general formula (I), the "$C_1$-$C_6$ alkyloxycarbonyl group" in the definition of $R^3$ can be, for example, a methoxycarbonyl, ethoxycarbonyl, propyloxycarbonyl, n-butoxycarbonyl t-butoxycarbonyl, pentyloxycarbonyl or hexyloxycarbonyl group, and is preferably a $C_1$-$C_4$ alkyloxycarbonyl group and more preferably a methoxycarbonyl group.

In the formulae shown above, the "halogen atom" in the definitions of Substituent groups A and Y can be, for example, a fluorine atom, a chlorine atom, a bromine atom or an iodine atom.

In the formulae shown above, the "$C_1$-$C_8$ alkyl group" in the definitions of Substituent groups A and Y can be, for example, a group shown as the "$C_1$-$C_6$ alkyl group" in the definitions described above, a heptyl group or an octyl group, and is preferably a $C_6$-$C_8$ alkyl group and more preferably an octyl group.

In the formulae shown above, the "$C_1$-$C_8$ alkoxyl group" in the definitions of Substituent groups A and Y can be, for example, a methoxy, ethoxy, n-propoxy, isopropoxy, n-butoxy, isobutoxy, s-butoxy, t-butoxy, n-pentyloxy, isopentyloxy, 2-methylbutoxy, neopentyloxy, 1-ethylpropoxy, n-hexyl, isohexyl, 4-methylpentyl, 3-methylpentyl, 2-methylpentyloxy, 1-methylpentyloxy, 3,3-dimethylbutoxy, 2,2-dimethylbutyl, 1,1-dimethylbutyl, 1,2-dimethylbutyl, 1,3-dimethylbutoxy, 2,3-dimethylbutoxy, 2-ethylbutoxy, heptyloxy or octyloxy group, and preferably a $C_6$-$C_8$ alkoxyl group and more preferably a heptyloxy group.

In the formulae shown above, the "$C_2$-$C_8$ alkanoyl group" in the definitions of Substituent groups A and Y can be, for example, a group shown as the "$C_2$-$C_6$ alkanoyl group" in the definitions described above, a heptanoyl group or an octanoyl group, and is preferably a $C_6$-$C_8$ alkanoyl group and more preferably an octanoyl group.

In the formulae shown above, the "phosphonium salt" in the definition of W can be, for example, trimethylphosphonium chloride, trimethylphosphonium bromide, trimethylphosphonium iodide, triethylphosphonium chloride, triethylphosphonium bromide, triethylphosphonium iodide, tripropylphosphonium chloride, tripropylphosphonium bromide, tripropylphosphonium iodide, tributylphosphonium chloride, tributylphosphonium bromide, tributylphosphonium iodide, triphenylphosphonium chloride, triphenylphosphonium bromide or triphenylphosphonium iodide, and is preferably triphenylphosphonium chloride.

In the formulae shown above, the "phosphonic acid ester" in the definition of W can be, for example, dimethyl phosphonate, diethyl phosphonate, ditrifluoroethyl phosphonate, diphenyl phosphonate, or di-o-tolyl phosphonate, and is preferably diethyl phosphonate.

In the formulae shown above, the "$C_1$-$C_6$ alkyl group" in the definition of X can be, for example, a methyl, ethyl, n-propyl, i-propyl, n-butyl, isobutyl, s-butyl, t-butyl, n-pentyl, diethylmethyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group, and is preferably a $C_1$-$C_4$ alkyl group, and more preferably a methyl group.

In the formulae shown above, the "silyl group" in the definition of X can be, for example, a trimethylsilyl, triethylsilyl, isopropyldimethylsilyl, t-butyldimethylsilyl, methyldiisopropylsilyl, methyldi-t-butylsilyl, triisopropylsilyl, methyldiphenylsilyl, isopropyldiphenylsilyl, butyldiphenylsilyl or phenyldiisopropylsilyl group, and is preferably a trimethylsilyl, triethylsilyl, isopropyldimethylsilyl or t-butyldimethylsilyl group.

In the formulae shown above, the "acyl group" in the definition of X can be, for example, a formyl, carboxyl, carbamoyl, $C_1$-$C_6$ alkylcarbonyl (for example, an acetyl, butanoyl, isobutanoyl or isopentanoyl group), $C_1$-$C_6$ alkoxycarbonyl (for example, a methoxycarbonyl, ethoxycarbonyl, propoxycarbonyl or t-butoxycarbonyl group), $C_6$-$C_{14}$ arylcarbonyl (for example, a benzoyl, 1-naphthoyl or 2-naphthoyl group), $C_6$-$C_{14}$ aryloxycarbonyl (for example, a phenyloxycarbonyl or naphthyloxycarbonyl group), $C_7$-$C_{13}$ aralkyloxycarbonyl (for example, a benzyloxycarbonyl or phenethyloxycarbonyl group), mono- or di-$C_1$-$C_6$ alkylcarbamoyl the alkyl group(s) of which may optionally be substituted with from 1 to 3 substituents selected from the group consisting of a halogen atom and a $C_1$-$C_6$ alkoxycarbonyl group (for example, a methylcarbamoyl, ethylcarbamoyl, dimethylcarbamoyl, diethylcarbamoyl, ethylmethylcarbamoyl, propylcarbamoyl or trifluoroethylcarbamoyl group), $C_6$-$C_{14}$ arylcarbamoyl (for example, a phenylcarbamoyl group), $C_3$-$C_{10}$ cycloalkylcarbamoyl (for example, a cyclopropylcarbamoyl group), $C_7$-$C_{13}$ aralkylcarbamoyl (for example, a benzylcarbamoyl group), $C_1$-$C_6$ alkylsulfonyl (for example, a methylsulfonyl group), $C_6$-$C_{14}$ arylsulfonyl (for example, a phenylsulfonyl group), nitrogen-containing heterocyclic-carbonyl which may optionally be substituted with a hydroxyl group, (for example, a pyrrolidinylcarbonyl or piperidinocarbonyl group), $C_1$-$C_6$ alkylsulfinyl (for example, a methylsulfinyl group), $C_1$-$C_6$ alkoxycarbamoyl (for example, a methoxycarbamoyl group), aminocarbamoyl, hydroxycarbampyl or thiocarbampyl group, and is preferably a formyl, $C_1$-$C_6$ alkylcarbonyl, $C_1$-$C_6$ alkoxycarbonyl, $C_6$-$C_{14}$ arylcarbonyl, $C_7$-$C_{13}$ aralkyloxycarbonyl group and more preferably an acetyl, methoxycarbonyl, ethoxycarbonyl, benzoyl or benzyloxycarbonyl group.

In the formulae shown above, X is preferably a vinylene group, a sulfur atom or a nitrogen atom substituted with a $C_1$-$C_6$ alkyl group and more preferably a vinylene group, a sulfur atom or a nitrogen atom substituted with a methyl group.

In the formulae shown above, Y is preferably a hydrogen atom, a halogen atom, a $C_1$-$C_8$ alkyl group, a $C_1$-$C_8$ alkoxyl group or a $C_2$-$C_8$ alkanoyl group and more preferably a hydrogen atom, a halogen atom, a methyl group, an octyl group, a methoxyl group or a heptyloxy group.

The definition of each substituent of compounds having general formulae (IV'), (IV"), (A) and (B) of the present invention is described in detail below.

The "$C_1$-$C_6$ alkyl group" of the "$C_1$-$C_6$ alkyl group which may optionally be substituted with substituent(s) selected from Substituent group α" in the definitions of $R^5$ can be, for example, a methyl, ethyl, n-propyl, isopropyl, butyl, isobutyl, sec-butyl, t-butyl, pentyl, isopentyl, neopentyl, 1-ethylpropyl, hexyl, isohexyl, 1,1-dimethylbutyl, 2,2-dimethylbutyl, 3,3-dimethylbutyl or 2-ethylbutyl group, and is preferably a methyl, ethyl, propyl, isopropyl, butyl or isobutyl group, and more preferably a methyl or ethyl group.

The "which may optionally be substituted with substituent(s) selected from Substituent group α" of the "$C_1$-$C_6$ alkyl group which may optionally be substituted with substituent(s) selected from Substituent group α" described above means that substitutable positions of said $C_1$-$C_6$ alkyl group may optionally be substituted with from 1 to 3 substituents selected from Substituent group α.

The "5- to 10-membered aromatic ring" of the "5- to 10-membered aromatic group which may optionally be substituted with substituent(s) selected from Substituent group α" in the definition of $R^5$ shown above is, for example, a 5- to 10-membered aromatic hydrocarbon ring or a 5- to 10-membered aromatic heterocyclic ring. A 5- to 10-membered aromatic hydrocarbon ring is preferably a benzene ring or a naphthalene ring, and more preferably a benzene ring. On the other hand, a 5- to 10-membered aromatic heterocyclic ring is preferably a 5- to 10-membered aromatic heterocyclic ring which contains 1 to 4 heteroatoms selected from the group consisting of an oxygen, sulfur and nitrogen atom in addition to the carbon atoms as the ring-composing atoms, and is, for example, furan, thiophene, pyrrole, oxazole, isoxazole, thiazole, isothiazole, imidazole, pyrazole, 1,2,3-oxadiazole, furazan, 1,2,3-thiadiazole, 1,2,3-triazole, pyridine, pyridazine, pyrimidine, triazine, benzofuran, isobenzofuran, benzo[b] thiophene, indole, isoindole, 1H-indazole, benzimidazole, benzoxazole, 1,2-benzisoxazole, bonzothiazole, 1,2-benzoisothiazole, 1H-benzotriazole, quinoline or isoquinoline, and more preferably furan or thiophene.

The "4- to 8-membered nitrogen-containing heterocyclic group" of the "4- to 8-membered nitrogen-containing heterocyclic group which may optionally be substituted with substituent(s) selected from Substituent group α" is, for example, azetidine, pyrrolidine, piperidine, azepan, morpholine or piperazine, and preferably pyrrolidine or piperidine.

The definition of each substituent of the "Substituent group α" is described below.

The "halogen atom" is, for example, a fluorine, chlorine, bromine or iodine atom.

The "$C_1$-$C_8$ alkyl group" is, for example, a methyl, ethyl, n-propyl, i-propyl, butyl, isobutyl, sec-butyl, t-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl or octyl group.

The "$C_1$-$C_8$ alkoxyl group" is a group wherein a terminal of the "$C_1$-$C_8$ alkyl group" shown above is bound to an oxygen atom.

The "$C_1$-$C_8$ alkylthio group" is a group wherein a terminal of the "$C_1$-$C_8$ alkyl group" shown above is bound to a sulfur atom.

The "acyl group" can be, for example, a group of formula —$COR^{3'}$, —$CO_2R^{3'}$, —$SO_2R^{3'}$, —$SOR^{3'}$, —$PO_3R^{3'}R^{4'}$, —CO—$NR^{3a}R^{4a}$ or —CS—$NR^{3a}R^{4a}$ [wherein, $R^{3'}$ and $R^{4'}$ are the same or different and each represents a hydrogen atom, a hydrocarbon group or a heterocyclic group and $R^{3a}$ and $R^{4a}$ groups are the same or different and each represents a hydrogen atom, a hydrocarbon group or a heterocyclic group, or $R^{3a}$ and $R^{4a}$ groups together with an adjacent nitrogen atom may form a nitrogen-containing heterocyclic ring].

The "hydrocarbon group" described for $R^{3'}$, $R^{4'}$, $R^{3a}$ or $R^{4a}$ is a "$C_1$-$C_6$ alkyl group", a "$C_3$-$C_6$ cycloalkyl group", a "$C_6$-$C_{10}$ aryl group" or a "$C_7$-$C_{13}$ aralkyl group".

The "nitrogen-containing heterocyclic ring" formed by $R^{3a}$ and $R^{4a}$ groups together with an adjacent nitrogen atom is a 5- to 7-membered nitrogen-containing heterocyclic ring which may contain at least one nitrogen atom and 1 or 2 heteroatoms selected from the group consisting of an oxygen, sulfur and nitrogen atom in addition to the carbon atoms as the ring-composing atoms, and is preferably pyrrolidine, imidazolidine, pyrazolidine, piperidine, piperazine, morpholine or thiomorpholine.

The preferred "acyl group" can be, for example, a formyl, carboxyl, carbamoyl, $C_1$-$C_6$ alkylcarbonyl (for example, an acetyl, butanoyl, isobutanoyl or isopentanoyl group), $C_1$-$C_6$ alkoxycarbonyl (for example, a methoxycarbonyl, ethoxycarbonyl, propoxycarbonyl or t-butoxycarbonyl group), $C_6$-$C_{14}$ arylcarbonyl (for example, a benzoyl, 1-naphthoyl or 2-naphthoyl group), $C_6$-$C_{14}$ aryloxycarbonyl (for example, a phenyloxycarbonyl or naphthyloxycarbonyl group), $C_7$-$C_{13}$ aralkyloxycarbonyl (for example, a benzyloxycarbonyl or phenethyloxycarbonyl group), mono- or di-$C_1$-$C_6$ alkylcarbamoyl the alkyl group(s) of which may optionally be substituted with from 1 to 3 substituents selected from the group consisting of a halogen atom and a $C_1$-$C_6$ alkoxycarbonyl group (for example, a methylcarbamoyl, ethylcarbamoyl, dimethylcarbamoyl, diethylcarbamoyl, ethylmethylcarbamoyl, propylcarbamoyl or trifluoroethylcarbamoyl group), $C_6$-$C_{14}$ arylcarbamoyl (for example, a phenylcarbamoyl group), $C_3$-$C_{10}$ cycloalkylcarbamoyl (for example, a cyclopropylcarbamoyl group), $C_7$-$C_{13}$ aralkylcarbamoyl (for example, a benzylcarbamoyl group), $C_1$-$C_6$ alkylsulfonyl (for example, a methylsulfonyl group), $C_6$-$C_{14}$ arylsulfonyl (for example, a phenylsulfonyl group), nitrogen-containing heterocyclic-carbonyl which may optionally be substituted with a hydroxyl group (for example, a pyrrolidinylcarbonyl or piperidinocarbonyl group), $C_1$-$C_6$ alkylsulfinyl (for example, a methylsulfinyl group), $C_1$-$C_6$ alkoxycarbamoyl (for example, a methoxycarbamoyl group), aminocarbamoyl, hydroxycarbamoyl or thiocarbamopyl group.

The "$C_1$-$C_6$ alkyl group" of the "$C_1$-$C_6$ alkyl group which may optionally be substituted with substituent(s) selected from Substituent group α" and the "5- to 10-membered aromatic group" of the "5- to 10-membered aromatic group which may optionally be substituted with substituent(s) selected from Substituent group α" in the definition of $R^6$ described above have the same meanings as those indicated in the definition of $R^5$ described above.

The "$C_1$-$C_6$ alkoxyl group which may optionally be substituted with substituent(s) selected from Substituent group α" in the definition of $R^6$ described above is a group wherein a terminal of the "$C_1$-$C_6$ alkyl group which may optionally be substituted with substituent(s) selected from Substituent group α" in the definition of $R^5$ described above is bound to an oxygen atom.

The "5- to 10-membered aromatic-oxy group which may optionally be substituted with substituent(s) selected from Substituent group α" in the definition of $R^6$ described above is a group wherein a terminal of the "5- to 10-membered aromatic group which may optionally be substituted with substituent(s) selected from Substituent group α" in the definition of $R^5$ described above is bound to an oxygen atom.

The "acyl group" in the definition of $R^7$ described above has the same meaning as the "acyl group" indicated in the definition of Substituent group α, and is preferably a $C_1$-$C_6$ alkylcarbonyl group (for example, an acetyl, butanoyl or isobutanoyl group).

The "$C_1$-$C_6$ alkyl group which may optionally be substituted with from 1 to 3 halogen atoms" in the definition of $R^c$ described above can be, for example, a fluoromethyl, difluoromethyl, trifluoromethyl, difluoroethyl or trifluoroethyl group, and preferably a trifluoromethyl group.

The "phenyl group which may optionally be substituted with from 1 to 3 substituents selected from the group consisting of a halogen atom and a methyl group" in the definition of $R^c$ described above can be, for example, a 4-fluorophenyl, 4-chlorophenyl, 3,4-dichlorophenyl, 4-methylphenyl or 3,4-dimethylphenyl group, and is preferably a 4-dimethylphenyl group.

$R^5$ described above is preferably a $C_1$-$C_{10}$ alkyl group which may optionally be substituted with substituent(s) selected from Substituent group α or a 4- to 8-membered nitrogen-containing heterocyclic group formed by two $R^5$ groups together with a nitrogen atom to which they are bound which may optionally be substituted with substituent(s) selected from Substituent group α, more preferably a $C_1$-$C_6$ alkyl group, or pyrrolidine or piperidine formed by two $R^1$ groups together with a nitrogen atom to which two $R^5$ groups are bound, and still more preferably a methyl or ethyl group, or pyrrolidine or piperidine formed by two $R^5$ groups together with a nitrogen atom to which they are bound.

$R^6$ described above is preferably a $C_1$-$C_6$ alkyl group or a 5- to 10-membered aromatic ring group, and more preferably a phenyl group.

$R^7$ described above is preferably a $C_1$-$C_6$ alkylcarbonyl group, and more preferably an acetyl group.

V described above is preferably a chlorine atom, a bromine atom or an iodine atom, and more preferably a chlorine or iodine atom.

X described above is preferably a vinylene group, a sulfur atom or a nitrogen atom substituted with a $C_1$-$C_6$ alkyl group, and more preferably a vinylene group, a sulfur atom or a nitrogen atom substituted with a methyl group.

Y described above is preferably a hydrogen atom, a halogen atom, a $C_1$-$C_8$ alkyl group, a $C_1$-$C_8$ alkoxyl group or a $C_2$-$C_8$ alkanoyl group, and more preferably a hydrogen atom, a halogen atom, a methyl group, an octyl group, a methoxyl group or a heptyloxy group.

Substituent group α described above is preferably a halogen atom, a $C_1$-$C_8$ alkyl group, a $C_1$-$C_8$ alkoxyl group or an acyl group, more preferably a $C_1$-$C_6$ alkyl group or a $C_1$-$C_6$ alkoxyl group, and particularly preferably a methyl group or a methoxyl group.

When the compounds of the present invention can form salt thereof, these compounds can be used as their salts. Such a salt is, for example, an inorganic base salt, an organic base salt, an inorganic acid salt, an organic acid salt, or a basic or acidic amino acid salt.

The inorganic base salt is preferably an alkali metal salt such as a sodium salt, potassium salt or the like; an alkaline earth metal salt such as a calcium salt, magnesium salt or the like; an aluminum salt; an ammonium salt or the like.

The organic base salt is preferably a trimethylamine salt, triethylamine salt, pyridine salt, picoline salt, ethanolamine salt, diethanolamine salt, triethanolamine salt, dicyclohexylamine salt, N,N-dibenzylethylenediamine salt or the like.

The inorganic acid salt is preferably a hydrochloride, a hydrobromide, a nitrate, a sulfate, a phosphate or the like.

The organic acid salt is preferably a formate, an acetate, a trifluoroacetate, a fumarate, an oxalate, a tartrate, a maleate, a citrate, a succinate, a malate, methanesulfonate, benzenesulfonate, p-toluenesulfonate or the like.

The compounds having the general formulae (I), (Ia), (Ib), (Ic) and (Id) of the present invention have an asymmetric carbon atom in their structures, and can exist as optical isomers due to such asymmetric carbon atom. In the present invention, a single optical isomer and mixtures of optical isomers are represented as a single chemical formula (I), (Ia), (Ib), (Ic) or (Id), individually. The present invention encompasses both individual optical isomers and mixtures thereof in any ratio. In the compounds having the general formulae (I), (Ia), (Ib), (Ic) and (Id) of the present invention, an amino group is substituted on the asymmetric carbon atom, and the compounds having the R-absolute configuration are particularly desirable, but the compounds containing the S-isomer are also encompassed in the present invention.

When the compounds of general formulae (I), (Ia), (Ib), (Ic) and (Id) of the present invention are allowed to stand in contact with the atmosphere or recrystallized, they may absorb water or water may attach to them to form a hydrate. Such hydrates are included in the compounds having the general formulae (I), (Ia), (Ib), (Ic) and (Id) of the present invention.

As representative compounds of the present invention having general formulae (I), (Ia), (Ic), and (Id), the compounds shown in from Table 1 to Table 3 can be listed, but the scope of the present invention should not be limited to these compounds.

The meaning of the abbreviations in the following Tables is shown below.

Ac: acetyl group
Boc: t-butoxycarbonyl group
Bzl: benzoyl group
Cbz: benzyloxycarbonyl group
cHex: cyclohexyl group
Eoc: ethoxycarbonyl group
Et: ethyl group
$Et_2CH$: dimethylmethyl group
HepCO: octanoyl group
HepO: heptyloxy group
iPr: isopropyl group
Me: methyl group
Moc: methoxycarbonyl group
Oct: octyl group Ph: phenyl group
PhOCO: phenoxycarbonyl group
Pr: propyl group
tBu: t-butyl group

TABLE 1

(Ia)

| Compound No. | R² | R³ | R⁴ | R |
|---|---|---|---|---|
| 1 | iPr | Boc | Me | Me |
| 2 | iPr | Boc | Me | Et |
| 3 | iPr | Boc | Et | Me |
| 4 | iPr | Boc | Et | Et |
| 5 | iPr | Boc | Pr | Me |
| 6 | iPr | Boc | Pr | Et |
| 7 | iPr | Cbz | Me | Me |
| 8 | iPr | Cbz | Me | Et |
| 9 | iPr | Cbz | Et | Me |
| 10 | iPr | Cbz | Et | Et |
| 11 | iPr | Cbz | Pr | Me |
| 12 | iPr | Cbz | Pr | Et |
| 13 | iPr | Moc | Me | Me |
| 14 | iPr | Moc | Me | Et |
| 15 | iPr | Moc | Et | Me |
| 16 | iPr | Moc | Et | Et |
| 17 | iPr | Moc | Pr | Me |
| 18 | iPr | Moc | Pr | Et |
| 19 | iPr | Eoc | Me | Me |
| 20 | iPr | Eoc | Me | Et |
| 21 | iPr | Eoc | Et | Me |
| 22 | iPr | Eoc | Et | Et |
| 23 | iPr | Eoc | Pr | Me |
| 24 | iPr | Eoc | Pr | Et |
| 25 | iPr | Ac | Me | Me |
| 26 | iPr | Ac | Me | Et |
| 27 | iPr | Ac | Et | Me |
| 28 | iPr | Ac | Et | Et |
| 29 | iPr | Ac | Pr | Me |
| 30 | iPr | Ac | Pr | Et |
| 31 | iPr | PhOCO | Me | Me |
| 32 | iPr | PhOCO | Me | Et |
| 33 | iPr | PhOCO | Et | Me |
| 34 | iPr | PhOCO | Et | Et |
| 35 | iPr | PhOCO | Pr | Me |
| 36 | iPr | PhOCO | Pr | Et |
| 37 | iPr | Bzl | Me | Me |
| 38 | iPr | Bzl | Me | Et |
| 39 | iPr | Bzl | Et | Me |
| 40 | iPr | Bzl | Et | Et |
| 41 | iPr | Bzl | Pr | Me |
| 42 | iPr | Bzl | Pr | Et |
| 43 | tBu | Boc | Me | Me |
| 44 | tBu | Boc | Me | Et |
| 45 | tBu | Boc | Et | Me |
| 46 | tBu | Boc | Et | Et |
| 47 | tBu | Boc | Pr | Me |
| 48 | tBu | Boc | Pr | Et |
| 49 | tBu | Cbz | Me | Me |
| 50 | tBu | Cbz | Me | Et |
| 51 | tBu | Cbz | Et | Me |
| 52 | tBu | Cbz | Et | Et |
| 53 | tBu | Cbz | Pr | Me |
| 54 | tBu | Cbz | Pr | Et |
| 55 | tBu | Moc | Me | Me |
| 56 | tBu | Moc | Me | Et |
| 57 | tBu | Moc | Et | Me |
| 58 | tBu | Moc | Et | Et |
| 59 | tBu | Moc | Pr | Me |
| 60 | tBu | Moc | Pr | Et |
| 61 | tBu | Eoc | Me | Me |
| 62 | tBu | Eoc | Me | Et |
| 63 | tBu | Eoc | Et | Me |
| 64 | tBu | Eoc | Et | Et |
| 65 | tBu | Eoc | Pr | Me |
| 66 | tBu | Eoc | Pr | Et |
| 67 | tBu | Ac | Me | Me |
| 68 | tBu | Ac | Me | Et |
| 69 | tBu | Ac | Et | Me |
| 70 | tBu | Ac | Et | Et |
| 71 | tBu | Ac | Pr | Me |
| 72 | tBu | Ac | Pr | Et |
| 73 | tBu | PhOCO | Me | Me |
| 74 | tBu | PhOCO | Me | Et |
| 75 | tBu | PhOCO | Et | Me |
| 76 | tBu | PhOCO | Et | Et |
| 77 | tBu | PhOCO | Pr | Me |
| 78 | tBu | PhOCO | Pr | Et |
| 79 | tBu | Bzl | Me | Me |
| 80 | tBu | Bzl | Me | Et |
| 81 | tBu | Bzl | Et | Me |
| 82 | tBu | Bzl | Et | Et |
| 83 | tBu | Bzl | Pr | Me |
| 84 | tBu | Bzl | Pr | Et |
| 85 | Et₂CH | Boc | Me | Me |
| 86 | Et₂CH | Boc | Me | Et |
| 87 | Et₂CH | Boc | Et | Me |
| 88 | Et₂CH | Boc | Et | Et |
| 89 | Et₂CH | Boc | Pr | Me |
| 90 | Et₂CH | Boc | Pr | Et |
| 91 | Et₂CH | Cbz | Me | Me |
| 92 | Et₂CH | Cbz | Me | Et |
| 93 | Et₂CH | Cbz | Et | Me |
| 94 | Et₂CH | Cbz | Et | Et |
| 95 | Et₂CH | Cbz | Pr | Me |
| 96 | Et₂CH | Cbz | Pr | Et |
| 97 | Et₂CH | Moc | Me | Me |
| 98 | Et₂CH | Moc | Me | Et |
| 99 | Et₂CH | Moc | Et | Me |
| 100 | Et₂CH | Moc | Et | Et |
| 101 | Et₂CH | Moc | Pr | Me |
| 102 | Et₂CH | Moc | Pr | Et |
| 103 | Et₂CH | Eoc | Me | Me |
| 104 | Et₂CH | Eoc | Me | Et |
| 105 | Et₂CH | Eoc | Et | Me |
| 106 | Et₂CH | Eoc | Et | Et |
| 107 | Et₂CH | Eoc | Pr | Me |
| 108 | Et₂CH | Eoc | Pr | Et |
| 109 | Et₂CH | Ac | Me | Me |
| 110 | Et₂CH | Ac | Me | Et |
| 111 | Et₂CH | Ac | Et | Me |
| 112 | Et₂CH | Ac | Et | Et |
| 113 | Et₂CH | Ac | Pr | Me |
| 114 | Et₂CH | Ac | Pr | Et |
| 115 | Et₂CH | PhOCO | Me | Me |
| 116 | Et₂CH | PhOCO | Me | Et |
| 117 | Et₂CH | PhOCO | Et | Me |
| 118 | Et₂CH | PhOCO | Et | Et |
| 119 | Et₂CH | PhOCO | Pr | Me |
| 120 | Et₂CH | PhOCO | Pr | Et |
| 121 | Et₂CH | Bzl | Me | Me |
| 122 | Et₂CH | Bzl | Me | Et |
| 123 | Et₂CH | Bzl | Et | Me |
| 124 | Et₂CH | Bzl | Et | Et |
| 125 | Et₂CH | Bzl | Pr | Me |
| 126 | Et₂CH | Bzl | Pr | Et |
| 127 | Ph | Boc | Me | Me |

TABLE 1-continued (Ia)

| Compound No. | R² | R³ | R⁴ | R |
|---|---|---|---|---|
| 128 | Ph | Boc | Me | Et |
| 129 | Ph | Boc | Et | Me |
| 130 | Ph | Boc | Et | Et |
| 131 | Ph | Boc | Pr | Me |
| 132 | Ph | Boc | Pr | Et |
| 133 | Ph | Cbz | Me | Me |
| 134 | Ph | Cbz | Me | Et |
| 135 | Ph | Cbz | Et | Me |
| 136 | Ph | Cbz | Et | Et |
| 137 | Ph | Cbz | Pr | Me |
| 138 | Ph | Cbz | Pr | Et |
| 139 | Ph | Moc | Me | Me |
| 140 | Ph | Moc | Me | Et |
| 141 | Ph | Moc | Et | Me |
| 142 | Ph | Moc | Et | Et |
| 143 | Ph | Moc | Pr | Me |
| 144 | Ph | Moc | Pr | Et |
| 145 | Ph | Eoc | Me | Me |
| 146 | Ph | Eoc | Me | Et |
| 147 | Ph | Eoc | Et | Me |
| 148 | Ph | Eoc | Et | Et |
| 149 | Ph | Eoc | Pr | Me |
| 150 | Ph | Eoc | Pr | Et |
| 151 | Ph | Ac | Me | Me |
| 152 | Ph | Ac | Me | Et |
| 153 | Ph | Ac | Et | Me |
| 154 | Ph | Ac | Et | Et |
| 155 | Ph | Ac | Pr | Me |
| 156 | Ph | Ac | Pr | Et |
| 157 | Ph | PhOCO | Me | Me |
| 158 | Ph | PhOCO | Me | Et |
| 159 | Ph | PhOCO | Et | Me |
| 160 | Ph | PhOCO | Et | Et |
| 161 | Ph | PhOCO | Pr | Me |
| 162 | Ph | PhOCO | Pr | Et |
| 163 | Ph | Bzl | Me | Me |
| 164 | Ph | Bzl | Me | Et |
| 165 | Ph | Bzl | Et | Me |
| 166 | Ph | Bzl | Et | Et |
| 167 | Ph | Bzl | Pr | Me |
| 168 | Ph | Bzl | Pr | Et |
| 169 | cHex | Boc | Me | Me |
| 170 | cHex | Boc | Me | Et |
| 171 | cHex | Boc | Et | Me |
| 172 | cHex | Boc | Et | Et |
| 173 | cHex | Boc | Pr | Me |
| 174 | cHex | Boc | Pr | Et |
| 175 | cHex | Cbz | Me | Me |
| 176 | cHex | Cbz | Me | Et |
| 177 | cHex | Cbz | Et | Me |
| 178 | cHex | Cbz | Et | Et |
| 179 | cHex | Cbz | Pr | Me |
| 180 | cHex | Cbz | Pr | Et |
| 181 | cHex | Moc | Me | Me |
| 182 | cHex | Moc | Me | Et |
| 183 | cHex | Moc | Et | Me |
| 184 | cHex | Moc | Et | Et |
| 185 | cHex | Moc | Pr | Me |
| 186 | cHex | Moc | Pr | Et |
| 187 | cHex | Eoc | Me | Me |
| 188 | cHex | Eoc | Me | Et |
| 189 | cHex | Eoc | Et | Me |
| 190 | cHex | Eoc | Et | Et |
| 191 | cHex | Eoc | Pr | Me |
| 192 | cHex | Eoc | Pr | Et |
| 193 | cHex | Ac | Me | Me |
| 194 | cHex | Ac | Me | Et |
| 195 | cHex | Ac | Et | Me |
| 196 | cHex | Ac | Et | Et |
| 197 | cHex | Ac | Pr | Me |
| 198 | cHex | Ac | Pr | Et |
| 199 | cHex | PhOCO | Me | Me |
| 200 | cHex | PhOCO | Me | Et |
| 201 | cHex | PhOCO | Et | Me |
| 202 | cHex | PhOCO | Et | Et |
| 203 | cHex | PhOCO | Pr | Me |
| 204 | cHex | PhOCO | Pr | Et |
| 205 | cHex | Bzl | Me | Me |
| 206 | cHex | Bzl | Me | Et |
| 207 | cHex | Bzl | Et | Me |
| 208 | cHex | Bzl | Et | Et |
| 209 | cHex | Bzl | Pr | Me |
| 210 | cHex | Bzl | Pr | Et |

Among the above compounds, preferred compounds are the compounds of Exemplification Compound Nos. 1-2, 7-8, 13-14, 19-20, 25-26, 31-32, 37-38, 43-44, 49-50, 55-56, 61-62, 67-68, 73-74, 79-80, 85-86, 91-92, 97-98, 103-104, 109-110, 115-116, 121-122, 127-128, 133-134, 139-140, 145-146, 151-152, 157-158, 163-164, 169-170, 175-176, 181-182, 187-188, 193-194, 199-200, 205-206.

More preferred compounds are the compounds of Exemplification Compound Nos. 1, 7, 13, 19, 25, 31, 37, 43, 49, 55, 61, 67, 73, 79, 85, 91, 97, 103, 109, 115, 121, 127, 133, 139, 145, 151, 157, 163, 169, 175, 181, 187, 193, 199, 205.

Even more preferred compounds are the compounds of

Exemplification compound number 43:

2-t-butyl-4-methyl-1,3-oxazolidine-3,4-dicarboxylic acid 3-t-butyl ester 4-methyl ester Exemplification compound number 49:

2-t-butyl-4-methyl-1,3-oxazolidine-3,4-dicarboxylic acid 3-benzyl ester 4-methyl ester Exemplification compound number 55:

2-t-butyl-4-methyl-1,3-oxazolidine-3,4-dicarboxylic acid dimethyl ester

Exemplification compound number 61:

2-t-butyl-4-methyl-1,3-oxazolidine-3,4-dicarboxylic acid 3-ethyl ester 4-methyl ester Exemplification compound number 67:

3-acetyl-2-t-butyl-4-methyl-1,3-oxozolidine-4-carboxylic acid methyl ester

Exemplification compound number 73:

2-t-butyl-4-methyl-1,3-oxazolidine-3,4-dicarboxylic acid 3-phenyl ester 4-methyl ester Exemplification compound number 79:

3-benzoyl-2-t-butyl-4-methyl-1,3-oxazolidine-4-carboxylic acid methyl ester.

TABLE 2

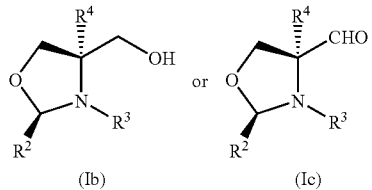

| Compound No. | R² | R³ | R⁴ |
|---|---|---|---|
| 1 | iPr | Boc | Me |
| 2 | iPr | Boc | Et |
| 3 | iPr | Boc | Pr |
| 4 | iPr | Cbz | Me |
| 5 | iPr | Cbz | Et |
| 6 | iPr | Cbz | Pr |
| 7 | iPr | Moc | Me |
| 8 | iPr | Moc | Et |
| 9 | iPr | Moc | Pr |
| 10 | iPr | Eoc | Me |
| 11 | iPr | Eoc | Et |
| 12 | iPr | Eoc | Pr |
| 13 | iPr | Ac | Me |
| 14 | iPr | Ac | Et |
| 15 | iPr | Ac | Pr |
| 16 | iPr | PhOCO | Me |
| 17 | iPr | PhOCO | Et |
| 18 | iPr | PhOCO | Pr |
| 19 | iPr | Bzl | Me |
| 20 | iPr | Bzl | Et |
| 21 | iPr | Bzl | Pr |
| 22 | tBu | Boc | Me |
| 23 | tBu | Boc | Et |
| 24 | tBu | Boc | Pr |
| 25 | tBu | Cbz | Me |
| 26 | tBu | Cbz | Et |
| 27 | tBu | Cbz | Pr |
| 28 | tBu | Moc | Me |
| 29 | tBu | Moc | Et |
| 30 | tBu | Moc | Pr |
| 31 | tBu | Eoc | Me |
| 32 | tBu | Eoc | Et |
| 33 | tBu | Eoc | Pr |
| 34 | tBu | Ac | Me |
| 35 | tBu | Ac | Et |
| 36 | tBu | Ac | Pr |
| 37 | tBu | PhOCO | Me |
| 38 | tBu | PhOCO | Et |
| 39 | tBu | PhOCO | Pr |
| 40 | tBu | Bzl | Me |
| 41 | tBu | Bzl | Et |
| 42 | tBu | Bzl | Pr |
| 43 | Et₂CH | Boc | Me |
| 44 | Et₂CH | Boc | Et |
| 45 | Et₂CH | Boc | Pr |
| 46 | Et₂CH | Cbz | Me |
| 47 | Et₂CH | Cbz | Et |
| 48 | Et₂CH | Cbz | Pr |
| 49 | Et₂CH | Moc | Me |
| 50 | Et₂CH | Moc | Et |
| 51 | Et₂CH | Moc | Pr |
| 52 | Et₂CH | Eoc | Me |
| 53 | Et₂CH | Eoc | Et |
| 54 | Et₂CH | Eoc | Pr |
| 55 | Et₂CH | Ac | Me |
| 56 | Et₂CH | Ac | Et |
| 57 | Et₂CH | Ac | Pr |
| 58 | Et₂CH | PhOCO | Me |
| 59 | Et₂CH | PhOCO | Et |
| 60 | Et₂CH | PhOCO | Pr |
| 61 | Et₂CH | Bzl | Me |
| 62 | Et₂CH | Bzl | Et |
| 63 | Et₂CH | Bzl | Pr |
| 64 | Ph | Boc | Me |
| 65 | Ph | Boc | Et |
| 66 | Ph | Boc | Pr |

TABLE 2-continued

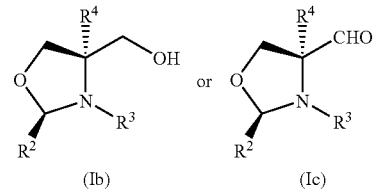

| Compound No. | R² | R³ | R⁴ |
|---|---|---|---|
| 67 | Ph | Cbz | Me |
| 68 | Ph | Cbz | Et |
| 69 | Ph | Cbz | Pr |
| 70 | Ph | Moc | Me |
| 71 | Ph | Moc | Et |
| 72 | Ph | Moc | Pr |
| 73 | Ph | Boc | Me |
| 74 | Ph | Boc | Et |
| 75 | Ph | Boc | Pr |
| 76 | Ph | Ac | Me |
| 77 | Ph | Ac | Et |
| 78 | Ph | Ac | Pr |
| 79 | Ph | PhOCO | Me |
| 80 | Ph | PhOCO | Et |
| 81 | Ph | PhOCO | Pr |
| 82 | Ph | Bzl | Me |
| 83 | Ph | Bzl | Et |
| 84 | Ph | Bzl | Pr |
| 85 | cHex | Boc | Me |
| 86 | cHex | Boc | Et |
| 87 | cHex | Boc | Pr |
| 88 | cHex | Cbz | Me |
| 89 | cHex | Cbz | Et |
| 90 | cHex | Cbz | Pr |
| 91 | cHex | Moc | Me |
| 92 | cHex | Moc | Et |
| 93 | cHex | Moc | Pr |
| 94 | cHex | Eoc | Me |
| 95 | cHex | Eoc | Et |
| 96 | cHex | Eoc | Pr |
| 97 | cHex | Ac | Me |
| 98 | cHex | Ac | Et |
| 99 | cHex | Ac | Pr |
| 100 | cHex | PhOCO | Me |
| 101 | cHex | PhOCO | Et |
| 102 | cHex | PhOCO | Pr |
| 103 | cHex | Bzl | Me |
| 104 | cHex | Bzl | Et |
| 105 | cHex | Bzl | Pr |

Among the above compounds, preferred compounds are the compounds of Exemplification Compound Nos. 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, and 103.

More preferred compounds are the compounds of Exemplification Compound Nos. 1, 4, 7, 10, 13, 16, 19, 22, 25, 28, 31, 34, 37, 40, 43, 46, 49, 52, 55, 58, and 61.

Even more preferred compounds as the compound of (Ib) of the present invention are the compounds of Exemplification compound number 22:
2-t-butyl-4-hydroxymethyl-4-methyl-1,3-oxazolidine-3-carboxylic acid t-butyl ester,
Exemplification compound number 25:
2-t-butyl-4-hydroxymethyl-4-methyl-1,3-oxazolidine-3-carboxylic acid benzyl ester,
Exemplification compound number 28:
2-t-butyl-4-hydroxymethyl-4-methyl-1,3-oxazolidine-3-carboxylic acid methyl ester,
Exemplification compound number 31:
2-t-butyl-4-hydroxymethyl-4-methyl-1,3-oxazolidine-3-carboxylic acid ethyl ester, Exemplification compound number 34:
(3-acetyl-2-t-butyl-4-methyl-1,3-oxazolidin-4-yl)methanol,
Exemplification compound number 37:
2-t-butyl-4-hydroxymethyl-4-methyl-1,3-oxazolidine-3-carboxylic acid phenyl ester,
Exemplification compound number 40:
(3-benzoyl-2-t-butyl-4-methyl-1,3-oxazolidin-4-yl)methanol, as the compound of (Ic) of the present invention are the compounds of
Exemplification compound number 22:
2-t-butyl-4-formyl-4-methyl-1,3-oxazolidine-3-carboxylic acid t-butyl ester,
Exemplification compound number 25:
2-t-butyl-4-formyl-4-methyl-1,3-oxazolidine-3-carboxylic acid benzyl ester,
Exemplification compound number 28:
2-t-butyl-4-formyl-4-methyl-1,3-oxazolidine-3-carboxylic acid methyl ester,
Exemplification compound number 31:
2-t-butyl-4-formyl-4-methyl-1,3-oxazolidine-3-carboxylic acid ethyl ester,
Exemplification compound number 34:
3-acetyl-2-t-butyl-4-methyl-1,3-oxazolidine-4-carboaldehyde,
Exemplification compound number 37:
2-t-butyl-4-formyl-4-methyl-1,3-oxazolidine-3-carboxylic acid phenyl ester, and
Exemplification compound number 40:
3-benzoyl-2-t-butyl-4-methyl-1,3-oxazolidine-4-carboaldehyde.

TABLE 3

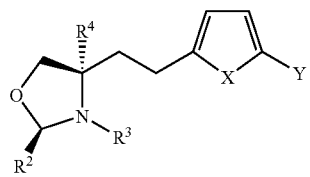

(Id)

| Compound No. | $R^2$ | $R^3$ | $R^4$ | X | Y |
|---|---|---|---|---|---|
| 1 | iPr | Boc | Me | MeN | H |
| 2 | iPr | Boc | Me | MeN | Cl |
| 3 | iPr | Boc | Me | MeN | Br |
| 4 | iPr | Boc | Me | MeN | Oct |
| 5 | iPr | Boc | Me | MeN | HepO |
| 6 | iPr | Boc | Me | MeN | HepCO |
| 7 | iPr | Boc | Me | CHCH | Cl |
| 8 | iPr | Boc | Me | CHCH | Br |
| 9 | iPr | Boc | Me | CHCH | I |
| 10 | iPr | Boc | Me | CHCH | Oct |
| 11 | iPr | Boc | Me | CHCH | HepO |
| 12 | iPr | Boc | Me | CHCH | HepCO |
| 13 | iPr | Boc | Et | MeN | H |
| 14 | iPr | Boc | Et | MeN | Cl |
| 15 | iPr | Boc | Et | MeN | Br |
| 16 | iPr | Boc | Et | MeN | Oct |
| 17 | iPr | Boc | Et | MeN | HepO |
| 18 | iPr | Boc | Et | MeN | HepCO |
| 19 | iPr | Boc | Et | CHCH | Cl |
| 20 | iPr | Boc | Et | CHCH | Br |
| 21 | iPr | Boc | Et | CHCH | I |
| 22 | iPr | Boc | Et | CHCH | Oct |
| 23 | iPr | Boc | Et | CHCH | HepO |
| 24 | iPr | Boc | Et | CHCH | HepCO |
| 25 | iPr | Moc | Me | MeN | H |
| 26 | iPr | Moc | Me | MeN | Cl |
| 27 | iPr | Moc | Me | MeN | Br |
| 28 | iPr | Moc | Me | MeN | Oct |
| 29 | iPr | Moc | Me | MeN | HepO |
| 30 | iPr | Moc | Me | MeN | HepCO |
| 31 | iPr | Moc | Me | CHCH | Cl |
| 32 | iPr | Moc | Me | CHCH | Br |
| 33 | iPr | Moc | Me | CHCH | I |
| 34 | iPr | Moc | Me | CHCH | Oct |
| 35 | iPr | Moc | Me | CHCH | HepO |
| 36 | iPr | Moc | Me | CHCH | HepCO |
| 37 | iPr | Moc | Et | MeN | H |
| 38 | iPr | Moc | Et | MeN | Cl |
| 39 | iPr | Moc | Et | MeN | Br |
| 40 | iPr | Moc | Et | MeN | Oct |
| 41 | iPr | Moc | Et | MeN | HepO |
| 42 | iPr | Moc | Et | MeN | HepCO |
| 43 | iPr | Moc | Et | CHCH | Cl |
| 44 | iPr | Moc | Et | CHCH | Br |
| 45 | iPr | Moc | Et | CHCH | I |
| 46 | iPr | Moc | Et | CHCH | Oct |
| 47 | iPr | Moc | Et | CHCH | HepO |
| 48 | iPr | Moc | Et | CHCH | HepCO |
| 49 | iPr | PhOCO | Me | MeN | H |
| 50 | iPr | PhOCO | Me | MeN | Cl |
| 51 | iPr | PhOCO | Me | MeN | Br |
| 52 | iPr | PhOCO | Me | MeN | Oct |
| 53 | iPr | PhOCO | Me | MeN | HepO |
| 54 | iPr | PhOCO | Me | MeN | HepCO |
| 55 | iPr | PhOCO | Me | CHCH | Cl |
| 56 | iPr | PhOCO | Me | CHCH | Br |
| 57 | iPr | PhOCO | Me | CHCH | I |
| 58 | iPr | PhOCO | Me | CHCH | Oct |
| 59 | iPr | PhOCO | Me | CHCH | HepO |
| 60 | iPr | PhOCO | Me | CHCH | HepCO |
| 61 | iPr | PhOCO | Et | MeN | H |
| 62 | iPr | PhOCO | Et | MeN | Cl |
| 63 | iPr | PhOCO | Et | MeN | Br |
| 64 | iPr | PhOCO | Et | MeN | Oct |
| 65 | iPr | PhOCO | Et | MeN | HepO |
| 66 | iPr | PhOCO | Et | MeN | HepCO |
| 67 | iPr | PhOCO | Et | CHCH | Cl |
| 68 | iPr | PhOCO | Et | CHCH | Br |
| 69 | iPr | PhOCO | Et | CHCH | I |
| 70 | iPr | PhOCO | Et | CHCH | Oct |
| 71 | iPr | PhOCO | Et | CHCH | HepO |
| 72 | iPr | PhOCO | Et | CHCH | HepCO |
| 73 | tBu | Boc | Me | MeN | H |
| 74 | tBu | Boc | Me | MeN | Cl |
| 75 | tBu | Boc | Me | MeN | Br |
| 76 | tBu | Boc | Me | MeN | Oct |
| 77 | tBu | Boc | Me | MeN | HepO |
| 78 | tBu | Boc | Me | MeN | HepCO |
| 79 | tBu | Boc | Me | CHCH | Cl |
| 80 | tBu | Boc | Me | CHCH | Br |
| 81 | tBu | Boc | Me | CHCH | I |
| 82 | tBu | Boc | Me | CHCH | Oct |
| 83 | tBu | Boc | Me | CHCH | HepO |
| 84 | tBu | Boc | Me | CHCH | HepCO |
| 85 | tBu | Boc | Et | MeN | H |
| 86 | tBu | Boc | Et | MeN | Cl |
| 87 | tBu | Boc | Et | MeN | Br |
| 88 | tBu | Boc | Et | MeN | Oct |
| 89 | tBu | Boc | Et | MeN | HepO |
| 90 | tBu | Boc | Et | MeN | HepCO |
| 91 | tBu | Boc | Et | CHCH | Cl |
| 92 | tBu | Boc | Et | CHCH | Br |

TABLE 3-continued

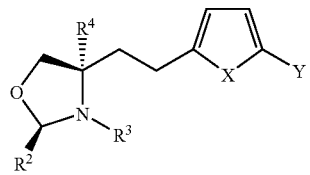

(Id)

TABLE 3-continued (Id)

| Compound No. | R² | R³ | R⁴ | X | Y |
|---|---|---|---|---|---|
| 93 | tBu | Boc | Et | CHCH | I |
| 94 | tBu | Boc | Et | CHCH | Oct |
| 95 | tBu | Boc | Et | CHCH | HepO |
| 96 | tBu | Boc | Et | CHCH | HepCO |
| 97 | tBu | Cbz | Me | MeN | H |
| 98 | tBu | Cbz | Me | MeN | Cl |
| 99 | tBu | Cbz | Me | MeN | Br |
| 100 | tBu | Cbz | Me | MeN | Oct |
| 101 | tBu | Cbz | Me | MeN | HepO |
| 102 | tBu | Cbz | Me | MeN | HepCO |
| 103 | tBu | Cbz | Me | CHCH | Cl |
| 104 | tBu | Cbz | Me | CHCH | Br |
| 105 | tBu | Cbz | Me | CHCH | I |
| 106 | tBu | Cbz | Me | CHCH | Oct |
| 107 | tBu | Cbz | Me | CHCH | HepO |
| 108 | tBu | Cbz | Me | CHCH | HepCO |
| 109 | tBu | Cbz | Et | MeN | H |
| 110 | tBu | Cbz | Et | MeN | Cl |
| 111 | tBu | Cbz | Et | MeN | Br |
| 112 | tBu | Cbz | Et | MeN | Oct |
| 113 | tBu | Cbz | Et | MeN | HepO |
| 114 | tBu | Cbz | Et | MeN | HepCO |
| 115 | tBu | Cbz | Et | CHCH | Cl |
| 116 | tBu | Cbz | Et | CHCH | Br |
| 117 | tBu | Cbz | Et | CHCH | I |
| 118 | tBu | Cbz | Et | CHCH | Oct |
| 119 | tBu | Cbz | Et | CHCH | HepO |
| 120 | tBu | Cbz | Et | CHCH | HepCO |
| 121 | tBu | Moc | Me | MeN | H |
| 122 | tBu | Moc | Me | MeN | Cl |
| 123 | tBu | Moc | Me | MeN | Br |
| 124 | tBu | Moc | Me | MeN | Oct |
| 125 | tBu | Moc | Me | MeN | HepO |
| 126 | tBu | Moc | Me | MeN | HepCO |
| 127 | tBu | Moc | Me | CHCH | Cl |
| 128 | tBu | Moc | Me | CHCH | Br |
| 129 | tBu | Moc | Me | CHCH | I |
| 130 | tBu | Moc | Me | CHCH | Oct |
| 131 | tBu | Moc | Me | CHCH | HepO |
| 132 | tBu | Moc | Me | CHCH | HepCO |
| 133 | tBu | Moc | Et | MeN | H |
| 134 | tBu | Moc | Et | MeN | Cl |
| 135 | tBu | Moc | Et | MeN | Br |
| 136 | tBu | Moc | Et | MeN | Oct |
| 137 | tBu | Moc | Et | MeN | HepO |
| 138 | tBu | Moc | Et | MeN | HepCO |
| 139 | tBu | Moc | Et | CHCH | Cl |
| 140 | tBu | Moc | Et | CHCH | Br |
| 141 | tBu | Moc | Et | CHCH | I |
| 142 | tBu | Moc | Et | CHCH | Oct |
| 143 | tBu | Moc | Et | CHCH | HepO |
| 144 | tBu | Moc | Et | CHCH | HepCO |
| 145 | tBu | Eoc | Me | MeN | H |
| 146 | tBu | Eoc | Me | MeN | Cl |
| 147 | tBu | Eoc | Me | MeN | Br |
| 148 | tBu | Eoc | Me | MeN | Oct |
| 149 | tBu | Eoc | Me | MeN | HepO |
| 150 | tBu | Eoc | Me | MeN | HepCO |
| 151 | tBu | Eoc | Me | CHCH | Cl |
| 152 | tBu | Eoc | Me | CHCH | Br |
| 153 | tBu | Eoc | Me | CHCH | I |
| 154 | tBu | Eoc | Me | CHCH | Oct |
| 155 | tBu | Eoc | Me | CHCH | HepO |
| 156 | tBu | Eoc | Me | CHCH | HepCO |
| 157 | tBu | Eoc | Et | MeN | H |
| 158 | tBu | Eoc | Et | MeN | Cl |
| 159 | tBu | Eoc | Et | MeN | Br |
| 160 | tBu | Eoc | Et | MeN | Oct |
| 161 | tBu | Eoc | Et | MeN | HepO |
| 162 | tBu | Eoc | Et | MeN | HepCO |
| 163 | tBu | Eoc | Et | CHCH | Cl |
| 164 | tBu | Eoc | Et | CHCH | Br |
| 165 | tBu | Eoc | Et | CHCH | I |
| 166 | tBu | Eoc | Et | CHCH | Oct |
| 167 | tBu | Eoc | Et | CHCH | HepO |
| 168 | tBu | Eoc | Et | CHCH | HepCO |
| 169 | tBu | PhOCO | Me | MeN | H |
| 170 | tBu | PhOCO | Me | MeN | Cl |
| 171 | tBu | PhOCO | Me | MeN | Br |
| 172 | tBu | PhOCO | Me | MeN | Oct |
| 173 | tBu | PhOCO | Me | MeN | HepO |
| 174 | tBu | PhOCO | Me | MeN | HepCO |
| 175 | tBu | PhOCO | Me | CHCH | Cl |
| 176 | tBu | PhOCO | Me | CHCH | Br |
| 177 | tBu | PhOCO | Me | CHCH | I |
| 178 | tBu | PhOCO | Me | CHCH | Oct |
| 179 | tBu | PhOCO | Me | CHCH | HepO |
| 180 | tBu | PhOCO | Me | CHCH | HepCO |
| 181 | tBu | PhOCO | Et | MeN | H |
| 182 | tBu | PhOCO | Et | MeN | Cl |
| 183 | tBu | PhOCO | Et | MeN | Br |
| 184 | tBu | PhOCO | Et | MeN | Oct |
| 185 | tBu | PhOCO | Et | MeN | HepO |
| 186 | tBu | PhOCO | Et | MeN | HepCO |
| 187 | tBu | PhOCO | Et | CHCH | Cl |
| 188 | tBu | PhOCO | Et | CHCH | Br |
| 189 | tBu | PhOCO | Et | CHCH | I |
| 190 | tBu | PhOCO | Et | CHCH | Oct |
| 191 | tBu | PhOCO | Et | CHCH | HepO |
| 192 | tBu | PhOCO | Et | CHCH | HepCO |
| 193 | tBu | Ac | Me | MeN | H |
| 194 | tBu | Ac | Me | MeN | Cl |
| 195 | tBu | Ac | Me | MeN | Br |
| 196 | tBu | Ac | Me | MeN | Oct |
| 197 | tBu | Ac | Me | MeN | HepO |
| 198 | tBu | Ac | Me | MeN | HepCO |
| 199 | tBu | Ac | Me | CHCH | Cl |
| 200 | tBu | Ac | Me | CHCH | Br |
| 201 | tBu | Ac | Me | CHCH | I |
| 202 | tBu | Ac | Me | CHCH | Oct |
| 203 | tBu | Ac | Me | CHCH | HepO |
| 204 | tBu | Ac | Me | CHCH | HepCO |
| 205 | tBu | Ac | Et | MeN | H |
| 206 | tBu | Ac | Et | MeN | Cl |
| 207 | tBu | Ac | Et | MeN | Br |
| 208 | tBu | Ac | Et | MeN | Oct |
| 209 | tBu | Ac | Et | MeN | HepO |
| 210 | tBu | Ac | Et | MeN | HepCO |
| 211 | tBu | Ac | Et | CHCH | Cl |
| 212 | tBu | Ac | Et | CHCH | Br |
| 213 | tBu | Ac | Et | CHCH | I |
| 214 | tBu | Ac | Et | CHCH | Oct |
| 215 | tBu | Ac | Et | CHCH | HepO |
| 216 | tBu | Ac | Et | CHCH | HepCO |
| 217 | tBu | Bzl | Me | MeN | H |
| 218 | tBu | Bzl | Me | MeN | Cl |
| 219 | tBu | Bzl | Me | MeN | Br |
| 220 | tBu | Bzl | Me | MeN | Oct |
| 221 | tBu | Bzl | Me | MeN | HepO |
| 222 | tBu | Bzl | Me | MeN | HepCO |
| 223 | tBu | Bzl | Me | CHCH | Cl |
| 224 | tBu | Bzl | Me | CHCH | Br |

TABLE 3-continued (Id)

| Compound No. | R² | R³ | R⁴ | X | Y |
|---|---|---|---|---|---|
| 225 | tBu | Bzl | Me | CHCH | I |
| 226 | tBu | Bzl | Me | CHCH | Oct |
| 227 | tBu | Bzl | Me | CHCH | HepO |
| 228 | tBu | Bzl | Me | CHCH | HepCO |
| 229 | tBu | Bzl | Et | MeN | H |
| 230 | tBu | Bzl | Et | MeN | Cl |
| 231 | tBu | Bzl | Et | MeN | Br |
| 232 | tBu | Bzl | Et | MeN | Oct |
| 233 | tBu | Bzl | Et | MeN | HepO |
| 234 | tBu | Bzl | Et | MeN | HepCO |
| 235 | tBu | Bzl | Et | CHCH | Cl |
| 236 | tBu | Bzl | Et | CHCH | Br |
| 237 | tBu | Bzl | Et | CHCH | I |
| 238 | tBu | Bzl | Et | CHCH | Oct |
| 239 | tBu | Bzl | Et | CHCH | HepO |
| 240 | tBu | Bzl | Et | CHCH | HepCO |
| 241 | Et₂CH | Boc | Me | MeN | H |
| 242 | Et₂CH | Boc | Me | MeN | Cl |
| 243 | Et₂CH | Boc | Me | MeN | Br |
| 244 | Et₂CH | Boc | Me | MeN | Oct |
| 245 | Et₂CH | Boc | Me | MeN | HepO |
| 246 | Et₂CH | Boc | Me | MeN | HepCO |
| 247 | Et₂CH | Boc | Me | CHCH | Cl |
| 248 | Et₂CH | Boc | Me | CHCH | Br |
| 249 | Et₂CH | Boc | Me | CHCH | I |
| 250 | Et₂CH | Boc | Me | CHCH | Oct |
| 251 | Et₂CH | Boc | Me | CHCH | HepO |
| 252 | Et₂CH | Boc | Me | CHCH | HepCO |
| 253 | Et₂CH | Boc | Et | MeN | H |
| 254 | Et₂CH | Boc | Et | MeN | Cl |
| 255 | Et₂CH | Boc | Et | MeN | Br |
| 256 | Et₂CH | Boc | Et | MeN | Oct |
| 257 | Et₂CH | Boc | Et | MeN | HepO |
| 258 | Et₂CH | Boc | Et | MeN | HepCO |
| 259 | Et₂CH | Boc | Et | CHCH | Cl |
| 260 | Et₂CH | Boc | Et | CHCH | Br |
| 261 | Et₂CH | Boc | Et | CHCH | I |
| 262 | Et₂CH | Boc | Et | CHCH | Oct |
| 263 | Et₂CH | Boc | Et | CHCH | HepO |
| 264 | Et₂CH | Boc | Et | CHCH | HepCO |
| 265 | Et₂CH | Moc | Me | MeN | H |
| 266 | Et₂CH | Moc | Me | MeN | Cl |
| 267 | Et₂CH | Moc | Me | MeN | Br |
| 268 | Et₂CH | Moc | Me | MeN | Oct |
| 269 | Et₂CH | Moc | Me | MeN | HepO |
| 270 | Et₂CH | Moc | Me | MeN | HepCO |
| 271 | Et₂CH | Moc | Me | CHCH | Cl |
| 272 | Et₂CH | Moc | Me | CHCH | Br |
| 273 | Et₂CH | Moc | Me | CHCH | I |
| 274 | Et₂CH | Moc | Me | CHCH | Oct |
| 275 | Et₂CH | Moc | Me | CHCH | HepO |
| 276 | Et₂CH | Moc | Me | CHCH | HepCO |
| 277 | Et₂CH | Moc | Et | MeN | H |
| 278 | Et₂CH | Moc | Et | MeN | Cl |
| 279 | Et₂CH | Moc | Et | MeN | B |
| 280 | Et₂CH | Moc | Et | MeN | Oct |
| 281 | Et₂CH | Moc | Et | MeN | HepO |
| 282 | Et₂CH | Moc | Et | MeN | HepCO |
| 283 | Et₂CH | Moc | Et | CHCH | Cl |
| 284 | Et₂CH | Moc | Et | CHCH | Br |
| 285 | Et₂CH | Moc | Et | CHCH | I |
| 286 | Et₂CH | Moc | Et | CHCH | Oct |
| 287 | Et₂CH | Moc | Et | CHCH | HepO |
| 288 | Et₂CH | Moc | Et | CHCH | HepCO |
| 289 | Et₂CH | PhOCO | Me | MeN | H |
| 290 | Et₂CH | PhOCO | Me | MeN | Cl |
| 291 | Et₂CH | PhOCO | Me | MeN | Br |
| 292 | Et₂CH | PhOCO | Me | MeN | Oct |
| 293 | Et₂CH | PhOCO | Me | MeN | HepO |
| 294 | Et₂CH | PhOCO | Me | MeN | HepCO |
| 295 | Et₂CH | PhOCO | Me | CHCH | Cl |
| 296 | Et₂CH | PhOCO | Me | CHCH | Br |
| 297 | Et₂CH | PhOCO | Me | CHCH | I |
| 298 | Et₂CH | PhOCO | Me | CHCH | Oct |
| 299 | Et₂CH | PhOCO | Me | CHCH | HepO |
| 300 | Et₂CH | PhOCO | Me | CHCH | HepCO |
| 301 | Et₂CH | PhOCO | Et | MeN | H |
| 302 | Et₂CH | PhOCO | Et | MeN | Cl |
| 303 | Et₂CH | PhOCO | Et | MeN | Br |
| 304 | Et₂CH | PhOCO | Et | MeN | Oct |
| 305 | Et₂CH | PhOCO | Et | MeN | HepO |
| 306 | Et₂CH | PhOCO | Et | MeN | HepCO |
| 307 | Et₂CH | PhOCO | Et | CHCH | Cl |
| 308 | Et₂CH | PhOCO | Et | CHCH | Br |
| 309 | Et₂CH | PhOCO | Et | CHCH | I |
| 310 | Et₂CH | PhOCO | Et | CHCH | Oct |
| 311 | Et₂CH | PhOCO | Et | CHCH | HepO |
| 312 | Et₂CH | PhOCO | Et | CHCH | HepCO |
| 313 | Ph | Boc | Me | MeN | H |
| 314 | Ph | Boc | Me | MeN | Cl |
| 315 | Ph | Boc | Me | MeN | Br |
| 316 | Ph | Boc | Me | MeN | Oct |
| 317 | Ph | Boc | Me | MeN | HepO |
| 318 | Ph | Boc | Me | MeN | HepCO |
| 319 | Ph | Boc | Me | CHCH | Cl |
| 320 | Ph | Boc | Me | CHCH | Br |
| 321 | Ph | Boc | Me | CHCH | I |
| 322 | Ph | Boc | Me | CHCH | Oct |
| 323 | Ph | Boc | Me | CHCH | HepO |
| 324 | Ph | Boc | Me | CHCH | HepCO |
| 325 | Ph | Boc | Et | MeN | H |
| 326 | Ph | Boc | Et | MeN | Cl |
| 327 | Ph | Boc | Et | MeN | Br |
| 328 | Ph | Boc | Et | MeN | Oct |
| 329 | Ph | Boc | Et | MeN | HepO |
| 330 | Ph | Boc | Et | MeN | HepCO |
| 331 | Ph | Boc | Et | CHCH | Cl |
| 332 | Ph | Boc | Et | CHCH | Br |
| 333 | Ph | Boc | Et | CHCH | I |
| 334 | Ph | Boc | Et | CHCH | Oct |
| 335 | Ph | Boc | Et | CHCH | HepO |
| 336 | Ph | Boc | Et | CHCH | HepCO |
| 337 | Ph | Moc | Me | MeN | H |
| 338 | Ph | Moc | Me | MeN | Cl |
| 339 | Ph | Moc | Me | MeN | Br |
| 340 | Ph | Moc | Me | MeN | Oct |
| 341 | Ph | Moc | Me | MeN | HepO |
| 342 | Ph | Moc | Me | MeN | HepCO |
| 343 | Ph | Moc | Me | CHCH | Cl |
| 344 | Ph | Moc | Me | CHCH | Br |
| 345 | Ph | Moc | Me | CHCH | I |
| 346 | Ph | Moc | Me | CHCH | Oct |
| 347 | Ph | Moc | Me | CHCH | HepO |
| 348 | Ph | Moc | Me | CHCH | HepCO |
| 349 | Ph | Moc | Et | MeN | H |
| 350 | Ph | Moc | Et | MeN | Cl |
| 351 | Ph | Moc | Et | MeN | Br |
| 352 | Ph | Moc | Et | MeN | Oct |
| 353 | Ph | Moc | Et | MeN | HepO |
| 354 | Ph | Moc | Et | MeN | HepCO |
| 355 | Ph | Moc | Et | CHCH | Cl |
| 356 | Ph | Moc | Et | CHCH | Br |

TABLE 3-continued (Id)

| Compound No. | $R^2$ | $R^3$ | $R^4$ | X | Y |
|---|---|---|---|---|---|
| 357 | Ph | Moc | Et | CHCH | I |
| 358 | Ph | Moc | Et | CHCH | Oct |
| 359 | Ph | Moc | Et | CHCH | HepO |
| 360 | Ph | Moc | Et | CHCH | HepCO |
| 361 | Ph | PhOCO | Me | MeN | H |
| 362 | Ph | PhOCO | Me | MeN | Cl |
| 363 | Ph | PhOCO | Me | MeN | Br |
| 364 | Ph | PhOCO | Me | MeN | Oct |
| 365 | Ph | PhOCO | Me | MeN | HepO |
| 366 | Ph | PhOCO | Me | MeN | HepCO |
| 367 | Ph | PhOCO | Me | CHCH | Cl |
| 368 | Ph | PhOCO | Me | CHCH | Br |
| 369 | Ph | PhOCO | Me | CHCH | I |
| 370 | Ph | PhOCO | Me | CHCH | Oct |
| 371 | Ph | PhOCO | Me | CHCH | HepO |
| 372 | Ph | PhOCO | Me | CHCH | HepCO |
| 373 | Ph | PhOCO | Et | MeN | H |
| 374 | Ph | PhOCO | Et | MeN | Cl |
| 375 | Ph | PhOCO | Et | MeN | Br |
| 376 | Ph | PhOCO | Et | MeN | Oct |
| 377 | Ph | PhOCO | Et | MeN | HepO |
| 378 | Ph | PhOCO | Et | MeN | HepCO |
| 379 | Ph | PhOCO | Et | CHCH | Cl |
| 380 | Ph | PhOCO | Et | CHCH | Br |
| 381 | Ph | PhOCO | Et | CHCH | I |
| 382 | Ph | PhOCO | Et | CHCH | Oct |
| 383 | Ph | PhOCO | Et | CHCH | HepO |
| 384 | Ph | PhOCO | Et | CHCH | HepCO |

Among the above compounds, preferred compounds are the compounds of Exemplification Compound, Nos.:
1-6, 25-30, 49-54, 73-78, 97-102, 121-126, 145-150, 169-174, 193-198, 217-222, 241-246, 265-270, 289-294, 313-318, 337-342, and 361-366.

More preferred compounds are the compounds of Exemplification Compound Nos.:
1-3, 25-27, 49-51, 73-75, 97-99, 121-123, 145-147, 169-171, 193-195, 217-219, 241-243, 265-267, 289-291, 313-315, 337-339, and 361-363.

Even more preferred compounds are the compounds of Exemplification compound number 73:
2-t-butyl-4-methyl-4-[2-(1-methyl-1H-pyrrol-2-yl)ethyl]-1, 3-oxazolidine-3-carboxylic acid t-butyl ester, Exemplification compound number 97:
2-t-butyl-4-methyl-4-[2-(1-methyl-1H-pyrrol-2-yl)ethyl]-1, 3-oxazolidine-3-carboxylic acid benzyl ester, Exemplification compound number 121:
2-t-butyl-4-methyl-4-[2-(1-methyl-1H-pyrrol-2-yl)ethyl]-1, 3-oxazolidine-3-carboxylic acid methyl ester, Exemplification compound number 145:
2-t-butyl-4-methyl-4-[2-(1-methyl-1H-pyrrol-2-yl)ethyl]-1, 3-oxazolidine-3-carboxylic acid ethyl ester, Exemplification compound number 169:
2-t-butyl-4-methyl-4-[2-(1-methyl-1H-pyrrol-2-yl)ethyl]-1, 3-oxazolidine-3-carboxylic acid phenyl ester, Exemplification compound number 193:
3-acetyl-2-t-butyl-4-methyl-4-[2-(1-methyl-1H-pyrrol-2-yl) ethyl]-1,3-oxozalidine, and Exemplification compound number 217:
3-benzoyl-2-t-butyl-4-methyl-4-[2-(1-methyl-1H-pyrrol-2-yl)ethyl]-1,3-oxazolidine.

Advantage of the Invention

The present invention is useful for providing the optically active 4,4-di-substituted oxazolidine derivatives and procedures for their preparation. The preparation procedures of the present invention have excellent advantages in the following respects, compared with the prior art: 1) increase in yield, 2) improvement in stereoselectivity, 3) extremely low-temperature reaction which is unsuitable for industrial large-scale synthesis is not necessary, and 4) column-chromatographic purification of intermediates is not needed in any step of these synthetic processes.

Furthermore, the compounds having the general formula (Id), which are the optically active 4,4-di-substituted oxazolidine derivatives encompassed in the present invention, are useful as synthetic intermediates in the preparation of optically active α,α-di-substituted α-amino acid derivatives having an excellent glutamate receptor antagonistic action or optically active α,α-di-substituted α-amino alcohol derivatives having new immunosuppressive action.

As shown in the following reaction scheme, for example, the compound (VII) described in non-patent literatures 8 and 9 mentioned hereinbefore, an immunosuppressive agent having a new mode action, can be synthesized from the compounds of the general formula (Id) of the present invention [wherein, $R^2$ and $R^3$ have the same meanings as those indicated hereinbefore, $R^4$ represents a methyl group, X represent a vinylene group, and Y represents a heptyloxy group] by removing $R^2$ and $R^3$ groups, both of which are protecting groups, by treatment with an acid, a base or the like according to conventional procedures.

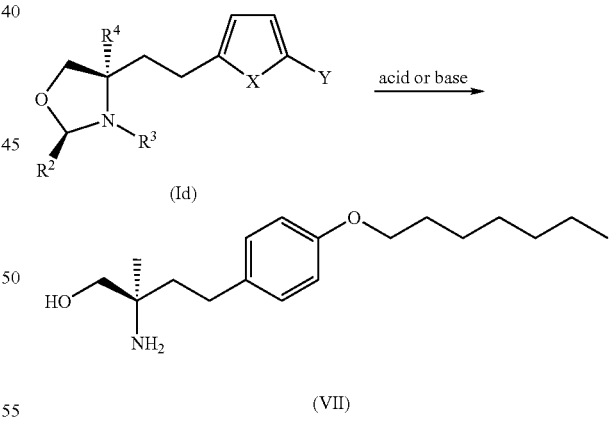

Furthermore, according to the present invention, the substituted methylenephosphonium salt which is useful as a synthetic intermediate in the preparation of the compounds having the general formula (Id) and various kinds of medicines can be obtained conveniently in a high yield.

The substituted methylenephosphonium salt having the general formula (IV'-b) or (IV'-c) prepared by the present invention is, for example, as shown in the following reaction scheme, useful as the intermediate in the preparation of immunosuppressive agents having the general formula (VI'-b) or (VI'-c) disclosed in W003/059880.

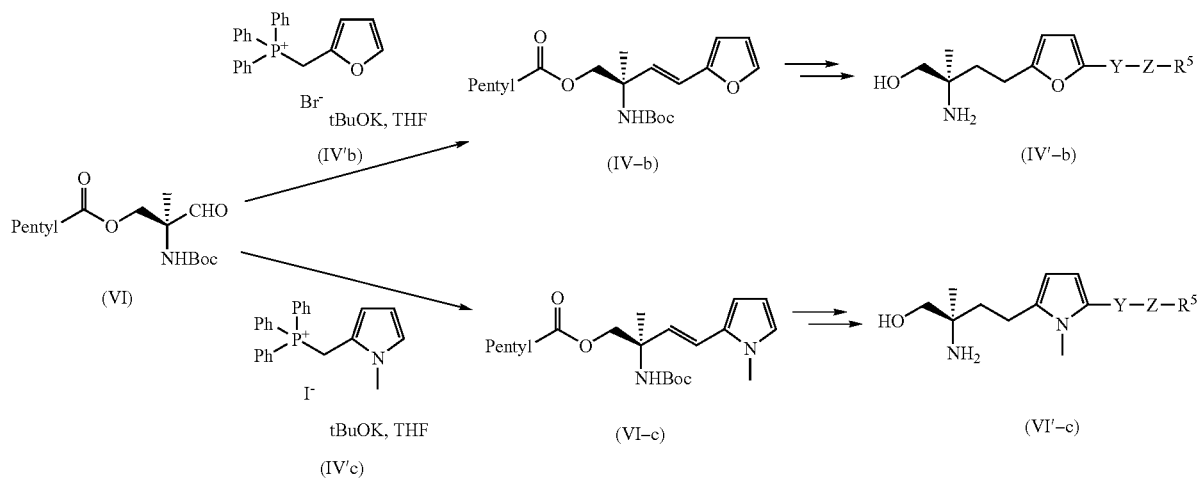

[In the above reaction scheme, Y represents an ethylene group, a vinylene group, an ethynylene group, a group of formula -E-$CH_2$— (wherein, E represents a carbonyl group, a group of formula —CH(OH)—, an oxygen atom, a sulfur atom or a group of formula —NH—), Z represents a single bond, a $C_1$-$C_{10}$ alkylene group or a $C_1$-$C_{10}$ alkylene group which has an oxygen atom or a sulfur atom in or at an end of the carbon chain, and $R^5$ represents a hydrogen atom, a cycloalkyl group, an aryl group or a heterocyclic group]

Additionally, as shown in following reaction scheme, the substituted methylenephosphonium salt having the general formula (IV'-d) prepared by the present invention is useful since the synthetic intermediate (VI-d) in the preparation of the compound having the general formula (VI'-d) disclosed in WO94/08943, which is used as an immunosuppressive agent, can be prepared by reacting this invented compound (IV'-d) with a compound having a formula (D) described in Bioorganic and Medicinal Chemistry, 11 (2003) 2529-2539.

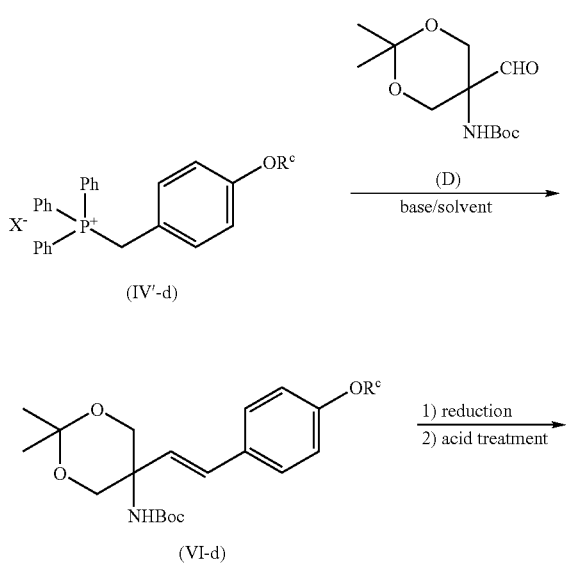

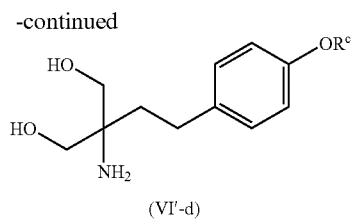

[in above reaction scheme, $R^c$ represents a $C_1$-$C_{10}$ alkyl group or the like, and X represents a halogen atom]

Best Mode for Carrying out the Invention

The compounds of the present invention can be prepared according to the procedures described below.

The compounds employed in the invented procedures are generally known compounds and can be prepared from known compounds according to known procedures, but some of them are commercially available. As the known procedures described above, there are the procedures described, for example, in "Organic Functional Group Preparation", Second Edition, Academic Press, Inc., 1989, and "Comprehensive Organic Transformations", VCH Publishers Inc., 1989.

Depending on the reactivity of functional groups, it is necessary to protect these functional groups contained in the starting materials and/or intermediates generated in the reaction processes using suitable protecting groups, that can be removed to convert the protected functional group(s) into said functional group(s) easily, before initiation of the reaction or at the suitable steps. When the functional group(s) are protected by the suitable protecting group(s), the desired compound can be obtained by removing the protecting group(s), if necessary.

Such functional group is, for example, a hydroxyl group, a carboxyl group, a hydroxyl group, a carbonyl group and an amino group, and the protecting groups are found in Green and Wuts: "Protective Groups in Organic Synthesis", 3rd edition, John Willey and Sons, Inc., 1999, and a suitable protecting group for them can be used depending on the reaction conditions.

The protecting group employed for the carboxyl group is, for example, a $C_1$-$C_6$ alkyl (for example, a methyl, ethyl, propyl, isopropyl, butyl or t-butyl group), $C_7$-$C_{10}$ aralkyl (for example, a benzyl group), phenyl, trityl, silyl (for example, a trimethylsilyl, triethylsilyl, dimethylphenylsilyl, t-butyldimethylsilyl or t-butyldiethylsilyl group), or $C_2$-$C_6$ alkenyl group (for example, a 1-allyl group). These groups may optionally be substituted with from 1 to 3 halogen atoms (for example, a fluorine, chlorine, bromine or iodine atom), a $C_1$-$C_6$ alkoxyl group (for example, a methoxy, ethoxy or propoxy group), or a nitro group.

The protecting group employed for the hydroxyl group is, for example, a $C_1$-$C_6$ alkyl (for example, a methyl, ethyl, propyl, isopropyl, butyl or t-butyl group), phenyl, trityl, $C_7$-$C_{11}$ aralkyl (for example, a benzyl group), formyl, $C_1$-$C_6$ alkylcarbonyl (for example, an acetyl or propionyl group), benzoyl, $C_7$-$C_{11}$ aralkylcarbonyl (for example, a benzylcarbonyl group), 2-tetrahydropyranyl, 2-tetrahydrofuranyl, silyl (for example, a trimethylsilyl, triethylsilyl, dimethylphenylsilyl, t-butyldimethylsilyl or t-butyldiethylsilyl group) or $C_2$-$C_6$ alkenyl group (for example, a 1-allyl group). These groups may optionally be substituted with from 1 to 3 halogen atoms (for example, a fluorine, chlorine, bromine or iodine atom), a $C_1$-$C_6$ alkyl group (for example, a methyl, ethyl or n-propyl group), a $C_1$-$C_6$ alkoxyl group (for example, a methoxy, ethoxy or propoxy group) or a nitro group.

The protecting group employed for the carbonyl group is, for example, a cyclic acetal (for example, 1,3-dioxane) or non-cyclic acetal group (for example, di-$C_1$-$C_6$ alkyl acetal group).

The protecting group employed for the amino group is, for example, a formyl, $C_1$-$C_6$ alkylcarbonyl (for example, an acetyl or propionyl group), $C_1$-$C_6$ alkoxycarbonyl (for example, a methoxycarbonyl, ethoxycarbonyl or t-butoxycarbonyl group), benzoyl, $C_7$-$C_{11}$ aralkylcarbonyl (for example, a benzylcarbonyl group), $C_7$-$C_{14}$ aralkyloxycarbonyl (for example, a benzyloxycarbonyl or 9-fluorenylmethoxycarbonyl group), trityl, phthaloyl, N,N-dimethylaminomethylene, silyl (for example, a trimethylsilyl, triethylsilyl, dimethylphenylsilyl, t-butyldimethylsilyl or t-butyldiethylsilyl group) or $C_2$-$C_6$ alkenyl group (for example, a 1-allyl group). These groups may optionally be substituted with from 1 to 3 halogen atoms (for example, a fluorine, chlorine, bromine or iodine atom), a $C_1$-$C_6$ alkoxyl group (for example, a methoxy, ethoxy or propoxy group) or a nitro group.

The removal of the protecting groups described above is carried out by known procedures such as procedures using an acid, a base, ultraviolet light, hydrazine, phenylhydrazine, sodium N-methyldithiocarbamate, tetrabutylammonium fluoride, palladium acetate or trialkylsilyl halide (for example, trimethylsilyl iodide or trimethylsilyl bromide) or a reduction procedure.

Method A

The method A is a process for the preparation of a compound having the general formula (Ia).

Method A

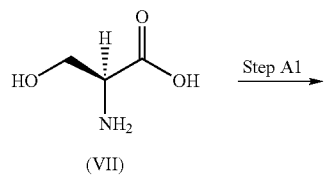

(VII)

-continued

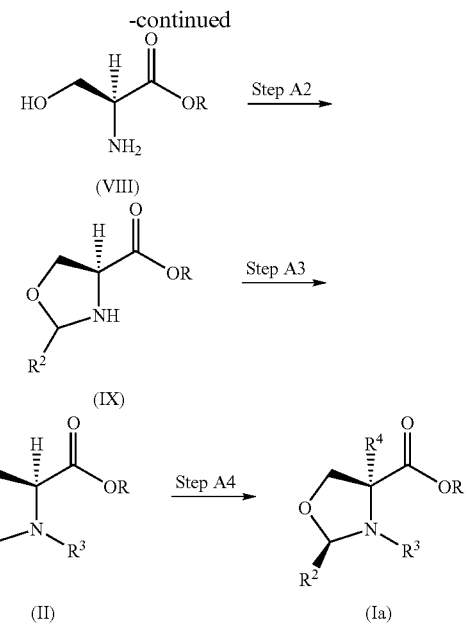

In the above reaction scheme, R, $R^2$, $R^3$ and $R^4$ have the same meanings as those indicated hereinbefore.

The compound having the general formula (II) was synthesized according to the procedure described in the literature (Angew. Chem. GE 100, 10, 1988, 1398-1404). In Step A1, the compound having the general formula (VIII) can be prepared by the esterification of (S)-serine (VII), in Step A2, the compound having the general formula (IX) can be prepared by protecting the amino alcohol compound having the general formula (VIII) obtained above with a $R^2$-acetal group, and in Step A3, a compound having the general formula (II) can be prepared by protecting the nitrogen atom of the compound having the general formula (IX) obtained above with $R^3$.

Furthermore, in Step A4 which is a reaction of the present invention, a compound having the general formula (Ia) can be prepared stereoselectively by reacting a compound having the general formula (II) with an alkylating agent in the presence of a coordinating reagent and a base and in the presence of an inert solvent or absence of a solvent. This process is a modified process of the method by Dieter Seebach et al., and is improved to enable this invented procedure to be applied to industrial large-scale manufacturing.

In the method by Dieter Seebach et al., the compound having the general formula (Ia) is synthesized by adding a base first to the compound of the general formula (II) in which R is a methyl group, $R^2$ is a t-butyl group and $R^3$ is a formyl group (this compound is different from the invented compound in respect that $R^3$ is a formyl group) and followed by addition of an alkylating agent to the resulting mixture, but the desired compound can be obtained only in the yield of about 40 to 70%. In the present invention, however, it was discovered that the compound of the general formula (Ia) can be synthesized in a high yield by addition of each reagent under reaction conditions which are appropriate to the compound of general formula (II), for example, by the addition of an alkylating reagent and a coordinating reagent to the compound of general formula (II) first and followed by the addition of a base to the resulting mixture obtained. Furthermore, in the present invention, various reaction conditions are improved, and the present invention provides several advantages in respect that the extremely low-temperature reaction (about −78° C.), which is an indispensable step in the conventional procedure and additionally unsuitable for the industrial large-scale manufacturing, can be avoided by selection of a suitable base and coordinating reagent, and a compound having the general formula (Ia) can be synthesized in a high yield even at an industrially applicable temperature, for example, at a temperature ranging from −25° C. to 10° C. In contrast to the prior art which is only the results of researches at the academic level, the present process of the present invention is superior to the prior art in respect that the invented procedure is on an industrially utilizable level.

The alkylating agent employed in the above reaction is not particularly restricted provided that it can be generally used in the alkylation of ester-enolates, and can be, for example, methyl chloride, methyl bromide, methyl iodide, methyl methanesusulfonate, methyl trifluoromethanesulfonate, methyl p-toluenesulfonate, dimethyl sulfate, ethyl chloride, ethyl bromide, ethyl iodide, ethyl methanesusulfonate, ethyl trifluoromethanesulfonate, ethyl p-toluenesulfonate, diethyl sulfate, propyl chloride, propyl bromide, propyl iodide, propyl methanesusulfonate, propyl trifluoromethanesulfonate, propyl p-toluenesulfonate or dipropyl sulfate, and is preferably methyl bromide, methyl iodide, ethyl bromide, ethyl iodide, propyl bromide or propyl iodide, and more preferably methyl bromide or methyl iodide.

The coordinating reagents employed in the above reactions can be, for example, a urea such as 1,3-dimethyl-3,4,5,6-tetrahydro-2(1H)-pyrimidinone (DMPU) or 1,3-dimethyl-2-imidazolidinone (DMI); an amide such as 1-methyl-2-pyrrolidinone (NMP), N,N-dimethylacetamide (DMAc) or N,N-dimethylformamide (DMF); a sulfoxide such as dimethyl sulfoxide (DMSO); a crown ether such as 12-crown-4, 15-crown-5 or 18-crown-6; or an ethylene glycol such as diethylene glycol dimethyl ether (diglyme), triethylene glycol dimethyl ether (triglyme), tetraethylene glycol dimethyl ether (tetraglyme) or polyethylene glycol, and is preferably DMPU, DMI, NMP, DMF, DMSO, triglyme or tetraglyme, and more preferably triglyme or tetraglyme.

The base employed in the above reaction is not particularly restricted provided that it is a low-nucleophilic base, and can be, for example, an alkali metal amide such as lithium bis(trimethylsilyl)amide (LHMDS), lithium diisopropylamide (LDA), sodium bis(trimethylsilyl)amide (SHMDS) or potassium bis(trimethylsilyl)amide (KHMDS); or an alkali-metal alkoxide such as sodium t-butoxide or potassium t-butoxide, and is preferably potassium t-butoxide.

The inert solvent employed in the above reaction is not particularly restricted provided that it has no adverse effect on the reaction, and can be, for example, an ether such as tetrahydrofuran, diethyl ether, t-butylmethyl ether, 1,4-dioxane or dimethoxyethane; an aromatic hydrocarbon such as toluene or xylene; an aliphatic hydrocarbon such as hexane or heptane; or a mixed solvent thereof, and is preferably an ether, and more preferably tetrahydrofuran or methoxyethane.

The reaction temperature employed in the above reaction is different depending on the starting material, the reagent used and the sort of solvent, but is generally between −100° C. and 30° C., preferably between −80° C. and 10° C., and most preferably between −25° C. and 10° C.

The reaction time employed in the above reaction is different depending on the reaction temperature, the starting material, the reagent and the sort of solvent employed, but is generally from 5 minutes to 24 hours, and preferably from 30 minutes to 5 hours.

After the reaction is completed, the desired compound of this reaction can be isolated from the reaction mixture by conventional treatments. The desired compound can be isolated, for example, by neutralization of the reaction mixture, if necessary, or filtration of the reaction mixture when insoluble material is present in the reaction mixture, extraction of the neutralized solution or the filtrate with an organic solvent immiscible with water such as toluene, washing the resulting organic layer with water, separation of the organic layer containing the desired compound, and then evaporation of the organic solvent under reduced pressure.

The product thus obtained, if necessary, can be further isolated and purified by conventional treatments, for example, by recrystallization or reprecipitation, or by conventional procedures generally used in the isolation and purification of organic compounds (for example, absorption column chromatography using a carrier such as silica gel, alumina or Florisil consisting of magnesium and silica gel; partition column chromatography using Sephadex LH-20 (product of Pharmacia Co., Ltd.), Amberlite XAD-11 (product of Rohm & Hass Co., Ltd.) or Diaion HP-20 (product of Mitsubishi Chemicals Co., Ltd.); ion exchange chromatography; or normal phase or reversed phase column chromatography using silica gel or alkylated silica gel, and preferably by column chromatography using silica gel).

Method B

Step B1 is a process for the preparation of a compound having the general formula (Ib).

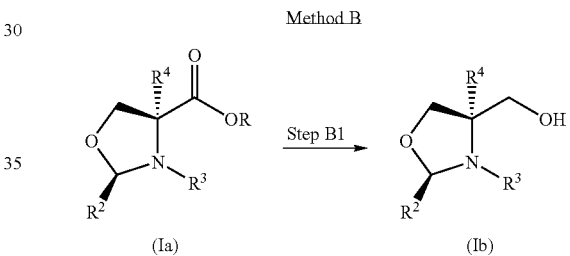

Method B (Ia) → Step B1 → (Ib)

In the above reaction scheme, R, $R^2$, $R^3$ and $R^4$ have the same meanings as those indicated hereinbefore.

A compound having the general formula (Ib) can be prepared by reacting a compound having the general formula (Ia) with a reducing agent in an inert solvent.

The reducing agent employed in the above reaction is not particularly restricted provided that it is generally used in the reduction of an ester to a primary alcohol, and can be, for example, a metal salt of borohydride such as lithium borohydride, sodium borohydride or potassium borohydride; a metal salt of aluminum hydride such as lithium aluminum hydride, sodium aluminum hydride or sodium bis(2-methoxyethoxy) aluminum hydride; or a metal hydride such as isobutylaluminum hydride, and these reducing agents described above can be also used as a combination with a lithium halogenide such as lithium chloride, lithium bromide or lithium iodide, or a lanthanide halogenide such as cerium trichloride, samarium trichloride or europium trichloride, and is preferably lithium borohydride, sodium borohydride, potassium borohydride or sodium bis(2-methoxyethoxy)aluminum hydride, or a combination of these reducing agents and a lithium halogenide, more preferably a combination of sodium borohydride or potassium borohydride and a lithium halogenide, and still more preferably a combination of potassium borohydride and lithium chloride.

The inert solvent employed in the above reaction is different depending on the sort of reagents used, but is not particularly restricted provided that it has no adverse effect on the reaction, and can be, for example, an aliphatic hydrocarbon such as hexane or heptane; an aromatic hydrocarbon such as toluene or xylene; a halogenated hydrocarbon such as dichloromethane or 1,2-dichloroethane; an ether such as tetrahydrofuran, diethyl ether or t-butyl methyl ether; an alcohol such as methanol, ethanol or n-propanol; or a mixed solvent of these solvents, and is preferably an aromatic hydrocarbon, an ether or an alcohol, or a mixed solvent of these solvents, and more preferably tetrahydrofuran or toluene, or a mixed solvent of these solvents.

The reaction temperature employed in the above reaction is different depending on the starting material, the reagent used and the sort of solvent, but is generally between −80° C. and 120° C., and preferably between −20° C. and 50° C.

The reaction time employed in the above reaction is different depending on the reaction temperature, the starting material, the reagent used and the sort of solvent employed, but is generally from 5 minutes to 48 hours, and preferably from 30 minutes to 10 hours.

After the reaction is completed, the desired compound of this reaction can be isolated from the reaction mixture and purified in the same manner as those described in the Method A.

Method C

Step C1 is a process for the preparation of a compound having the general formula (Ic).

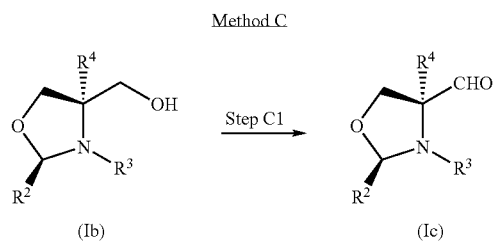

In the above reaction scheme, $R^2$, $R^3$ and $R^4$ have the same meanings as those indicated hereinbefore.

A compound having the general formula (Ic) can be prepared by reacting a compound having the general formula (Ib) with an oxidizing agent in an inert solvent.

The oxidizing agent employed in the above reaction is not particularly restricted provided that it is generally used in the oxidation of a primary alcohol to a corresponding aldehyde, and can be, for example, a chromic acid compound such as potassium chromate, chromic acid-sulfuric acid complex or chromic acid-pyridine complex; a combination of a co-oxidizing agent such as a salt of hypochlorous acid, a salt of bromous acid, N-chlorosuccinimide or molecular oxygen and a catalytic amount of 2,2,6,6-tetramethylpiperidinooxy, free radical (TEMPO) and another salt; a reagent used for DMSO oxidation (complex of dimethylsufoxide and dicyclohexylcarbodiimide, oxalyl chloride, acetic anhydride or phosphorus pentoxide, or a complex of pyridine-sulfuric anhydride); a combination of a transition metal catalyst such as a copper complex or a ruthenium complex and molecular oxygen, or a transition metal catalyst and an organic oxidizing agent such as N-methylmorpholinoxide, and is preferably a combination of a co-oxidizing agent and TEMPO and another salt, more preferably a combination of sodium hypochlorite, TEMPO, sodium bromide and sodium hydrogencarbonate.

The inert solvent employed in the above reaction is different depending on the sort of reagents used, but is not particularly restricted provided that it has no adverse effect on the reaction, and when the combination of a salt of hypochlorous acid, TEMPO and other salts is used as the oxidizing agent, the inert solvent employed can be an aliphatic hydrocarbon such as hexane or heptane; an aromatic hydrocarbon such as toluene or xylene; a halogenated hydrocarbon such as dichloromethane or 1,2-dichloroethane; an ester such as ethyl acetate or butyl acetate; or a mixed solvent of the solvents described above and water, and is preferably a mixed solvent of toluene and water.

The reaction temperature employed in the above reaction is different depending on the starting material, the reagent used and the sort of solvent, but is generally between −50° C. and 100° C., and preferably between −10° C. and 20° C.

The reaction time employed in the above reaction is different depending on the reaction temperature, the starting material, the reagent used and the sort of solvent employed, but is generally from 5 minutes to 48 hours, and preferably from 30 minutes to 5 hours.

After the reaction is completed, the desired compound of this reaction can be isolated from the reaction mixture and purified in the same manner as those described in the Method A.

Method D

Step D1 is an alternative procedure to Method C for the preparation of a compound having the general formula (Ic).

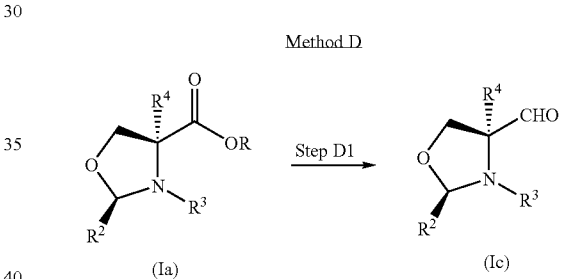

In the above reaction scheme, R, $R^2$, $R^3$ and $R^4$ have the same meanings as those indicated hereinbefore.

In this step, a compound having the general formula (Ic) can be prepared in one step by reacting a compound having the general formula (Ia) with a reducing agent in an inert solvent without passing through a compound having the general formula (Ib).

The reducing agent employed in the above reaction is not particularly restricted provided that it is generally used in a reduction reaction of an ester into an aldehyde, and can be, for example, a metal salt of borohydride such as lithium borohydride, sodium borohydride or potassium borohydride; a metal salt of aluminum hydride such as lithium aluminum hydride, sodium aluminum hydride or sodium bis(2-methoxyethoxy) aluminum hydride; or a metal hydride such as isobutylaluminum hydride, and these reducing agents described above can be also used as a combination with an organic amine such as pyrrolidine or morpholine, and is preferably sodium bis(2-methoxyethoxy)aluminum hydride or a combination thereof with an organic amine, and more preferably sodium bis(2-methoxyethoxy)aluminum hydride.

The inert solvent employed in the above reaction is not particularly restricted provided that it has no adverse effect on the reaction, and can be, for example, an aliphatic hydrocarbon such as hexane or heptane; an aromatic hydrocarbon such as toluene or xylene; or a halogenated hydrocarbon such as dichloromethane or 1,2-dichloroethane, and is preferably toluene.

The reaction temperature employed in the above reaction is different depending on the starting material, the reagent used and the sort of solvent, but is generally between −100° C. and 50° C., and preferably between −50° C. and 20° C.

The reaction time employed in the above reaction is different depending on the reaction temperature, the starting material, the reagent used and the sort of solvent employed, but is generally from 5 minutes to 48 hours, and preferably from 30 minutes to 10 hours.

After the reaction is completed, the desired compound of this reaction can be isolated from the reaction mixture and purified in the same manner as those described in the Method A.

Method E

The method E is a method for the preparation of compounds having the general formulae (Id') and (Id).

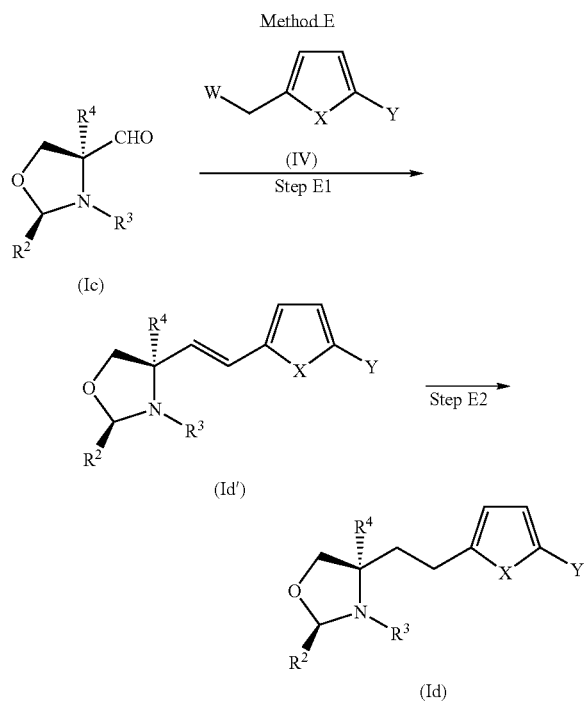

In the above reaction scheme, R, $R^2$, $R^3$, $R^4$, W, X and Y have the same meanings as those indicated hereinbefore.

Step E1 is a process for the preparation of a compound having the general formula (Id') by reacting a compound having the general formula (Ic) with a compound having the general formula (IV) in the presence of a base in an inert solvent.

The base employed in the above reaction is not particularly restricted provided that it is generally used in the Wittig reaction, and can be, for example, an alkali metal carbonate such as sodium carbonate, potassium carbonate or cesium carbonate; an alkali metal hydride such as lithium hydride or sodium hydride; an alkali metal hydroxide such as sodium hydroxide, potassium hydroxide, barium hydroxide or lithium hydroxide; an alkali metal alkoxide such as sodium methoxide, sodium ethoxide, sodium tert-butoxide or potassium tert-butoxide; an organic base such as 1,8-diazabicyclo[5.4.0]undec-7-ene; an alkyllithium such as butyllithium or an alkylmagnesium halide such as butylmagnesium bromide; an alkali metal amide such as lithium diisopropylamide, lithium bis(trimethylsilyl)amide, sodium bis(trimethylsilyl) amide or potassium bis(trimethylsilyl)amide, and is preferably an alkali metal carbonate, an alkali metal alkoxide or an alkali metal amide, and more preferably potassium carbonate, cesium carbonate, sodium methoxide, sodium ethoxide or potassium tert-butoxide.

The inert solvent employed in the above reaction is not particularly restricted provided that it has no adverse effect on the reaction, and can be, for example, an ether such as tetrahydrofuran, diethyl ether, t-butylmethyl ether; a urea such as 1,3-dimethyl-3,4,5,6-tetrahydro-2(1H)-pyrimidinone or 1,3-dimethyl-2-imidazolidinone; an amide such as 1-methyl-2-pyrrolidinone, N,N-dimethylacetamide or N,N-dimethylformamide; a sulfoxide such as dimethyl sulfoxide; or an alkylnitrile such as acetonitrile, and preferably a urea or an amide, and more preferably N,N-dimethylformamide.

The reaction temperature employed in the above reaction is different depending on the starting material, the reagent used and the sort of solvent, but is generally between −80° C. and 30° C., and preferably between −20° C. and 10° C.

The reaction time employed in the above reaction is different depending on the reaction temperature, the starting material, the reagent used and the sort of solvent employed, but is generally from 5 minutes to 48 hours, and preferably from 30 minutes to 5 hours.

After the reaction is completed, the desired compound of this reaction can be isolated from the reaction mixture and purified in the same manner as those described in the Method A.

Step E2 is a process for the preparation of a compound having the general formula (Id) by reacting a compound having the general formula (Id') with a reducing agent in an inert solvent. The reduction reaction is preferably carried out with a metal catalyst in a hydrogen atmosphere.

The metal catalyst employed in the above reaction is not particularly restricted provided that it can generally be used for catalytic reduction, and can be, for example, a heterogeneous palladium-type catalyst such as palladium-charcoal, palladium-alumina or palladium-zeolite; a nickel-type catalyst such as Raney nickel; a platinum catalyst such as platinum oxide or platinum-charcoal; a rhodium-type catalyst such as rhodium-aluminum oxide, rhodium-charcoal or triphenylphosphine-rhodium chloride; or a noble metal catalyst other than the catalysts described above such as ruthenium-charcoal, and preferably a heterogeneous palladium-type catalyst such as palladium-charcoal, palladium-alumina or palladium-zeolite.

The pressure of hydrogen employed in the above reaction is generally between 0.1 and 50 atmospheric pressures, and preferably between 1 and 10 atmospheric pressures.

The inert solvent employed in the above reaction is not particularly restricted provided that it has no adverse effect on the reaction, and can be, for example, an aliphatic hydrocarbon such as hexane or heptane; an aromatic hydrocarbon such as toluene or xylene; a halogenated hydrocarbon such as dichloromethane or 1,2-dichloroethane; an ester such as ethyl acetate or butyl acetate; an ether such as tetrahydrofuran, diethyl ether or t-butyl methyl ether; an amide such as 1-methyl-2-pyrrolidinone, N,N-dimethylformamide or N,N-dimethylacetamide; an alcohol such as methanol, ethanol or n-propanol; an organic acid such as formic acid or acetic acid; an aqueous inorganic acid solution such as aqueous hydrochloric acid solution or aqueous sulfuric acid solution; or water; or a mixed solvent of water and solvent(s) described above, and preferably an alcohol, an ether, or a mixed solvent of these solvents and water, and more preferably methanol or ethanol.

The reaction temperature employed in the above reaction is different depending on the starting material, the reagent used and the sort of solvent, but is generally between −20° C. and 100° C., and preferably between 0° C. and 50° C.

The reaction time employed in the above reaction is different depending on the reaction temperature, the starting material, the reagent used and the sort of solvent employed, but is generally from 5 minutes to 48 hours, and preferably from 30 minutes to 5 hours.

After the reaction is completed, the desired compound of this reaction can be isolated from the reaction mixture and purified in the same manner as those described in the Method A.

Method F

Method F is an alternative procedure to Method E for the preparation of a compound having the general formula (Id).

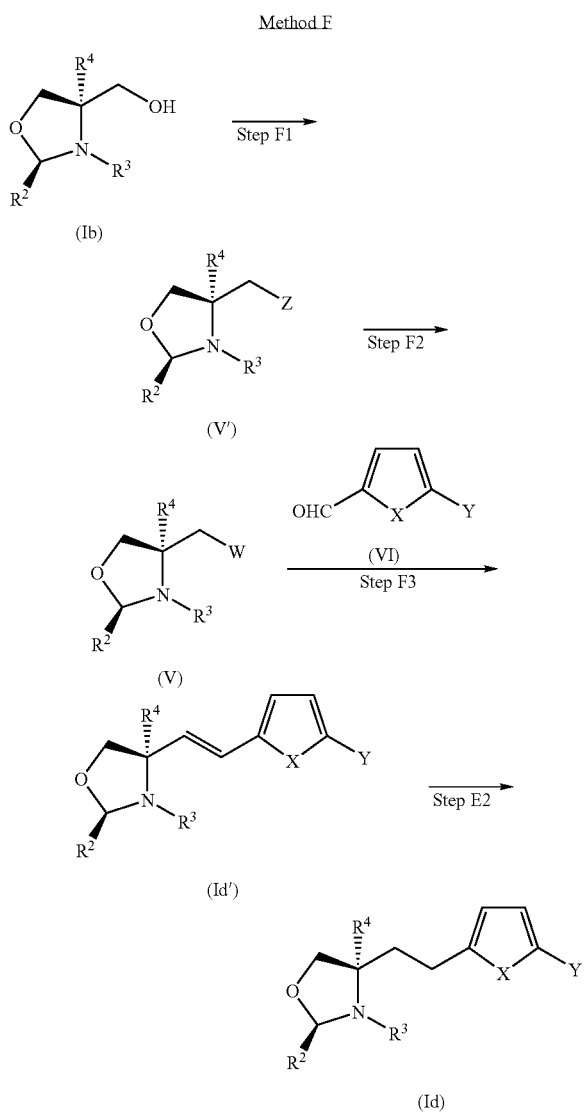

In the above reaction scheme, R, $R^2$, $R^3$, $R^4$, W, X, Y and Z have the same meanings as those indicated hereinbefore.

Step F1 is a process for the preparation of a compound having the general formula (V') and achieved by reacting a compound having the general formula (Ib) with a halogenating agent or a sulfonylating agent in the presence or absence of a base in an inert solvent.

The halogenating agent employed in the above reaction is not particularly restricted provided that it is generally used for the halogenation of a primary alcohol, and can be, for example, oxalyl chloride; a thionyl halide such as thionyl chloride or thionyl bromide; a phosphorus trihalogenide such as phosphorus trichloride or phosphorus tribromide; a phosphorus pentahalide such as phosphorus pentachloride or phosphorus pentabromide; a phosphorus oxyhalide such as phosphorus oxychloride or phosphorus oxybromide; a Vilsmeier type reagent such N,N-dimethylchloroforminium chloride or N,N-dimethylbromoforminium bromide; a combination of a phosphine such as triphenylphosphine and a halogen atom or a tetrahalogenated methane; or a combination of a phosphine such as a combination of triphenylphosphine, diethyl azodicarboxylate and lithium bromide, an azodicarboxylic acid ester and a halogenated metal, and preferably a combination of triphenylphosphine and iodine.

The sulfonylating agent employed in the above reaction is not particularly restricted provided that it is generally used for sulfonylation reaction, and can be, for example, a sulfonyl halide such as methanesulfonyl chloride or p-toluenesulfonyl chloride, or a sulfonic anhydride, and is preferably methanesulfonyl chloride or p-toluenesulfonyl chloride.

The base employed in the above reaction is different depending on the sort of reagents used, but is not particularly restricted, and can be, for example, an organic base such as imidazole, pyridine, triethylamine or N-methylimidazole, and is preferably as imidazole, pyridine or triethylamine.

The inert solvent employed in the above reaction is different depending on the sort of reagents used, but is not particularly restricted provided that it has no adverse effect on the reaction, and can be, for example, an aliphatic hydrocarbon such as hexane or heptane; an aromatic hydrocarbon such as toluene or xylene; a halogenated hydrocarbon such as dichloromethane or 1,2-dichloroethane; an ester such as ethyl acetate or butyl acetate; an ether such as tetrahydrofuran, diethyl ether or t-butyl methyl ether; or an amide such as 1-methyl-2-pyrrolidinone, N,N-dimethylformamide or N,N-dimethylacetamide, and is preferably toluene.

The reaction temperature employed in the above reaction is different depending on the starting material, the reagent used and the sort of solvent, but is generally between −20° C. and 120° C., and preferably between 0° C. and 80° C.

The reaction time employed in the above reaction is different depending on the reaction temperature, the starting material, the reagent used for the reaction and the sort of solvent employed, but is generally from 5 minutes to 48 hours, and preferably from 1 hour to 10 hours.

The compound having the general formula (V') in which Z is a halogen group can be prepared by reacting a compound having the general formula (V') in which Z is a sulfonyl group with a halogenating agent in an inert solvent.

The halogenating agent employed in the above reaction is not particularly restricted provided that it is generally used for halogenation of a compound in which a moiety of primary alcohol is sulfonylated, and can be, for example, a halogenated metal such as lithium chloride, lithium bromide, lithium bromide, sodium bromide, sodium iodide, potassium iodide, zinc chloride, zinc bromide or zinc iodide, and is preferably sodium iodide or potassium iodide.

The inert solvent employed in the above reaction is not particularly restricted provided that it has no adverse effect on the reaction, and can be, for example, an ether such as tetrahydrofuran, diethyl ether or t-butyl methyl ether; an amide such as 1-methyl-2-pyrrolidinone, N,N-dimethylformamide (DMF), or N,N-dimethylacetamide; an alcohol such as methanol, ethanol or n-propanol; or a sulfoxide such as dimethyl sulfoxide, and is preferably DMF.

The reaction temperature employed in the above reaction is different depending on the starting material, the reagent used and the sort of solvent, but is generally between −20° C. and 120° C., and preferably between 20° C. and 100° C.

The reaction time employed in the above reaction is different depending on the reaction temperature, the starting material, the reagent used for the reaction and the sort of solvent employed, but is generally from 30 minutes to 48 hours, and preferably from 1 hour to 10 hours.

After the reaction is completed, the desired compound of this reaction can be isolated from the reaction mixture and purified in the same manner as those described in the Method A.

Step F2

Step F2 is a process for the preparation of a compound having the general formula (V).

This step is achieved by reacting a compound having the general formula (V') with a phosphine or a phosphonic acid ester in an inert solvent.

The phosphine employed in the above reaction is not particularly restricted provided that it is generally used for the synthesis of a phosphonium salt, and can be, for example, trimethylphosphine, triethylphosphine, tripropylphosphine, tributylphosphine or triphenylphosphine, and is preferably triphenylphosphine.

The phosphonic acid ester employed in the above reaction is not particularly restricted provided that it is generally used for the synthesis of the phosphonic acid ester, and can be, for example, a phosphonic acid ester indicated in the above-mentioned definition, and is preferably triethyl phosphonate.

The inert solvent employed in the above reaction is not particularly restricted provided that it has no adverse effect on the reaction, and can be, for example, an aliphatic hydrocarbon such as hexane or heptane; an aromatic hydrocarbon such as toluene or xylene; a halogenated hydrocarbon such as dichloromethane or 1,2-dichloroethane; an ester such as ethyl acetate or butyl acetate; an ether such as tetrahydrofuran, diethyl ether or t-butyl methyl ether; an amide such as 1-methyl-2-pyrrolidinone, N,N-dimethylformamide (DMF) or N,N-dimethylacetamide; an alcohol such as methanol, ethanol or n-propanol; a sulfoxide such as dimethyl sulfoxide; a nitrile such as acetonitrile, but depending on the reagent employed, the above reaction can be carried out in the absence of a solvent. The preferred inert solvent is ethyl acetate, DMF or acetonitrile.

The reaction temperature employed in the above reaction is different depending on the starting material, the reagent used and the sort of solvent, but is generally between −20° C. and 120° C., and preferably between 20° C. and 100° C.

The reaction time employed in the above reaction is different depending on the reaction temperature, the starting material, the reagent used for the reaction and the sort of solvent employed, but is generally from 5 minutes to 48 hours, and preferably from 30 minutes to 10 hours.

After the reaction is completed, the desired compound of this reaction can be isolated from the reaction mixture and purified in the same manner as those described in the Method A.

Step F3

Step F3 is a process for the preparation of a compound having the general formula (Id') by reacting a compound having the general formula (V) with a compound having the general formula (VI) in the presence of a base in an inert solvent. Step F3 can be carried out in the same manner as that described in Step E1 of the method E.

The compound having the general formula (Id') obtained in Step F3 can be converted into a compound having the general formula (Id) in the same manner as that described in Step E2 of the Method E.

Method G

Method G is a process for the preparation of a compound having the general formula (IV') by reacting a compound having the general formula (IV'') or salt thereof with a compound having the general formula (A) in the presence of a compound having the general formula (B) in a solvent.

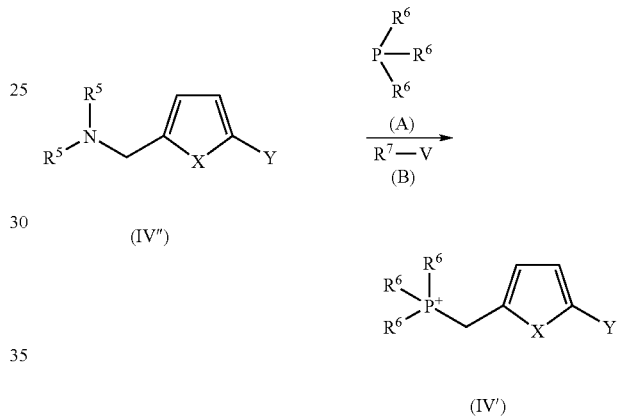

In the above reaction scheme, $R^5$, $R^6$, $R^7$, V, X and Y have the same meanings as those indicated hereinbefore.

The amount of the compound having the general formula (A) used is generally from 0.5 to 40.0 molar equivalents of the amount of the compound having the general formula (IV'') or salt thereof used, and preferably from 1.0 to 10.0 molar equivalents.

The amount of the compound having the general formula (B) used is generally from 0.5 to 40.0 molar equivalents of the amount of the compound having the general formula (IV'') or salt thereof used, and preferably from 1.0 to 10.0 molar equivalents.

The reaction of this Step is generally carried out in a solvent. The solvent employed in the above reaction can be, for example, an amide such as N,N-dimethylformamide, N,N-dimethylacetamide or N-methylpyrrolidone; a sulfoxide such as dimethyl sulfoxide; a halogenated hydrocarbon such as chloroform or dichloromethane; an aromatic hydrocarbon such as benzene or toluene; an aliphatic hydrocarbon such as hexane or cyclohexane; an ether such as tetrahydrofuran, dioxane, diethyl ether or dimethoxyethane; an ester such as methyl acetate or ethyl acetate; or a nitrile such as acetonitrile or propionitrile. These solvents may be used in the above reaction as mixtures containing at least two of them in any ratio.

The solvent employed in the above reaction is preferably a mixed solvent of an aromatic hydrocarbon and a nitrile and more preferably a mixed solvent of toluene and acetonitrile.

The reaction temperature employed in the above reaction is generally between −80° C. and 150° C., and preferably between −20° C. and 50° C.

The reaction time employed in the above reaction is generally from 1 minute to 240 hours, and preferably from 10 minutes to 120 hours.

The compound having the general formula (IV') or salt thereof thus obtained can be isolated and purified by any known procedures for isolation and purification, for example, through evaporation, concentration under reduced pressure, extraction with solvent, crystallization, recrystallization, partitioning between solvent systems, chromatography and the like.

EXAMPLES

The present invention is described in more detail hereinafter by way of the Examples and the Test examples, but the scope of the present invention should not be limited to these examples.

Example 1

(2R,4S)-2-t-Butyl-4-methyl-1,3-oxazolidine-3,4-dicarboxylic acid dimethyl ester (Compound Shown as Ia in Table 1: Exemplification Compound Number 55)

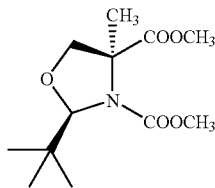

To a solution of (2R,4S)-2-t-butyl-1,3-oxazolidine-3,4-dicarboxylic acid dimethyl ester (384 g, 1.57 mol) prepared according to the procedure described in the literature (CHIMICA, 42, 176 (1988)) in tetrahydrofuran (2300 mL) were added successively tetraethylene glycol dimethyl ether (380 mL) and methyl iodide (290 mL, 4.70 mol) under a nitrogen atmosphere with stirring, and the resulting mixture was cooled to about −20° C. Subsequently, to the resulting mixture was added dropwise slowly a solution of potassium t-butoxide (263 g, 2.35 mol) in tetrahydrofuran (1900 mL) below −5° C. under a nitrogen atmosphere with stirring, and the resulting mixture was stirred at about −10° C. for 1 hour. After stirring, a 10% aqueous ammonium chloride solution was added to the reaction mixture with stirring to quench the reaction, and the resulting mixture was extracted with toluene. The extract separated was washed twice with a 5% aqueous sodium chloride solution and evaporated in vacuo to afford the crude product of the title compound (373 g (determined by HPLC), yield: 92%). The crude product thus obtained was used for the following reaction step without further purification. Additionally, it could be possible to obtain the pure title compound by purifying the crude product by chromatography on a silica gel column (eluent: a mixed solvent of ethyl acetate and hexane).

$[\alpha]_D^{27}$ −9.74 (c 1.001, MeOH). $^1$H NMR (CDCL$_3$, 400 MHz): δ 0.97 (s, 9H), 1.62 (s, 3H), 3.69 (s, 3H), 3.77 (s, 3H), 3.82 (d, 1H, J=8.3 Hz), 4.28 (d, 1H, J=8.3 Hz), 5.15 (s, 1H). $^{13}$C NMR (CDCL$_3$, 100 MHz): δ 21.2, 26.3, 39.0, 52.4, 52.6, 66.5, 76.9, 97.6, 155.1, 172.2. IR vmax (Liquid Film): 2958, 2909, 1737, 1719, 1478, 1443, 1345, 1313, 1282, 1249, 1218, 1195, 1141, 1115, 1059, 1034 cm$^{-1}$.

Example 2

(2R,4R)-2-t-Butyl-4-hydroxymethyl-4-methyl-1,3-oxazolidine-3-carboxylic acid methyl ester (Compound Shown as Ib in Table 2: Exemplification Compound Number 28)

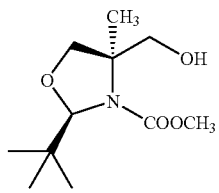

A mixture of lithium chloride (132 g, 3.13 mol), potassium borohydride (168 g, 3.13 mol) and tetrahydrofuran (3800 mL) was stirred at room temperature under a nitrogen atmosphere for 1 hour. Subsequently, to the mixture was added a solution of (2R,4S)-2-t-butyl-4-methyl-1,3-oxazolidine-3,4-dicarboxylic acid dimethyl ester (373 g, 1.44 mol) prepared according to the procedure described in Example 1 in toluene (1150 mL) under a nitrogen atmosphere with stirring, and the resulting mixture was warmed to about 45° C. and furthermore stirred at the same temperature for 3 hours. After stirring, the reaction mixture was cooled in an ice-bath, and to the reaction mixture was added slowly a 10% aqueous ammonium chloride solution with stirring to quench the reaction. The reaction mixture was extracted with toluene, and the extract was washed with water and evaporated in vacuo to afford the crude product of the title compound (327 g (determined by HPLC), yield: 98%,). The crude product thus obtained was used for the following reaction step without further purification. Additionally, it could be possible to obtain the pure title compound by purifying the crude product by chromatography on a silica gel column (eluent: a mixed solvent of ethyl acetate and hexane).

$[\alpha]_D^{27}$ +12.7 (c 1.009, MeOH). $^1$H NMR (CDCL$_3$, 400 MHz): δ 0.93 (s, 9H), 1.43 (s, 3H), 3.55 (brd, 1H, J=11.3 Hz), 3.71 (s, 3H), 3.74 (d, 1H, J=8.6 Hz), 3.83 (d, 1H, J=11.3 Hz), 3.87 (brd, 1H, J=8.6 Hz), 5.13 (s, 1H). $^{13}$C NMR (CDCL$_3$, 100 MHz): δ 19.5, 26.4, 38.6, 52.5, 65.2, 67.1, 75.8, 97.3, 156.8. IR vmax (Liquid Film): 3440, 2959, 2909, 2875, 1709, 1686, 1479, 1447, 1399, 1358, 1317, 1281, 1196, 1172, 1134, 1112, 1069, 1047, 960, 805, 759 cm$^{-1}$.

Example 3

(2R,4S)-2-t-Butyl-4-formyl-4-methyl-1,3-oxazolidine-3-carboxylic acid methyl ester (Compound Shown as Ic in Table 2: Exemplification Compound Number 28)

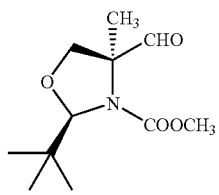

To a solution of (2R,4S)-2-t-butyl-4-hydroxymethyl-4-methyl-1,3-oxazolidine-3-carboxylic acid methyl ester (260 g, 1.12 mol) prepared according to the procedure described in Example 2 in toluene (6000 mL) were added successively water (3000 mL), sodium bromide (128 g) and sodium hydrogencarbonate (260 g) with stirring, and the resulting mixture was cooled to about 0° C. Subsequently, to the resulting mixture was added 2,2,6,6-tetramethylpiperidinooxy, free radical (1.94 g, 0.0125 mol) with stirring, and furthermore, to the resulting mixture was added dropwise slowly a 12.7% aqueous sodium hypochlorite solution (748 mL, 1.34 mol) below 5° C. with stirring, and the resulting mixture was furthermore stirred at about 0° C. for 30 minutes. After stirring, ethanol was added to the reaction mixture with stirring, and the resulting mixture was stirred for about 1 hour, and then the reaction was quenched. After partitioning the reaction mixture, the organic layer separated was washed successively with an aqueous sodium thiosulfate solution and water, and evaporated in vacuo to afford the crude product of the title compound (225 g, yield: 87%). The crude product thus obtained was used for the following reaction step without further purification. Additionally, it could be possible to obtain the pure title compound by recrystallization of the crude product from hexane.

$[\alpha]_D^{27}$ –7.09 (c 1.002, acetonitrile). $^1$H NMR (CDCL$_3$, 400 MHz): δ 0.98 (s, 9H), 1.48 (s, 3H), 3.67 (d, 1H, J=8.8 Hz), 3.70 (s, 3H), 4.17 (d, 1H, J=8.8 Hz), 5.20 (s, 1H), 9.72 (s, 1H). $^{13}$C NMR (CDCL$_3$, 100 MHz): δ 18.1, 26.3, 38.9, 52.7, 70.0, 73.1, 97.3, 155.6, 199.2. IR νmax (KBr): 2982, 2967, 2958, 2938, 2897, 2887, 1737, 1711, 1476, 1443, 1357, 1340, 1307, 1216, 1198, 1181, 1115, 1051, 995, 950, 937 cm$^{-1}$.

Example 4

(2R,4R)-2-t-Butyl-4-methyl-4-[2-(1-methyl-1H-pyrrol-2-yl)ethyl]-1,3-oxazolidine-3-carboxylic acid methyl ester (Compound Shown as Id in Table 3: Exemplification Compound Number 121)

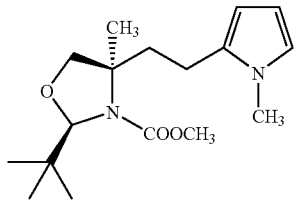

To a solution of (2R,4S)-2-t-butyl-4-formyl-4-methyl-1,3-oxazolidine-3-carboxylic acid methyl ester (225 g, 0.981 mol) prepared according to the procedure described in Example 3 in N,N-dimethylformamide (1125 mL) was added [(1-methyl-1H-pyrrol-2-yl)methyl]triphenylphosphonium iodide (522 g, 1.08 mol) prepared according the procedure described in the literature (J. Org. Chem., 52, 19 (1987) with stirring, and the resulting mixture was cooled to about –10° C. Subsequently, to the reaction mixture was added dropwise a solution of potassium t-butoxide (132 g, 1.18 mol) in dimethylformamide (125 mL) below 5° C. with stirring, and the resulting mixture was stirred at about 0° C. for about 1 hour. After stirring, water was added to the reaction mixture to quench the reaction, and the reaction mixture was extracted with heptane. The extract was evaporated in vacuo to afford the Wittig reaction product.

Subsequently, to a solution of the Wittig reaction product obtained above in methanol (2250 mL) was added 5% palladium-charcoal (45 g) with shaking, and the resulting mixture was shaken at room temperature under a hydrogen atmosphere for about 1.5 hours. After shaking, the reaction mixture was filtered through a membrane filter (pore diameter: 0.2 μm), and the filtrate was evaporated in vacuo. The residue obtained was recrystallized from a mixed solvent of methanol and water (1:1, v/v) to afford the almost pure title compound (278 g, yield: 92%).

$[\alpha]_D^{27}$ –12.6 (c 1.001, MeOH). $^1$H NMR (CDCL$_3$, 400 MHz): δ 0.97 (s, 9H), 1.43 (s, 3H), 2.05 (apparent dt, 1H, J=4.3, 12.8 Hz), 2.39 (apparent dt, 1H, J=4.1, 12.7 Hz), 2.51 (ddd, 1H, J=4.4, 12.4, 14.6 Hz), 2.61 (ddd, 1H, J=4.6, 12.6, 14.5 Hz), 3.55 (s, 3H), 3.69 (s, 1H), 3.70 (d, 3H, J=8.3 Hz), 4.00 (d, 1H, J=8.3 Hz), 5.15 (s, 1H), 5.90 (brs, 1H), 6.05 (s, 1H), 6.53 (brs, 1H). $^{13}$C NMR (DMSO-d$_6$, 100 MHz): δ 21.6, 22.1, 26.6, 33.2, 37.2, 38.3, 52.1, 63.7, 77.1, 96.5, 105.1, 106.3, 121.4, 132.3, 156.2. IR νmax (KBr): 2979, 2954, 2921, 2891, 1698, 1493, 1466, 1447, 1351, 1318, 1304, 1168, 1098, 1063, 958, 725 cm$^{-1}$.

Example 5

(2R,4S)-2-Isopropyl-4-methyl-1,3-oxazolidine-3,4-dicarboxylic acid dimethyl ester (Compound Shown as Ia in Table 1: Exemplification Compound Number 13)

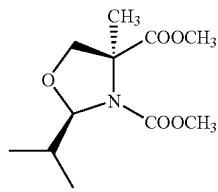

(i) (4S)-2-Isopropyl-1,3-oxazolidine-4-carboxylic acid methyl ester

To a suspension of L-serine methyl ester hydrochloride (50.00 g, 321 mmol) in toluene (500 mL) were added successively 2-methylpropanal (35.2 mL, 385 mmol), triethylamine (49.3 mL, 354 mmol) and water-absorbing polymer (2.50 g) under a nitrogen atmosphere with stirring, and the resulting mixture was stirred at 45° C. for 2 hours under the nitrogen atmosphere. After cooling the reaction mixture to 25° C., the insoluble materials were filtered off, and the insoluble materials separated were washed with toluene (250 mL). The filtrate and the washings were combined and evaporated in vacuo to remove toluene, and the residue obtained was purified by distillation under reduced pressure to afford the title compound (97-98° C./10 mm Hg, 44.66 g, yield: 80%).

$^1$H NMR (CDCl$_3$, 400 MHz): δ 0.94 (d, J=6.8 Hz, 3H), 1.01 (d, J=6.8 Hz, 3H), 1.60-1.92 (m, 1H), 2.00-2.45 (m, 1H), 3.72-3.80 (m, 4H), 3.85-4.20 (m, 3H). MS (FAB): m/z 174 (M+H$^+$). HRMS (FAB): calcd for C$_8$H$_{16}$NO$_3$ (M+H$^+$): 174.1130. found: 174.1127.

(ii) (2R,4S)-2-Isopropyl-1,3-oxazolidine-3,4-dicarboxylic acid dimethyl ester

A mixture of (4S)-2-isopropyl-1,3-oxazolidine-4-carboxylic acid methyl ester (28.22 g, 163 mmol) synthesized according to the procedure described in Step (i) and toluene (250 mL) was cooled to about 0° C. under a nitrogen atmosphere with stirring. Subsequently, to the mixture was added dropwise methyl chloroformate (21.4 mL, 277 mmol) below 5° C. with stirring under a nitrogen atmosphere, and the resulting mixture was stirred at about 0° C. for 1 hour. After stirring, triethylamine (22.7 mL, 163 mmol) was added dropwise to the reaction mixture, and the resulting mixture was stirred at about 25° C. for 1 hour. After stirring, water (100 mL) was added to the reaction mixture to quench the reaction, and the resulting mixture was partitioned. The organic layer separated was washed with water and evaporated in vacuo to afford the crude product of the title compound (47.25 g, yield: 125%). Additionally, it could be possible to obtain the pure title compound by purifying the crude product by chromatography on a silica gel column (eluent: a mixed solvent of ethyl acetate and hexane).

$^1$H NMR (CDCl$_3$, 400 MHz): δ 0.72 (d, J=6.8 Hz, 3H), 0.97 (d, J=6.8 Hz, 3H), 1.95-2.30 (m, 1H), 3.71 (s, 6H), 4.05-4.18 (m, 2H), 4.38-4.62 (m, 1H), 4.85-5.07 (m, 1H). MS (FAB): m/z 232 (M+H$^+$), 188, 160. HRMS (ESI): calcd for C$_{10}$H$_{17}$NNaO$_5$ (M+Na$^+$): 254.1004. found: 254.1016.

(iii) (2R,4S)-2-Isopropyl-4-methyl-1,3-oxazolidine-3,4-dicarboxylic acid dimethyl ester Following the procedure mentioned in Example 1, a similar reaction was carried out using (2R,4S)-2-isopropyl-1,3-oxazolidine-3,4-dicarboxylic acid dimethyl ester (36.31 g, 157 mmol) synthesized according to the procedure described in Step (ii) to afford the crude product of the title compound (38.22 g (determined by HPLC), yield: 99%). Additionally, it could be possible to obtain the pure title compound in crystalline form (28.28 g, yield: 73%) by replacing the solvent containing the crude title compound by IsoparE and adjusting the solvent volume to 135 mL, followed by cooling the solution containing the title compound to 0° C.

$^1$H NMR: (CDCl$_3$, 400 MHz) δ 0.92 (d, J=6.8 Hz, 3H), 0.99 (d, J=6.8 Hz, 3H), 1.59 (s, 3H), 2.10-2.58 (m, 1H), 3.37 (s, 3H), 3.55 (s, 3H), 3.78 (d, J=8.2 Hz, 1H), 4.19 (d, J=8.2 Hz, 1H), 4.90-5.12 (m, 1H). MS (FAB): m/z 246 (M+H$^+$), 202, 174. HRMS (EST): calcd for C$_{11}$H$_{19}$NNaO$_5$ (M+Na$^+$): 268.1161. found: 268.1181.

Example 6

(2R,4S)-2-Isopropyl-4-hydroxymethyl-4-methyl-1,3-oxazolidine-3-carboxylic acid methyl ester (Compound Shown as Ib in Table 2: Exemplification Compound Number 7)

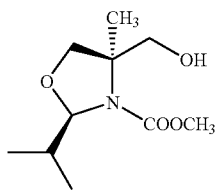

Following the procedure mentioned in Example 2, a similar reaction was carried out using (2R,4S)-2-isopropyl-4-methyl-1,3-oxazolidine-3,4-dicarboxylic acid dimethyl ester (10.00 g, 40.8 mmol) synthesized according to the procedure described in Example 5 to afford the crude product of the title compound (7.62 g (determined by HPLC), yield: 86%). Additionally, it could be possible to obtain the pure title compound by purifying the crude product by chromatography on a silica gel column (eluent: a mixed solvent of ethyl acetate and hexane).

$^1$H NMR (CDCl$_3$, 400 MHz): δ 0.90 (d, J=6.8 Hz, 3H), 0.99 (d, J=6.8 Hz, 3H), 1.41 (s, 3H), 2.05-2.26 (m, 1H), 3.45-3.92 (m, 7H), 5.00 (d, J=4.4 Hz, 1H). MS (FAB): m/z 218 (M+H$^+$), 186. HRMS (ESI): calcd for C$_{10}$H$_9$NNaO$_4$(M+Na$^+$): 240.1212. found: 240.1183.

Example 7

(2R,4S)-2-Isopropyl-4-formyl-4-methyl-1,3-oxazolidine-3-carboxylic acid methyl ester (Compound Shown as Ic in Table 2: Exemplification Compound Number 7)

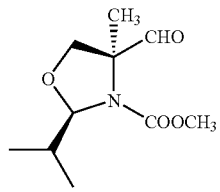

Following the procedure mentioned in Example 3, a similar reaction was carried out using (2R,4S)-2-isopropyl-4-hydroxymethyl-4-methyl-1,3-oxazolidine-3-carboxylic acid methyl ester (8.00 g, 36.8 mmol) synthesized according to the procedure described in Example 6 to afford the crude product of the title compound (7.13 g (determined by HPLC), yield: 90%). Additionally, it could be possible to obtain the pure title compound by purifying the crude product by chromatography on a silica gel column (eluent: a mixed solvent of ethyl acetate and hexane).

$^1$H NMR (CDCl$_3$, 400 MHz): δ 0.85 (d, J=6.8 Hz, 3H), 0.93 (d, J=6.8 Hz, 3H), 1.46 (s, 3H), 2.20-2.54 (m, 1H), 3.63 (d, J=7.2 Hz, 1H), 3.72 (s, 3H), 4.07 (d, J=7.2 Hz, 1H), 4.98-5.25 (m, 1H), 9.60 (s, 1H). MS (FAB): m/z 216 (M+H$^+$), 186. HRMS (ESI): calcd for C$_{10}$H$_{17}$NNaO$_4$ (M+Na$^+$): 238.1055. found: 238.1032.

Example 8

(2R,4R)-2-Isopropyl-4-methyl-[2-(1-methyl-1H-pyrrol-2-yl)ethyl]-1,3-oxazolidine-3-carboxylic acid methyl ester (Compound Shown as Id in Table 3: Exemplification Compound Number 25)

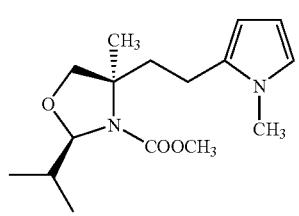

Following the procedure mentioned in Example 4, a similar reaction was carried out using (2R,4S)-2-isopropyl-4-formyl-4-methyl-1,3-oxazolidine-3-carboxylic acid methyl ester (20.80 g, 96.6 mmol) synthesized according to the procedure described in Example 7 to afford the crude product of the title compound (25.33 g (determined by HPLC), yield: 89%). Additionally, it could be possible to obtain the pure title compound by purifying the crude product by chromatography on a silica gel column (eluent: a mixed solvent of ethyl acetate and hexane).

¹H NMR (DMSO-d₆, 400 MHz): δ 0.83 (d, J=6.8 Hz, 3H), 0.91 (d, J=6.8 Hz, 3H), 1.35 (s, 3H), 1.80-2.15 (m, 3H), 2.44-2.52 (m, 2H), 3.47 (s, 3H), 3.53-3.72 (m, 4H), 3.95 (d, J=8.4 Hz, 1H), 4.90 (d, J=4.4 Hz, 1H), 5.70-5.73 (m, 1H), 5.83-5.85 (m, 1H), 6.57-6.60 (m, 1H). MS (FAB): m/z 295 (M+H⁺), 148, 94. HRMS (FAB): calcd for $C_{16}H_{26}N_2O_3$: 294.1943. found: 294.1936.

Example 9

(2R,4S)-2-Isopropyl-4-methyl-1,3-oxazolidine-3,4-dicarboxylic acid 3-t-butyl ester 4-methyl ester (Compound Shown as Ia in Table 1: Exemplification Compound Number 1)

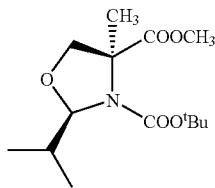

(i) (2R,4S)-2-Isopropyl-1,3-oxazolidine-3,4-dicarboxylic acid 3-t-butyl ester 4-methyl ester A mixture of (4S)-2-isopropyl-1,3-oxazolidine-4-carboxylic acid methyl ester (30.00 g, 173 mmol) synthesized according to the procedure described in Example 5 (i), Boc₂O (39.8 mL, 173 mL) and tetrahydrofuran (300 mL) was stirred at about 45° C. for 4 hours. After stirring, the reaction mixture was cooled to about 25° C. and evaporated in vacuo to afford the crude product of the title compound (45.93 g (determined by HPLC), yield: 97%). Additionally, it could be possible to obtain the pure title compound by purifying the crude product by chromatography on a silica gel column (eluent: a mixed solvent of ethyl acetate and hexane).

¹H NMR (CDCl₃, 400 MHz): δ 0.72 (d, J=6.8 Hz, 3H), 0.97 (d, J=6.8 Hz, 3H), 1.44 (s, 9H), 1.84-2.15 (m, 1H), 3.73 (s, 3H), 4.05-4.15 (m, 2H), 4.20-4.34 (m, 1H), 4.85-5.02 (m, 1H). MS (FAB): m/z 274 (M+H⁺), 218, 174, 146, 130. HRMS (ESI): calcd for $C_{13}H_{23}NNaO_5$ (M+Na⁺): 296.1474. found: 296.1492.

(ii) (2R,4S)-2-Isopropyl-4-methyl-1,3-oxazolidine-3,4-dicarboxylic acid 3-t-butyl ester 4-methyl ester Following the procedure mentioned in Example 1, a similar reaction was carried out using (2R,4S)-2-isopropyl-1,3-oxazolidine-3,4-dicarboxylic acid 3-t-butyl ester 4-methyl ester (45.93 g, 168 mmol) synthesized according to the procedure described in Step (i) to afford the crude product of the title compound (41.27 g (determined by HPLC), yield: 86%). Additionally, it could be possible to obtain the pure title compound by purifying the crude product by chromatography on a silica gel column (eluent: a mixed solvent of ethyl acetate and hexane).

¹H NMR (CDCl₃, 400 MHz): δ 0.85 (d, J=6.8 Hz, 3H), 0.95 (d, J=6.8 Hz, 3H), 1.41 (s, 9H), 1.57 (s, 3H), 2.20-2.53 (m, 1H), 3.73 (s, 3H), 3.75 (d, J=8.3 Hz, 1H), 4.14 (d, J=8.3 Hz, 1H), 4.85-5.16 (m, 1H). MS (FAB): m/z 288 (M+H⁺), 232, 188, 144. HRMS (ESI): calcd for $C_{14}H_{25}NNaO_5$ (M+Na⁺): 310.1630. found: 310.1604.

Example 10

(2R,4S)-2-Isopropyl-4-hydroxymethyl-4-methyl-1,3-oxazolidine-3-carboxylic acid t-butyl ester (Compound Shown as Ib in Table 2: Exemplification Compound Number 1)

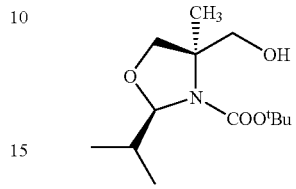

Following the procedure mentioned in Example 2, a similar reaction was carried out using (2R,4S)-2-isopropyl-4-methyl-1,3-oxazolidine-3,4-dicarboxylic acid 3-t-butyl ester 4-methyl ester (41.27 g, 144 mmol) synthesized according to the procedure described in Example 9 to afford the crude product of the title compound (35.23 g (determined by HPLC), yield: 95%). Additionally, it could be possible to obtain the pure title compound by purifying the crude product by chromatography on a silica gel column (eluent: a mixed solvent of ethyl acetate and hexane).

¹H NMR (CDCl₃, 400 MHz): δ 0.84 (d, J=6.8 Hz, 3H), 0.93 (d, J=6.8 Hz, 3H), 1.40 (s, 3H), 1.44 (s, 9H), 2.00-2.15 (m, 1H), 3.38-3.82 (m, 4H), 4.90-4.98 (m, 1H). MS (FAB): m/z 260 (M+H⁺), 204, 132. HRMS (ESI): calcd for $C_{13}H_{25}NNaO_4$ (M+Na⁺): 282.1681. found: 282.1682.

Example 11

(2R,4S)-2-Isopropyl-4-formyl-4-methyl-1,3-oxazolidine-3-carboxylic acid t-butyl ester (Compound Shown as Ic in Table 2: Exemplification Compound Number 1)

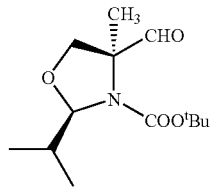

Following the procedure mentioned in Example 3, a similar reaction was carried out using (2R,4S)-2-isopropyl-4-hydroxymethyl-4-methyl-1,3-oxazolidine-3-carboxylic acid t-butyl ester (35.23 g, 136 mmol) synthesized according to the procedure described in Example 10 to afford the crude product of the title compound (24.80 g (determined by HPLC), yield: 71%). Additionally, it could be possible to obtain the pure title compound by purifying the crude product by chromatography on a silica gel column (eluent: a mixed solvent of ethyl acetate and hexane).

¹H NMR (CDCl₃, 400 MHz): δ 0.89 (d, J=6.8 Hz, 3H), 0.98 (d, J=6.8 Hz, 3H), 1.42 (s, 9H), 1.45 (s, 3H), 2.10-2.55 (m, 1H), 3.61 (d, J=8.2 Hz, 1H), 4.04 (d, J=8.2 Hz, 1H), 4.85-5.18 (m, 1H), 9.55 (s, 1H). MS (FAB): m/z 258 (M+H⁺), 202, 130. HRMS (FAB): calcd for $C_{13}H_{24}NO_4$ (M+H⁺): 258.1705. found: 258.1709.

Example 12

(2R,4R)-2-Isopropyl-4-methyl-4-[2-(1-methyl-1H-pyrrol-2-yl)ethyl]-1,3-oxazolidine-3-carboxylic acid t-butyl ester (Compound Shown as Id in Table 3: Exemplification Compound Number 1)

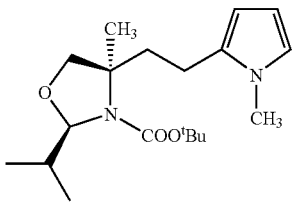

Following the procedure mentioned in Example 4, a similar reaction was carried out using (2R,4S)-2-isopropyl-4-formyl-4-methyl-1,3-oxazolidine-3-carboxylic acid t-butyl ester (8.00 g, 31.1 mmol) synthesized according to the procedure described in Example 11 to afford the crude product of the title compound (10.17 g (determined by HPLC), yield: 97%). Additionally, it could be possible to obtain the pure title compound by purifying the crude product by chromatography on a silica gel column (eluent: a mixed solvent of ethyl acetate and hexane).

$^1$H NMR: (DMSO-$d_6$, 400 MHz): δ 0.83 (d, J=6.8 Hz, 3H), 0.93 (d, J=6.8 Hz, 3H), 1.35 (s, 3H), 1.41 (s, 9H), 1.80-2.15 (m, 3H), 2.43-2.53 (m, 2H), 3.37 (s, 3H), 3.58 (d, J=7.6 Hz, 1H), 3.94 (d, J=7.6 Hz, 1H), 4.85 (d, J=4.4 Hz, 1H), 5.71-5.74 (m, 1H), 5.82-5.86 (m, 1H), 6.57-6.60 (m, 1H). MS (FAB): m/z 336 (M$^+$), 281, 148, 94. HRMS (ESI): calcd for $C_{19}H_{32}N_2NaO_3$ (M+Na$^+$): 359.2311. found: 359.2292.

Example 13

(2R,4S)-2-(2-Ethylpropyl)-4-methyl-1,3-oxazolidine-3,4-dicarboxylic acid dimethyl ester (Compound Shown as Ia in Table 1: Exemplification Compound Number 97)

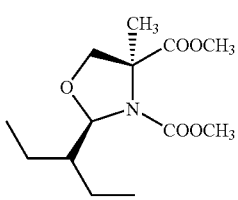

(i)  (4S)-2-(2-Ethylpropyl)-1,3-oxazolidine-4-carboxylic acid methyl ester

To a suspension of L-serine methyl ester hydrochloride (50.00 g, 321 mmol) in toluene (500 mL) were added successively 2-methylpropanal (47.5 mL, 386 mmol), triethylamine (49.3 mL, 354 mmol) and water-absorbing polymer (2.50 g) under a nitrogen atmosphere with stirring, and the resulting mixture was stirred at 45° C. for 2 hours under the nitrogen atmosphere. After cooling the reaction mixture to 25° C., the insoluble materials were filtered off, and the insoluble materials were washed with toluene (250 mL). The filtrate and the washings were combined and evaporated in vacuo to afford the crude product of the title compound (55.83 g, yield: 86%).

$^1$H NMR (CDCl$_3$, 400 MHz): δ 0.83-0.93 (m, 9H), 1.28-1.59 (m, 4H), 2.45-2.55 (m, 1H), 3.66-3.98 (m, 3H), 4.02-4.46 (m, 2H). MS (FAB): m/z 202 (M+H$^+$), 200, 130. HRMS (ESI): calcd for $C_{10}H_{19}NNaO_3$ (M+Na$^+$): 224.1263. found: 224.1262.

(ii)  (2R,4S)-2-(2-Ethylpropyl)-1,3-oxazolidine-3,4-dicarboxylic acid dimethyl ester Following the procedure mentioned in Example 5 (ii), a similar reaction was carried out using (4S)-2-(2-ethylpropyl)-1,3-oxazolidine-4-carboxylic acid methyl ester (5.00 g, 24.8 mmol) synthesized according to the procedure described in Step (i) to afford the crude product of the title compound. The crude product thus obtained was purified by chromatography on a silica gel column (eluent: a mixed solvent of ethyl acetate and hexane) to afford the pure title compound (5.21 g, yield: 81%).

$^1$H NMR (CDCl$_3$, 400 MHz): δ 0.70 (t, J=7.6 Hz, 3H), 0.86 (t, J=7.6 Hz, 3H), 1.15-1.95 (m, 5H), 3.71 (s, 3H), 3.74 (s, 3H), 4.04-4.19 (m, 2H), 4.40-4.64 (m, 1H), 5.05-5.18 (m, 1H). MS (FAB): m/z 260 (M+H$^+$), 188, 160. HRMS (ESI): calcd for $C_{12}H_{21}NNaO_5$ (M+Na$^+$): 282.1317. found: 282.1327.

(iii) (2R,4S)-2-(2-Ethylpropyl)-4-methyl-1,3-oxazolidine-3,4-dicarboxylic acid dimethyl ester Following the procedure mentioned in Example 1, a similar reaction was carried out using (2R,4S)-2-(2-ethylpropyl)-1,3-oxazolidine-3,4-dicarboxylic acid dimethyl ester (5.21 g, 20.1 mmol) synthesized according to the procedure described in Step (ii) to afford the crude product of the title compound. The crude product thus obtained was purified by the reverse phase chromatography (eluent: a mixed solvent of acetonitrile and water) to afford the pure title compound (5.09 g, yield: 93%).

$^1$H NMR (CDCl$_3$, 400 MHz): δ 0.89 (t, J=7.6 Hz, 3H), 0.95 (t, J=7.6 Hz, 3H), 1.15-1.70 (m, 7H), 1.78-2.13 (m, 1H), 3.69 (s, 3H), 3.73-3.78 (m, 4H), 4.20 (d, J=8.5 Hz, 1H), 5.18-5.29 (m, 1H). MS (FAB): m/z 274 (M+H$^+$), 202, 174. HRMS (ESI): calcd for $C_{13}H_{23}NNaO_5$ (M+Na$^+$): 296.1474. found: 296.1489.

Example 14

(2R,4S)-2-(2-Ethylpropyl)-4-hydroxymethyl-4-methyl-1,3-oxazolidine-3-carboxylic acid methyl ester (Compound Shown as Ib in Table 2: Exemplification Compound Number 49)

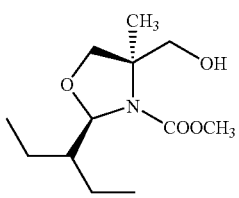

Following the procedure mentioned in Example 2, a similar reaction was carried out using (2R,4S)-2-(2-ethylpropyl)-4-methyl-1,3-oxazolidine-3,4-dicarboxylic acid dimethyl ester (5.09 g, 18.6 mmol) synthesized according to the procedure described in Example 13 to afford the crude product of the title compound. The crude product thus obtained was purified by the reverse phase chromatography (eluent: a mixed solvent of acetonitrile and water) to afford the pure title compound (3.35 g, yield: 73%).

$^1$H NMR (CDCl$_3$, 400 MHz): δ 0.70 (t, J=7.6 Hz, 3H), 0.84 (t, J=7.6 Hz, 3H), 1.12-1.70 (m, 7H), 1.90-2.25 (m, 1H), 3.40-3.82 (m, 7H), 5.20 (d, J=4.0 Hz, 1H). MS (FAB): m/z 246 (M+H$^+$), 174, 146. HRMS (ESI): calcd for C$_{12}$H$_{23}$NNaO$_4$(M+Na$^+$): 268.1525. found: 268.1539.

Example 15

(2R,4S)-2-(2-Ethylpropyl)-4-formyl-4-methyl-1,3-oxazolidine-3-carboxylic acid methyl ester (Compound Shown as Ic in Table 2: Exemplification Compound Number 49)

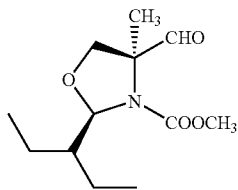

Following the procedure mentioned in Example 3, a similar reaction was carried out using (2R,4S)-2-(2-ethylpropyl)-4-hydroxymethyl-4-methyl-1,3-oxazolidine-3-carboxylic acid methyl ester (3.00 g, 12.2 mmol) synthesized according to the procedure described in Example 14 to afford the crude product of the title compound. The crude product thus obtained Was purified by chromatography on a silica gel column (eluent: a mixed solvent of ethyl acetate and hexane) to afford the pure title compound (2.55 g, yield: 86%).

$^1$H NMR (CDCl$_3$, 400 MHz): δ 0.73 (t, J=7.6 Hz, 3H), 0.80 (t, J=7.6 Hz, 3H), 1.12-1.56 (m, 7H), 1.85-2.12 (m, 1H), 3.62 (d, J=8.8 Hz, 1H), 3.71 (s, 3H), 4.10 (d, J=8.8 Hz, 1H), 5.15-5.34 (m, 1H), 9.63 (s, 1H). MS (FAB): m/z 244 (M+H$^+$), 144. HRMS (ESI): calcd for C$_{12}$H$_{23}$NNaO$_4$(M+Na$^+$): 266.1368. found: 266.1378.

Example 16

(2R,4R)-2-(2-Ethylpropyl)-4-methyl-4-[2-(1-methyl-1H-pyrrol-2-yl)ethyl]-1,3-oxazolidine-3-carboxylic acid methyl ester (Compound Shown as Id in Table 3: Exemplification Compound Number 265)

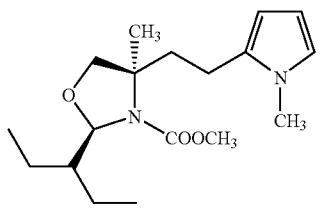

Following the procedure mentioned in Example 4, a similar reaction was carried out using (2R,4S)-2-(2-ethylpropyl)-4-formyl-4-methyl-1,3-oxazolidine-3-carboxylic acid methyl ester (2.00 g, 8.2 mmol) synthesized according to the procedure described in Example 15 to afford the crude product of the title compound. The crude product thus obtained was purified by reverse phase chromatography (eluent: a mixed solvent of acetonitrile and water) to afford the pure title compound (2.04 g, yield: 77%).

$^1$H NMR (DMSO-d$_6$, 400 MHz): δ 0.85 (d, J=7.6 Hz, 3H), 0.91 (d, J=7.6 Hz, 3H), 1.15-1.50 (m, 7H), 1.85-2.14 (m, 3H), 2.44-2.54 (m, 2H), 3.48 (s, 3H), 3.56-3.61 (m, 4H), 3.94 (d, J=8.8 Hz, 1H), 5.09 (d, J=4.4 Hz, 1H), 5.69-5.73 (m, 1H), 5.83-5.86 (m, 1H), 6.56-6.60 (m, 1H). MS (FAB): m/z 323 (M+H$^+$), 148. HRMS (ESI): calcd for C$_{18}$H$_{31}$N$_2$O$_3$ (M+H$^+$): 323.2335. found: 323.2349.

Example 17

(2R,4S)-2-(2-Ethylpropyl)-4-hydroxymethyl-4-methyl-1,3-oxazolidine-3-carboxylic acid t-butyl ester (Compound Shown as Ia in Table 1: Exemplification Compound Number 85)

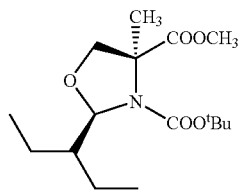

(i) (2R,4S)-2-(2-Ethylpropyl)-1,3-oxazolidine-3,4-dicarboxylic acid 3-t-butyl ester 4-methyl ester Following the procedure mentioned in Example 9 (i), a similar reaction was carried out using (4S)-2-(2-ethylpropyl)-1,3-oxazolidine-4-carboxylic acid methyl ester (5.00 g, 24.8 mmol) synthesized according to the procedure described in Example 13(i) to afford the crude product of the title compound. The crude product thus obtained was purified by chromatography on a silica gel column (eluent: a mixed solvent of ethyl acetate and hexane) to afford the pure title compound (6.52 g, yield: 87%).

$^1$H NMR (CDCl$_3$, 400 MHz): δ 0.69 (t, J=7.6 Hz, 3H), 0.75 (t, J=7.6 Hz, 3H), 1.15-1.95 (m, 14H), 3.74 (s, 3H), 4.04-4.10 (m, 2H), 4.34-4.68 (m, 1H), 5.01-5.20 (m, 1H). MS (FAB): m/z 302 (M+H$^+$), 246, 146. HRMS (ESI): calcd for C$_{15}$H$_{27}$NNaO$_5$ (M+Na$^+$): 324.1787. found: 324.1801.

(ii) (2R,4S)-2-(2-Ethylpropyl)-4-methyl-1,3-oxazolidine-3,4-dicarboxylic acid 3-t-butyl ester 4-methyl ester Following the procedure mentioned in Example 1, a similar reaction was carried out using (2R,4S)-2-(2-ethylpropyl)-1,3-oxazolidine-3,4-dicarboxylic acid 3-t-butyl ester 4-methyl ester (4.00 g, 13.3 mmol) synthesized according to the procedure described in Step (i) to afford the crude product of the title compound. The crude product thus obtained was purified by chromatography on a silica gel column (eluent: a mixed solvent of ethyl acetate and hexane) to afford the pure title compound (3.35 g, yield: 80%).

$^1$H NMR (CDCl$_3$, 400 MHz): δ 0.75 (t, J=7.6 Hz, 3H), 0.86 (t, J=7.6 Hz, 3H), 1.02-2.02 (m, 17H), 3.59-3.63 (m, 4H), 4.14 (d, J=8.3 Hz, 1H), 5.13-5.27 (m, 1H). MS (FAB): m/z 316 (M+H$^+$), 216, 214. HRMS (ESI): calcd for C$_{16}$H$_{29}$NNaO$_5$ (M+Na$^+$): 338.1943. found: 338.1960.

Example 18

(2R,4S)-2-(2-Ethylpropyl)-4-hydroxymethyl-4-methyl-1,3-oxazolidine-3-carboxylic acid t-butyl ester (Compound Shown as Ib in Table 2: Exemplification Compound Number 43)

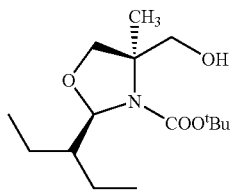

Following the procedure mentioned in Example 2, a similar reaction was carried out using (2R,4S)-2-(2-ethylpropyl)-4-methyl-1,3-oxazolidine-3,4-dicarboxylic acid 3-t-butyl ester 4-methyl ester (2.50 g, 8.0 mmol) synthesized according to the procedure described in Example 17 to afford the crude product of the title compound. The crude product thus obtained was purified by reverse phase chromatography (eluent: a mixed solvent of acetonitrile and water) to afford the pure title compound (2.17 g, yield: 95%

$^1$H NMR (CDCl$_3$, 400 MHz): δ 0.89 (t, J=7.6 Hz, 3H), 0.95 (t, J=7.6 Hz, 3H), 1.14-2.04 (m, 17H), 3.50-3.79 (m, 4H), 5.18 (d, J=3.3 Hz, 1H). MS (FAB): m/z 288 (M+H$^+$), 232, 132. HRMS (ESI): calcd for C$_{15}$H$_{29}$NNaO$_4$ (M+Na$^+$): 310.1994. found: 310.1992.

Example 19

(2R,4S)-2-(2-Ethylpropyl)-4-formyl-4-methyl-1,3-oxazolidine-3-carboxylic acid t-butyl ester (Compound Shown as Ic in Table 2: Exemplification Compound Number 43)

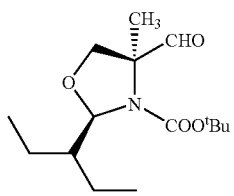

Following the procedure mentioned in Example 3, a similar reaction was carried out using (2R,4S)-2-(2-ethylpropyl)-4-hydroxymethyl-4-methyl-1,3-oxazolidine-3-carboxylic acid t-butyl ester (1.50 g, 5.2 mmol) synthesized according to the procedure described in Example 18 to afford the crude product of the title compound. The crude product thus obtained was purified by chromatography on a silica gel column (eluent: a mixed solvent of ethyl acetate and hexane) to afford the pure title compound (1.30 g, yield: 87%).

$^1$H NMR (CDCl$_3$, 400 MHz): δ 0.75 (t, J=7.6 Hz, 3H), 0.84 (t, J=7.6 Hz, 3H), 1.03-2.13 (m, 17H), 3.59 (d, J=9.0 Hz, 1H), 4.02 (d, J=9.0 Hz, 1H), 5.12-5.33 (m, 1H), 9.60 (s, 1H). MS (FAB): m/z 286 (M+H$^+$), 230, 130. HRMS (ESI): calcd for C$_{15}$H$_{27}$NNaO$_4$ (M+Na$^+$): 308.1838. found: 308.1853.

Example 20

(2R,4R)-2-(2-Ethylpropyl)-4-methyl-4-[2-(1-methyl-1H-pyrrol-2-yl)ethyl]-1,3-oxazolidine-3-carboxylic acid t-butyl ester (Compound Shown as Id in Table 3: Exemplification Compound Number 241)

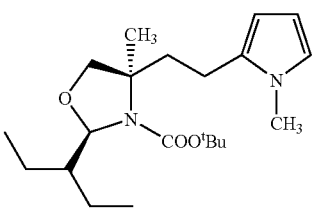

Following the procedure mentioned in Example 4, a similar reaction was carried out using (2R,4S)-2-(2-ethylpropyl)-4-formyl-4-methyl-1,3-oxazolidine-3-carboxylic acid t-butyl ester (1.00 g, 3.5 mmol) synthesized according to the procedure described in Example 19 to afford the crude product of the title compound. The crude product thus obtained was purified by reverse phase chromatography (eluent: a mixed solvent of acetonitrile and water) to afford the pure title compound (1.01 g, yield: 79%).

$^1$H NMR (DMSO-d$_6$, 400 MHz): δ 0.83 (d, J=7.6 Hz, 3H), 0.91 (d, J=7.6 Hz, 3H), 1.10-1.48 (m, 16H), 1.80-2.03 (m, 3H), 2.45-2.53 (m, 2H), 3.48 (s, 3H), 3.56 (d, J=8.6 Hz, 1H), 3.92 (d, J=8.6 Hz, 1H), 5.04 (d, J=4.0 Hz, 1H), 5.68-5.72 (m, 1H), 5.83-5.86 (m, 1H), 6.56-6.60 (m, 1H). MS (FAB): m/z 365 (M+H$^+$), 309, 148, 94. HRMS (ESI): calcd for C$_{21}$H$_{37}$N$_2$O$_3$ (M+H$^+$): 365.2804. found: 365.281.

Example 21

[(1-Methyl-1H-pyrrol-2-yl)methyl](triphenyl)phosphonium chloride

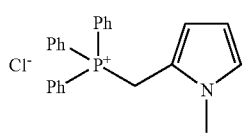

To a suspension of triphenylphosphine (3.83 g, 14.6 mmol) in acetonitrile (17 mL) was added acetyl chloride (1.04 mL, 14.6 mmol) under ice-cooling with stirring. Subsequently, to the resulting mixture was added dropwise slowly a solution of 1-methyl-2-(pyrrolidin-1-ylmethyl)-1H-pyrrole (2.00 g, 12.2 mmol) synthesized by the procedure described in the literature (J. Am. Chem. Soc. 73, 4921 (1951)) in toluene (17 mL) below 5° C. with stirring, and the resulting mixture was stirred under ice-cooling for 2 hours. After stirring, the precipitate formed was collected by filtration to afford the almost pure title compound (4.74 g, yield: 99%).

$^1$H NMR (DMSO-d$_6$, 400 MHz): δ 2.96 (s, 3H), 5.27 (d, 2H, J$_{PH}$=13.5 Hz), 5.59 (d, 1H, J=1.7 Hz), 5.91 (dd, 1H, J=1.7, 1.7 Hz), 6.69 (d, 1H, J=1.7 Hz), 7.60-8.00 (m, 15H). $^{13}$C NMR (DMSO-d$_6$, 100 MHz): δ 20.5, 21.0, 33.1, 107.6, 107.6, 110.8, 110.9, 116.7, 116.8, 117.6, 118.5, 123.8, 123.8, 130.0, 130.1, 133.8, 133.9, 135.1, 135.1. IR vmax (KBr): 3116, 3098, 3077, 3054, 3001, 2992, 2866, 2837, 2765, 1486, 1437, 1306, 1143, 1108, 998, 745, 736, 716, 692, 520, 505, 486 cm$^{-1}$.

Additionally, following the procedure mentioned above, a similar reaction was carried out using 1-methyl-2-(N,N-dimethylaminomethyl)-1H-pyrrole, 1-methyl-2-(N,N-diethylaminomethyl)-1H-pyrrole and 1-methyl-2-(piperidin-1-ylmethyl)-1H-pyrrole as the starting materials instead of 1-methyl-2-(pyrrolidin-1-ylmethyl)-1H-pyrrole, and propionyl chloride or isobutyloyl chloride as the reagent instead of acetyl chloride to afford the title compound in the same yield.

Example 22

(4-Methoxybenzyl)(triphenyl)phosphonium iodide

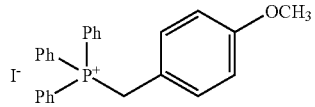

To a suspension of triphenylphosphine (4.92 g, 18.8 mmol) in acetonitrile (10 mL) was added acetyl chloride (1.34 mL, 18.8 mmol) at room temperature with stirring, and the resulting mixture was warmed to about 50° C. Subsequently, to the reaction mixture was added dropwise slowly a solution of 1-(4-methoxybenzyl)pyrrolidine (1.00 g, 5.23 mmol) in toluene (10 mL) below 60° C. with stirring, and the resulting mixture was stirred at about 50° C. for 72 hours. After cooling the reaction mixture to room temperature, water (20 mL) and n-hexane (10 mL) were added to the reaction mixture, and the resulting mixture was partitioned. To the aqueous layer separated were added successively water (10 mL) and sodium iodide (0.94 g, 6.28 mmol) with stirring, and the resulting mixture was stirred under ice-cooling for 1 hour. After stirring, the precipitate formed was collected by filtration to afford the almost pure title compound (2.31 g, yield: 87%).

$^1$H NMR (DMSO-d$_6$, 400 MHz): δ 3.70 (s, 3H), 5.14 (d, 2H, J$_{PH}$=32.0 Hz), 6.70-7.00 (m, 4H), 7.60-8.00 (m, 15H). $^{13}$C NMR (DMSO-d$_6$, 100 MHz): δ 27.2, 27.7, 55.1, 114.2, 114.2, 117.4, 118.3, 119.0, 119.0, 130.0, 130.1, 131.9, 132.0, 133.9, 134.0, 135.0, 135.0, 159.1, 159.1. IR vmax (KBr): 3036, 3005, 2962, 2882, 2854, 2787, 1610, 1584, 1512, 1439, 1254, 1178, 1112, 1030, 836, 740, 719, 688, 510 cm$^{-1}$.

Example 23

Triphenyl(thien-2-ylmethyl)phosphonium iodide

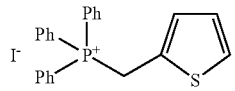

To a suspension of triphenylphosphine (6.66 g, 25.5 mmol) in acetonitrile (10 mL) was added acetyl chloride (1.80 mL, 25.5 mmol) at room temperature with stirring, and the resulting mixture was warmed to about 50° C. Subsequently, to the reaction mixture was added dropwise slowly a solution of 2-(dimethylaminomethyl)thiophene (1.00 g, 7.08 mmol) in toluene (10 mL) below 60° C. with stirring, and the resulting mixture was stirred at about 50° C. for 75 hours. After cooling the reaction mixture to room temperature, water (20 mL) and n-hexane (10 mL) were added to the reaction mixture, and the resulting mixture was partitioned. To the aqueous layer separated were added successively water (10 mL) and sodium iodide (1.27 g, 8.50 mmol) with stirring, and the resulting mixture was stirred under ice-cooling for 1 hour. After stirring, the precipitate formed was collected by filtration to afford the almost pure title compound (2.94 g, yield: 85%).

$^1$H NMR (DMSO-d$_6$, 400 MHz): δ 5.51 (d, 2H, J$_{PH}$=14.6 Hz), 6.70-6.80 (m, 1H), 6.90-7.00 (m, 1H), 7.40-7.50 (m, 1H), 7.60-8.00 (m, 15H). $^{13}$C NMR (DMSO-d$_6$, 100 MHz): δ 23.7, 24.2, 117.3, 118.1, 127.3, 127.4, 127.9, 127.9, 128.3, 128.4, 130.1, 130.2, 130.4, 130.5, 133.9, 134.0, 135.2, 135.2. IR vmax (KBr): 3065, 3046, 3004, 2986, 2867, 2829, 1585, 1484, 1435, 1161, 1109, 995, 860, 754, 742, 720, 690, 516, 498 cm$^{-1}$.

Example 24

[(5-Methyl-2-furyl)methyl](triphenyl)phosphonium iodide

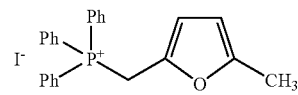

To a suspension of triphenylphosphine (6.79 g, 25.9 mmol) in acetonitrile (10 mL) was added acetyl chloride (1.84 mL, 25.9 mmol) at room temperature with stirring, and the resulting mixture was warmed to about 50° C. Subsequently, to the reaction mixture was added dropwise slowly a solution of N,N,5-trimethylfurfurylamine (1.00 g, 7.18 mmol) in toluene (10 mL) below 60° C. with stirring, and the resulting mixture was stirred at about 50° C. for 72 hours. After cooling the reaction mixture to room temperature, water (20 mL) and n-hexane (10 mL) were added to the reaction mixture, and the resulting mixture was partitioned. To the aqueous layer separated were added successively water (10 mL) and sodium iodide (1.29 g, 8.61 mmol) with stirring, and the resulting mixture was stirred under ice-cooling for 1 hour. After stirring, the precipitate formed was collected by filtration to afford the almost pure title compound (3.20 g, yield: 92%).

$^1$H NMR (DMSO-d$_6$, 400 MHz): δ 2.04 (s, 3H), 5.32 (d, 2H, J$_{PH}$=14.5 Hz), 5.95-6.05 (m, 2H), 7.60-8.00 (m, 15H). $^{13}$C NMR (DMSO-d$_6$, 100 MHz): δ 13.0, 22.7, 23.2, 107.3, 107.3, 112.8, 112.9, 117.5, 118.4, 130.0, 130.1, 133.8, 133.9, 135.1, 135.1, 139.5, 139.6, 152.6, 152.7. IR vmax (KBr): 3050, 3007, 2988, 2871, 2832, 2770, 1715, 1611, 1586, 1561, 1484, 1437, 1143, 1111, 1023, 996, 943, 799, 745, 732, 689, 522, 504, 485 cm$^{-1}$.

POSSIBILITY OF INDUSTRIAL USE

The present invention is useful for providing optically active 4,4-di-substituted oxazolidine derivatives and procedures for their preparation. The preparation procedures of the present invention have excellent advantages in the following respects, compared with the prior art: 1) increase in yield, 2) improvement in stereoselectivity, 3) extremely low-temperature reaction which is unsuitable for industrial large-scale synthesis is not necessary, and 4) column-chromatographic purification of intermediates is not needed in any step of these synthetic processes.

Furthermore, the compounds having the general formula (Id), which are optically active 4,4-di-substituted oxazolidine derivatives encompassed in the present invention, are useful as the synthetic intermediates in the preparation of optically active α,α-di-substituted α-amino acid derivatives having an excellent glutamate receptor antagonistic action or optically active α,α-di-substituted amino alcohol derivatives having new immunosuppressive action.

Additionally, according to the present invention, the substituted methylenephosphonium salt which is useful as a synthetic intermediate in the preparation of compounds having the general formula (Id) and various kinds of medicines can be obtained conveniently in a high yield.

The invention claimed is:

1. An optically active 4,4-di-substituted-oxazolidine compound having a formula (I)

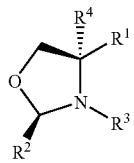

(I)

wherein
- $R^1$ represents a $C_1$-$C_3$ alkyl group which is substituted with one substituent from a Substituent group A, a $C_2$-$C_3$ alkenyl group which is substituted with one substituent selected from the Substituent group A, a halogenated methyl group, a hydroxymethyl group, a formyl group or a phosphonium methyl group,
- $R^2$ represents a $C_1$-$C_6$ alkyl group, a $C_3$-$C_{10}$ cycloalkyl group or a phenyl group,
- $R^3$ represents a methoxycarbonyl group,
- $R^4$ represents a $C_1$-$C_6$ alkyl group or a $C_2$-$C_6$ alkenyl group, the Substituent group A represents a phenyl group which is unsubstituted or substituted with from 1 to 3 substituents selected from the group consisting of a halogen atom, a cyano group, a phenyl group, a $C_1$-$C_8$ alkyl group, a $C_1$-$C_8$ alkoxy group and a $C_2$-$C_8$ alkanoyl group; a thienyl group; a N-methylpyrrolyl group; or a furanyl group.

2. The optically active 4,4-di-substituted oxazolidine compound having the formula (I) according to claim 1, wherein $R^1$ represents a formyl group.

3. The optically active 4,4-di-substituted oxazolidine compound having the formula (I) according to claim 1, wherein $R^1$ represents a hydroxymethyl group.

4. The optically active 4,4-di-substituted oxazolidine compound having the formula (I) according to claim 1, wherein $R^1$ represents an ethyl group or a vinyl group, said ethyl group and said vinyl group each being substituted with one substituent selected from the group consisting of a 4-bromophenyl group, a 4-iodophenyl group, a 4-octylphenyl group, a 4-heptyloxyphenyl group, a 4-octanoylphenyl group, a thienyl group and a N-methylpyrrolyl group.

5. The optically active 4,4-di-substituted oxazolidine compound having the formula (I) according to claim 1, wherein $R^1$ represents an ethyl group or a vinyl group, said ethyl group and said vinyl group each being substituted with a N-methylpyrrolyl group.

6. The optically active 4,4-di-substituted oxazolidine compound having the formula (I) according to claim 1, wherein $R^2$ represents an isopropyl group, a t-butyl group, a diethylmethyl group, a cyclohexyl group or an adamantyl group.

7. The optically active 4,4-di-substituted oxazolidine compound having the formula (I) according to claim 1, wherein $R^2$ represents a t-butyl group.

8. The optically active 4,4-di-substituted oxazolidine compound having the formula (I) according to claim 1, wherein $R^4$ represents a methyl group.

9. A method for the preparation of a compound having a formula (Ib) shown below comprising reacting a compound having a formula (Ia) shown below with a reducing reagent in a solvent,

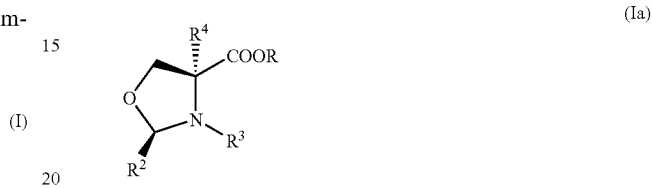

(Ia)

wherein
- R represents a $C_1$-$C_6$ alkyl group, a $C_2$-$C_6$ alkenyl group, a phenyl group or a benzyl group,
- $R^2$ represents a $C_1$-$C_6$ alkyl group, a $C_3$-$C_{10}$ cycloalkyl group or a phenyl group,
- $R^3$ represents a methoxycarbonyl group, and
- $R^4$ represents a $C_1$-$C_6$ alkyl group or a $C_2$-$C_6$ alkenyl group,

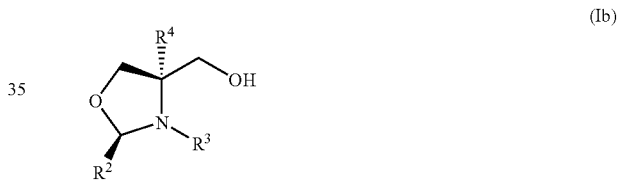

(Ib)

wherein
$R^2$, $R^3$ and $R^4$ have the same meanings as indicated above.

10. The method for the preparation of a compound having the formula (Ib) according to claim 9, wherein the reducing agent is a combination of potassium borohydride and lithium chloride.

11. The method for the preparation of a compound having a formula (Ic) shown below comprising reacting a compound having a formula (Ib) shown below with an oxidizing agent in a solvent,

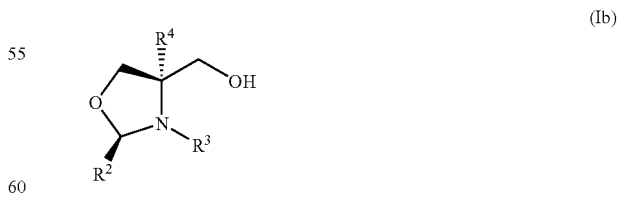

(Ib)

wherein
- $R^2$ represents a $C_1$-$C_6$ alkyl group, a $C_3$-$C_{10}$ cycloalkyl group or a phenyl group,
- $R^3$ represents a methoxycarbonyl group, and
- $R^4$ represents a $C_1$-$C_6$ alkyl group or a $C_2$-$C_6$ alkenyl group,

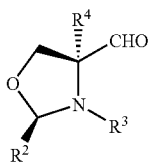

wherein $R^2$, $R^3$ and $R^4$ have the same meanings as indicated above.

12. The method for the preparation of a compound having the formula (Ic) according to claim 11, wherein the oxidizing agent is a combination of TEMPO, sodium bromide, sodium hypochloride and sodium hydrogencarbonate.

13. A method for the preparation of a compound having a formula (Ic) shown below comprising reacting a compound having a formula (Ia) shown below with a reducing agent in a solvent,

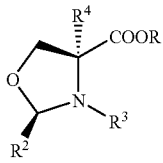

wherein

R represents a $C_1$-$C_6$ alkyl group, a $C_2$-$C_6$ alkenyl group, a phenyl group or a benzyl group, $R^2$ represents a $C_1$-$C_6$ alkyl group, a $C_3$-$C_{10}$ cycloalkyl group or a phenyl group, $R^3$ represents a methoxycarbonyl group, and $R^4$ represents a $C_1$-$C_6$ alkyl group or a $C_2$-$C_6$ alkenyl group,

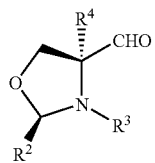

wherein $R^2$, $R^3$ and $R^4$ have the same meanings as indicated above.

14. The method for the preparation of a compound having the general formula (Ic) according to claim 13, wherein the reducing agent is sodium bis(2-methoxyethoxy)aluminum hydride.

15. The optically active 4,4-di-substituted oxazolidine compound according to claim 1, wherein the compound is 2-t-butyl-4-hydroxymethyl-4-methyl-1,3-oxazolidine-3-carboxylic acid methyl ester.

16. The optically active 4,4-di-substituted oxazolidine compound according to claim 1, wherein the compound is 2-t-butyl-4-formyl-4-methyl-1,3-oxazolidine-3- carboxylicacid methyl ester.

17. The optically active 4,4-di-substituted substituted oxazolidine compound according to claim 1, wherein the compound is 2-t-butyl-4-methyl-4-[2-(1-methyl-1H-pyrrol-2-yl)ethyl]-1,3-oxazolidine-3-carboxylic acid methyl ester.

* * * * *